(12) United States Patent
Carson et al.

(10) Patent No.: US 8,914,146 B2
(45) Date of Patent: Dec. 16, 2014

(54) METHODS AND APPARATUS FOR FILLING OF PACKAGINGS WITH MEDICATIONS

(75) Inventors: Bradley Carson, Ottawa Hills, OH (US); Darin L. Danelski, Oconomowoc, WI (US); Joseph T. DeDeo, Mount Laurel, NJ (US); Jack M. Friday, Monroe, MI (US); Mitchell Mosbacher, Maumee, OH (US)

(73) Assignee: Omnicare, Inc., Cincinnati, OH (US)

( * ) Notice: Subject to any disclaimer, the term of this patent is extended or adjusted under 35 U.S.C. 154(b) by 71 days.

(21) Appl. No.: 13/546,035

(22) Filed: Jul. 11, 2012

(65) Prior Publication Data

US 2013/0018503 A1 Jan. 17, 2013

Related U.S. Application Data

(60) Provisional application No. 61/506,390, filed on Jul. 11, 2011.

(51) Int. Cl.
| | |
|---|---|
| G06F 7/00 | (2006.01) |
| B65B 57/16 | (2006.01) |
| B65B 5/10 | (2006.01) |
| G06F 19/00 | (2011.01) |
| G07F 17/00 | (2006.01) |
| A61J 1/03 | (2006.01) |
| A61J 7/04 | (2006.01) |

(52) U.S. Cl.
CPC .............. B65B 57/16 (2013.01); B65B 5/103 (2013.01); G06F 19/3462 (2013.01); G07F 17/0092 (2013.01); A61J 1/035 (2013.01); A61J 7/04 (2013.01)
USPC ........... 700/216; 700/213; 700/214; 700/215; 700/220; 700/231

(58) Field of Classification Search
None
See application file for complete search history.

(56) References Cited

U.S. PATENT DOCUMENTS

| | | | |
|---|---|---|---|
| 4,655,026 | A | 4/1987 | Wigoda |
| 4,733,362 | A | 3/1988 | Haraguchi |
| 5,081,816 | A | 1/1992 | Cardinali |
| 5,646,912 | A | 7/1997 | Cousin |
| 5,765,606 | A | 6/1998 | Takemasa et al. |

(Continued)

OTHER PUBLICATIONS

International Searching Authority, Search Report and Written Opiinion issued in related International application No. PCT/US12/46227 dated Sep. 24, 2012.

(Continued)

Primary Examiner — Yolanda Cumbess
(74) Attorney, Agent, or Firm — Wood, Herron & Evans, LLP

(57) ABSTRACT

Methods for filling packagings with at least one medication include producing filling instructions, operating a packaging station to fill packagings, and verifying that each of the packagings is filled correctly. The production of filling instructions includes an allocation of medications to separated compartments in the packagings. Each packaging receives a single medication pass for a specified time on a specified day, or a medicine pass for administration on an as needed basis. The packaging station may include a manual packaging station at which an operator follows prompts to move canisters of medications, pills from the canisters, and trays of packagings to fill the packagings. The manual packaging station includes a shutter assembly with shutters configured to selectively provide access to only one compartment in each packaging at a time, thereby reducing the likelihood of filling errors. Apparatus for filling packagings may include the same manual packaging station.

21 Claims, 37 Drawing Sheets

(56) References Cited

U.S. PATENT DOCUMENTS

| | | |
|---|---|---|
| 5,805,455 A | 9/1998 | Lipps |
| 5,845,255 A | 12/1998 | Mayaud |
| 6,006,946 A | 12/1999 | Williams et al. |
| 6,036,812 A | 3/2000 | Williams et al. |
| 6,119,737 A | 9/2000 | Yuyama et al. |
| 6,317,648 B1 | 11/2001 | Sleep et al. |
| 6,345,487 B1 | 2/2002 | Luciano et al. |
| 6,370,841 B1 | 4/2002 | Chudy et al. |
| 6,449,927 B2 | 9/2002 | Hebron et al. |
| 6,471,088 B1 | 10/2002 | Uema et al. |
| 6,481,180 B1 | 11/2002 | Takahashi et al. |
| 6,522,945 B2 | 2/2003 | Sleep et al. |
| 6,597,969 B2 | 7/2003 | Greenwald et al. |
| 6,609,047 B1 | 8/2003 | Lipps |
| 6,681,149 B2 | 1/2004 | William et al. |
| 6,690,998 B1 | 2/2004 | Yuyama |
| 6,717,598 B1 | 4/2004 | Melton, Jr. et al. |
| 6,749,085 B2 | 6/2004 | Garrant et al. |
| 6,760,643 B2 | 7/2004 | Lipps |
| 6,775,588 B1 | 8/2004 | Peck |
| 6,775,589 B2 | 8/2004 | William et al. |
| 6,983,579 B2 | 1/2006 | Rice et al. |
| 6,988,634 B2 | 1/2006 | Varis |
| 6,990,383 B2 | 1/2006 | Hoppes et al. |
| 6,993,402 B2 | 1/2006 | Klass et al. |
| 7,006,893 B2 | 2/2006 | Hart et al. |
| 7,016,752 B1 | 3/2006 | Ruben et al. |
| 7,016,766 B2 | 3/2006 | William et al. |
| 7,027,886 B2 | 4/2006 | Hoppes et al. |
| 7,072,840 B1 | 7/2006 | Mayaud |
| 7,182,105 B2 | 2/2007 | Feehan et al. |
| 7,185,476 B1 | 3/2007 | Siegel et al. |
| 7,203,571 B2 | 4/2007 | Kirsch et al. |
| 7,225,131 B1 | 5/2007 | Bangalore et al. |
| 7,225,597 B1 | 6/2007 | Knoth |
| 7,289,879 B2 | 10/2007 | William et al. |
| 7,317,525 B2 | 1/2008 | Rzasa et al. |
| RE40,453 E | 8/2008 | Lasher et al. |
| 7,426,814 B2 | 9/2008 | Knoth |
| 7,454,880 B1 | 11/2008 | Austin et al. |
| 7,471,993 B2 | 12/2008 | Rosenblum |
| 7,496,521 B1 | 2/2009 | Louie et al. |
| 7,555,875 B2 | 7/2009 | Kim |
| 7,574,844 B2 | 8/2009 | Kamineni |
| 7,610,115 B2 | 10/2009 | Rob et al. |
| 7,636,718 B1 | 12/2009 | Steen et al. |
| 7,637,079 B2 | 12/2009 | Klingel et al. |
| 7,668,618 B2 | 2/2010 | Szesko et al. |
| 7,680,554 B2 | 3/2010 | Erickson et al. |
| 7,689,318 B2 | 3/2010 | Draper |
| 7,690,173 B2 | 4/2010 | Luciano, Jr. et al. |
| 7,721,512 B2 | 5/2010 | Siegel et al. |
| 7,747,345 B2 | 6/2010 | Ohmura et al. |
| 7,774,210 B1 | 8/2010 | Sandberg |
| 7,779,614 B1 | 8/2010 | McGonagle et al. |
| 7,783,383 B2 | 8/2010 | Eliuk et al. |
| 7,784,244 B2 | 8/2010 | Siegel |
| 7,805,217 B2 | 9/2010 | Chudy et al. |
| 7,813,880 B2 | 10/2010 | Vaidya et al. |
| 7,818,177 B1 | 10/2010 | Bangalore et al. |
| 7,818,184 B2 | 10/2010 | Penny et al. |
| 7,818,950 B1 | 10/2010 | McGonagle et al. |
| 7,835,924 B1 | 11/2010 | Palazzolo et al. |
| 7,848,846 B2 | 12/2010 | Uema et al. |
| 7,861,495 B2 | 1/2011 | Yuyama et al. |
| 7,882,680 B2 | 2/2011 | Siegel et al. |
| 7,886,506 B2 | 2/2011 | Knoth et al. |
| 7,908,827 B2 | 3/2011 | Knoth |
| 7,922,037 B2 | 4/2011 | Ohmura et al. |
| 7,930,066 B2 | 4/2011 | Eliuk et al. |
| 7,930,869 B2 | 4/2011 | Rozenkranz |
| 7,946,101 B1 | 5/2011 | McGonagle et al. |
| 7,950,206 B2 | 5/2011 | Knoth |
| 2002/0042725 A1 | 4/2002 | Mayaud |
| 2002/0143429 A1 | 10/2002 | Yuyama et al. |
| 2002/0184051 A1 | 12/2002 | Yu et al. |
| 2003/0085235 A1 | 5/2003 | William et al. |
| 2003/0200726 A1 | 10/2003 | Rast |
| 2004/0064215 A1 | 4/2004 | Greeven et al. |
| 2004/0134043 A1 | 7/2004 | Uema et al. |
| 2004/0148054 A1 | 7/2004 | Schwartz |
| 2004/0249498 A1 | 12/2004 | William et al. |
| 2004/0261357 A1 | 12/2004 | Takahashi et al. |
| 2005/0139506 A1 | 6/2005 | Lorenzato |
| 2006/0086640 A1 | 4/2006 | Luciano et al. |
| 2006/0107623 A1 | 5/2006 | Rice et al. |
| 2006/0161298 A1 | 7/2006 | DiMaggio |
| 2006/0253346 A1 | 11/2006 | Gomez |
| 2007/0017181 A1 | 1/2007 | Jacobsen et al. |
| 2007/0125046 A1 | 6/2007 | Siegel et al. |
| 2007/0157548 A1 | 7/2007 | Knoth |
| 2007/0157551 A1 | 7/2007 | Yuyama et al. |
| 2007/0162179 A1* | 7/2007 | Freudelsperger ............ 700/216 |
| 2007/0169439 A1 | 7/2007 | Rice et al. |
| 2007/0173971 A1 | 7/2007 | Richardson et al. |
| 2007/0250346 A1 | 10/2007 | Luciano et al. |
| 2007/0267430 A1 | 11/2007 | Luciano et al. |
| 2007/0270998 A1 | 11/2007 | Luciano et al. |
| 2007/0289258 A1 | 12/2007 | Jung et al. |
| 2008/0071648 A1 | 3/2008 | Kim |
| 2008/0155718 A1 | 6/2008 | Kim |
| 2008/0162188 A1 | 7/2008 | Kripalani et al. |
| 2008/0190076 A1 | 8/2008 | Klingel et al. |
| 2008/0190953 A1 | 8/2008 | Mallett et al. |
| 2008/0195246 A1 | 8/2008 | Tribble et al. |
| 2008/0210701 A1 | 9/2008 | Cooper |
| 2008/0229718 A1 | 9/2008 | Feehan et al. |
| 2008/0300718 A1 | 12/2008 | Austin et al. |
| 2008/0312767 A1 | 12/2008 | Rice et al. |
| 2008/0312957 A1 | 12/2008 | Luciano, Jr. et al. |
| 2009/0012820 A1* | 1/2009 | Bishop et al. ............... 705/3 |
| 2009/0076338 A1 | 3/2009 | Zdeblick et al. |
| 2009/0076857 A1 | 3/2009 | Eletreby et al. |
| 2009/0120042 A1 | 5/2009 | Zieher |
| 2009/0132083 A1 | 5/2009 | Rice et al. |
| 2009/0133362 A1 | 5/2009 | Bentele et al. |
| 2009/0152291 A1 | 6/2009 | Ohmura et al. |
| 2009/0164042 A1 | 6/2009 | Handfield et al. |
| 2009/0210247 A1 | 8/2009 | Chudy et al. |
| 2009/0277815 A1 | 11/2009 | Kohl |
| 2009/0312855 A1 | 12/2009 | Biehler et al. |
| 2009/0319301 A1 | 12/2009 | Hyde et al. |
| 2009/0321296 A1 | 12/2009 | Luciano, Jr. et al. |
| 2009/0321465 A1 | 12/2009 | Knoth et al. |
| 2009/0321470 A1 | 12/2009 | Knoth |
| 2009/0321472 A1 | 12/2009 | Knoth |
| 2010/0004782 A1 | 1/2010 | Siegel et al. |
| 2010/0017031 A1 | 1/2010 | Rob et al. |
| 2010/0030667 A1 | 2/2010 | Chudy et al. |
| 2010/0031611 A1 | 2/2010 | Ali et al. |
| 2010/0042255 A1 | 2/2010 | Boutin |
| 2010/0069213 A1 | 3/2010 | Luciano, Jr. et al. |
| 2010/0070070 A1 | 3/2010 | Stemmle |
| 2010/0071320 A1 | 3/2010 | Ali et al. |
| 2010/0087935 A1 | 4/2010 | Pettus et al. |
| 2010/0089997 A1 | 4/2010 | Carson et al. |
| 2010/0100391 A1 | 4/2010 | Daya et al. |
| 2010/0106515 A1 | 4/2010 | McCoy |
| 2010/0121486 A1 | 5/2010 | Yuyama et al. |
| 2010/0145500 A1 | 6/2010 | Luciano, Jr. et al. |
| 2010/0147734 A1 | 6/2010 | Luciano, Jr. et al. |
| 2010/0152884 A1 | 6/2010 | Rice et al. |
| 2010/0153129 A1 | 6/2010 | Luciano, Jr. et al. |
| 2010/0153130 A1 | 6/2010 | Luciano, Jr. et al. |
| 2010/0161353 A1 | 6/2010 | Mayaud |
| 2010/0168904 A1 | 7/2010 | Henderson et al. |
| 2010/0172724 A1 | 7/2010 | Hawkes et al. |
| 2010/0174552 A1 | 7/2010 | Hawkes et al. |
| 2010/0176145 A1 | 7/2010 | Hawkes et al. |
| 2010/0198392 A1 | 8/2010 | Eliuk et al. |
| 2010/0228562 A1 | 9/2010 | Luciano, Jr. et al. |
| 2010/0230005 A1 | 9/2010 | Siegel et al. |
| 2010/0234982 A1 | 9/2010 | Sankaran et al. |
| 2010/0241270 A1 | 9/2010 | Eliuk et al. |

(56) References Cited

U.S. PATENT DOCUMENTS

| | | |
|---|---|---|
| 2010/0275552 A1 | 11/2010 | Siegel |
| 2010/0305975 A1 | 12/2010 | Daya et al. |
| 2011/0000170 A1 | 1/2011 | Burg et al. |
| 2011/0011034 A1 | 1/2011 | Mahar |
| 2011/0014351 A1 | 1/2011 | Reider et al. |
| 2011/0015782 A1 | 1/2011 | Chudy et al. |
| 2011/0060448 A1 | 3/2011 | Gotou et al. |
| 2011/0071667 A1 | 3/2011 | Spano, Jr. et al. |
| 2011/0100863 A1 | 5/2011 | Luciano |
| 2011/0112686 A1 | 5/2011 | Nolan et al. |
| 2011/0113727 A1 | 5/2011 | Bonner |

OTHER PUBLICATIONS

The International Bureau of WIPO, International Preliminary Report on Patentability in copending International Patent Application No. PCT/US2012/046227 dated Jan. 14, 2014 (9 pages).

* cited by examiner

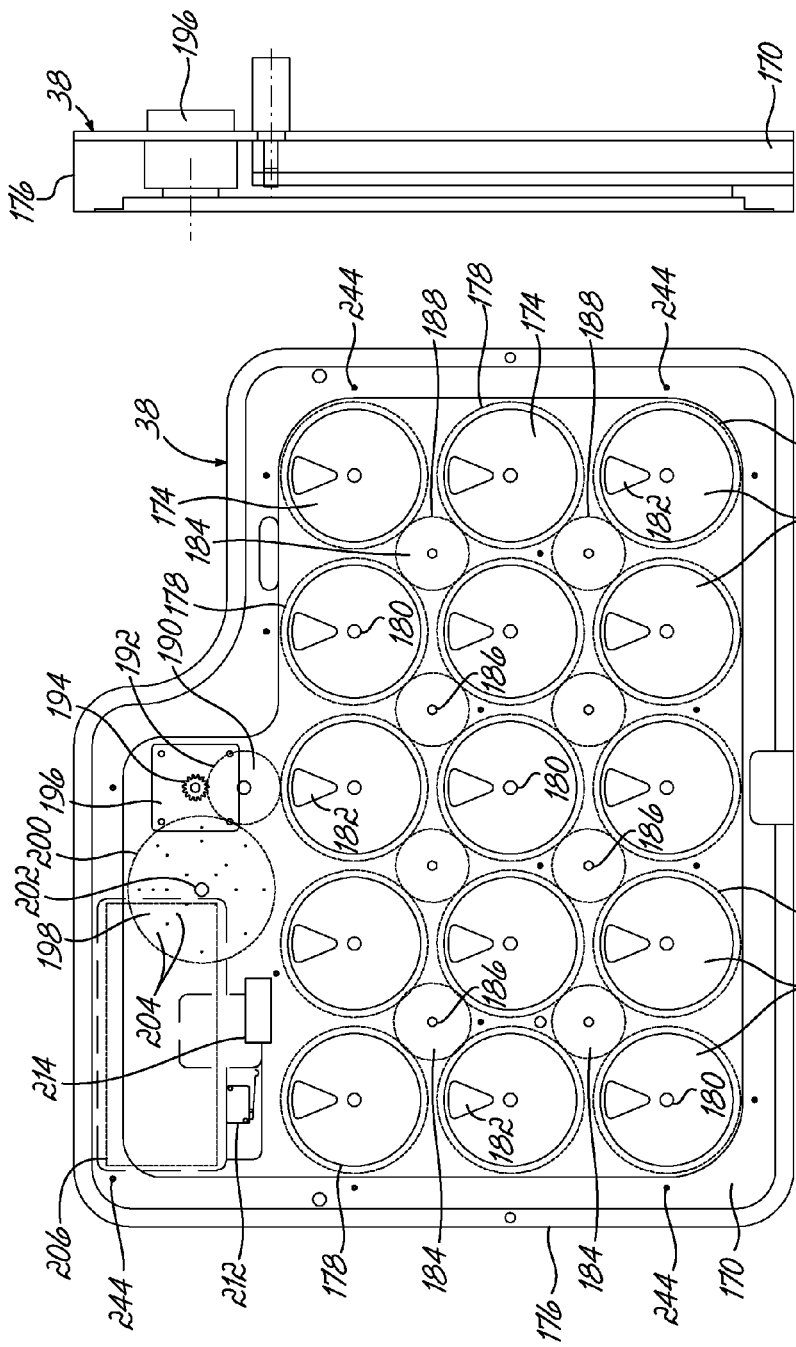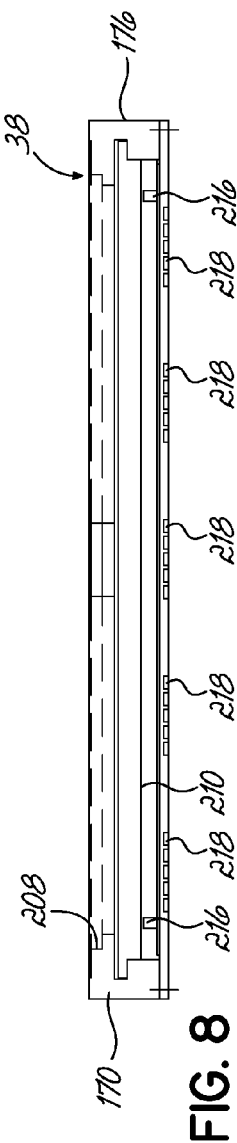

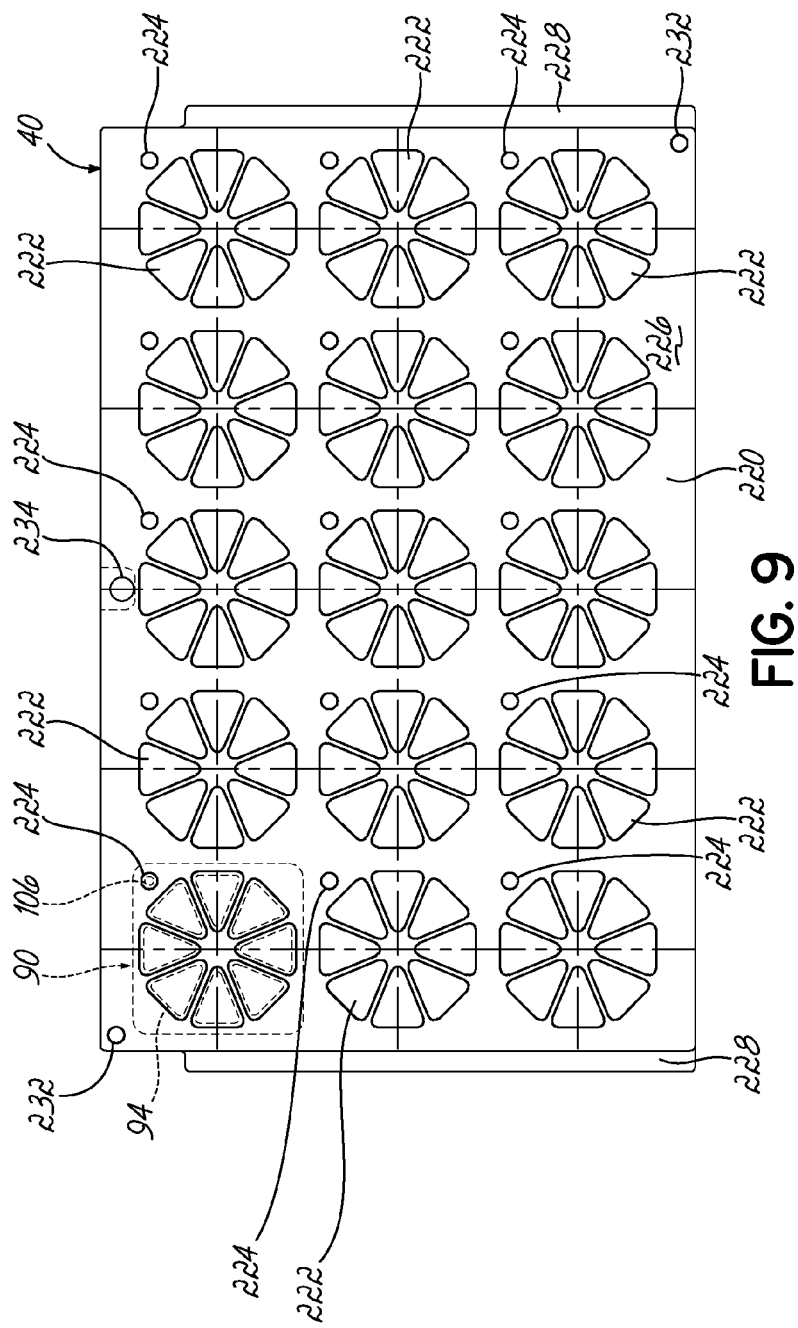
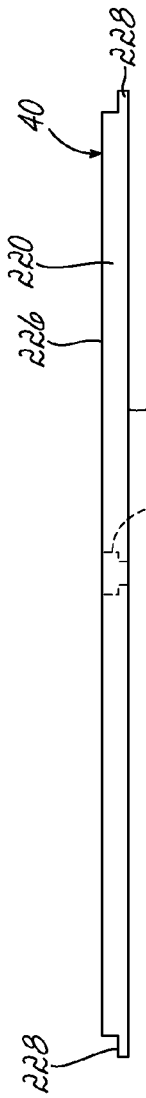
FIG. 9
FIG. 10

FIG. 19C

| | | Blister Pack | Cavity | | | | | | | |
|---|---|---|---|---|---|---|---|---|---|---|
| | | | A | B | C | D | E | F | G | H |
| Day 1 | Morning | 1 | Drug A | Drug C | | | | | | |
| | Lunchtime | 2 | Drug D | Blank | | | | | | |
| | Evening | 3 | Drug C | Blank | | | | | | |
| | Bedtime | 4 | Drug A | Blank | | | | | | |
| Day 2 | Morning | 5 | Drug A | Drug C | | | | | | |
| | Lunchtime | 6 | Drug B | Drug D | | | | | | |
| | Evening | 7 | Drug C | Blank | | | | | | |
| | Bedtime | 8 | Drug A | Blank | | | | | | |
| Day 3 | Morning | 9 | Drug A | Drug C | | | | | | |
| | Lunchtime | 10 | Drug D | Blank | | | | | | |
| | Evening | 11 | Drug C | Blank | | | | | | |
| | Bedtime | 12 | Drug A | Blank | | | | | | |
| Day 4 | Morning | 13 | Drug A | Drug C | | | Blank | | | |
| | Lunchtime | 14 | Drug B | Drug D | | | | | | |
| | Evening | 15 | Drug C | Blank | | | | | | |
| | Bedtime | 16 | Drug A | Blank | | | | | | |
| Day 5 | Morning | 17 | Drug A | Drug C | | | | | | |
| | Lunchtime | 18 | Drug D | Blank | | | | | | |
| | Evening | 19 | Drug C | Blank | | | | | | |
| | Bedtime | 20 | Drug A | Blank | | | | | | |
| Day 6 | Morning | 21 | Drug A | Drug C | | | | | | |
| | Lunchtime | 22 | Drug B | Drug D | | | | | | |
| | Evening | 23 | Blank | Blank | | | | | | |
| | Bedtime | 24 | Drug A | Blank | | | | | | |
| Day 7 | Morning | 25 | Drug A | Drug C | | | | | | |
| | Lunchtime | 26 | Drug D | Blank | | | | | | |
| | Evening | 27 | Blank | Blank | | | | | | |
| | Bedtime | 28 | Drug A | Blank | | | | | | |

| | Blister Pack | Cavity |  |  |  |  |  |  |  |
|---|---|---|---|---|---|---|---|---|---|
| | | A | B | C | D | E | F | G | H |
| Day 1 Lunchtime | 1 | Drug A | Drug C | | | | | | |
| Day 1 Evening | 2 | Drug C | Blank | | | | | | |
| Day 1 Bedtime | 3 | Drug A | Drug D | | | | | | |
| Day 2 Lunchtime | 4 | Drug A | Drug C | | | | | | |
| Day 2 Evening | 5 | Drug C | Drug B | | | | | | |
| Day 2 Bedtime | 6 | Drug A | Drug D | | | | | | |
| Day 3 Lunchtime | 7 | Drug A | Drug C | | | | | | |
| Day 3 Evening | 8 | Drug C | Blank | | | | | | |
| Day 3 Bedtime | 9 | Drug A | Drug D | | | | | | |
| Day 4 Lunchtime | 10 | Drug A | Drug C | | | | | | |
| Day 4 Evening | 11 | Drug B | Drug C | | | | | | |
| Day 4 Bedtime | 12 | Drug A | Drug D | | | | | | |
| Day 5 Lunchtime | 13 | Drug A | Drug C | | | | | | |
| Day 5 Evening | 14 | Drug C | Blank | | | | | | |
| Day 5 Bedtime | 15 | Drug A | Blank | | | | | | |
| Day 6 Lunchtime | 16 | Drug A | Blank | | | | | | |
| Day 6 Evening | 17 | Drug B | Blank | | | | | | |
| Day 6 Bedtime | 18 | Drug A | Drug D | | | | | | |
| Day 7 Lunchtime | 19 | Drug A | Blank | | | | | | |
| Day 7 Evening | 20 | Blank | Blank | | | | | | |
| Day 7 Bedtime | 21 | Drug A | Drug D | | | | | | |

METHODS AND APPARATUS FOR FILLING OF PACKAGINGS WITH MEDICATIONS

CROSS-REFERENCE TO RELATED APPLICATIONS

The present application claims the benefit of U.S. Provisional Patent Application Ser. No. 61/506,390, filed Jul. 11, 2011, the disclosure of which is hereby incorporated by reference herein in its entirety. The present application is also related to co-pending U.S. application Ser. No. 13/529,554, filed Jun. 21, 2012 and entitled "METHODS AND APPARATUS FOR AUTOMATED FILLING OF PACKAGINGS WITH MEDICATIONS," the disclosure of which is hereby incorporated by reference herein in its entirety.

BACKGROUND

The invention relates generally to methods of filling packagings for medications and apparatus for assisting with manual filling or verification of filling of such packagings.

Prescription and non-prescription daily medications may be distributed to patients contained in a variety of different packages including conventional pill vials and blister packs. In many prescription dosing regimens, multiple medications are administered on a continuing basis to a patient at different times over the course of each day. The need to remove the medication from multiple different vials at specifically prescribed times each day can be confusing to a patient, especially senior patients. Patient confusion may contribute to partial prescription non-compliance or even complete prescription non-compliance if the patient fails to follow treatment directions.

To address this non-compliance concern, it would be desirable to provide a certain number of medication packages for each day that contain all of the medications to be consumed at specified times in the day (e.g., morning, lunchtime, evening, bedtime). Additionally, when multiple medications are to be administered to a patient, any potential drug contra-indication (whether detrimental or not) and the desired dosage intervals for each medication must be considered when determining how to fill these packages of medications. If, for example, the medication packages are provided for four specified daily times, each medication to be administered during that day must be allocated to the separate packages so as to maintain the desired dosing intervals and so as to avoid detrimental medication contra-indications.

Moreover, some patients have particular administration time preferences or life style choices that prevent them from reliably taking medications at a particular time of day, such as patients who do not awaken before lunchtime. For these patients, the medication for each day must be allocated to a smaller number of packages to avoid prescription non-compliance. However, detrimental drug contra-indications must necessarily be avoided even when using fewer medication packages per day.

In an exemplary application in which a patient receives four separate packagings of medications for each day, a monthly supply of the medications will require up to 120 packagings to be filled and verified. Some conventional filling systems move each packaging to be filled along a complex and lengthy path past a high number of bulk containers so that each medication to be placed in the packaging will be dispensed as the packagings move along the complex and lengthy path. Each packaging is then individually and manually verified by a trained technician or a pharmacist. Although such systems have utility when filling pill bottles with multiple doses of an individual medication, these systems are far less efficient when dispensing single unit doses of medication into a plurality of packagings for each patient. A pharmaceutical filling operation may be responsible for thousands of patients per month, which requires hundreds of thousands of packagings to be individually filled and verified. Even when using automated methods of filling packagings, a certain percentage of filled packagings must be verified for accuracy and quality by a trained technician or a pharmacist. These reviews can significantly increase the amount of time and human labor necessary to fill each order of monthly prescriptions and "take as needed" or PRN medications, on average. The conventional filling systems described above do not provide sufficient capacity to fill and verify the high number of packagings required on a monthly basis.

Consequently, improved methods and apparatus for filling packages with various medications are needed that can improve prescription compliance and provide sufficient filling and verification capacity to serve thousands of patients per month.

SUMMARY OF THE INVENTION

According to one embodiment of the invention, a method for filling packagings with at least one medication includes producing filling instructions for an order, including an allocation of medications to separated compartments in a plurality of the packagings. Each packaging is adapted to receive only the medication to be taken by a patient at a specified medicine pass time or as needed. The method also includes operating a packaging station to fill the plurality of the packagings with at least one medication according to the filling instructions. The method further includes verifying that each of the plurality of packagings has been accurately filled according to the filling instructions at a verification station. Consequently, the method enables efficient distribution of multiple prescriptions into individualized packages for convenient administration by a patient, thereby increasing patient drug compliance and satisfaction.

In one aspect, producing the filling instructions further includes receiving a plurality of prescriptions and analyzing the prescription data associated with each prescription. The filling instructions are generated based, at least in part, on the analyzed prescription data of each prescription. For example, the prescription data may include a medication type of each received prescription such that the generated filling instructions are based at least in part on those medication types. In another example, the prescription data may include a patient for each received prescription such that the generated filling instructions are based at least in part on the identified patient. When the patient has dosing preferences included in the prescription data, then the generated filling instructions are based, at least in part, on those patient dosing preferences. The prescription data may also include dosage instructions for each received prescription, and these dosage instructions will be used to generate the filling instructions.

In another aspect, producing filling instructions for an order further includes receiving a plurality of prescriptions for a patient and allocating each medication from the prescriptions to a plurality of packagings. Any undesirable drug contra-indications between two medications in any packaging may then be identified. If any such undesirable drug contra-indications exist, then the allocation of medications is modified to avoid such undesirable drug contra-indications. Patient administration time preferences may also be identified, in which case the allocation of medications to the packagings is further modified based on the administration time preferences. The allocation of medications to the packagings may further be optimized to minimize the number of packagings required to fill the entire order, and therefore minimize the number of med pass times for the patient.

In yet another aspect, the method further includes assigning an order to be filled at a packaging station only when that packaging station has sufficient inventory to fill the order. The inventory of a plurality of packaging stations is managed to enable optimization of filling of orders by the plurality of packaging stations. A single order may require filling at multiple packaging stations. In such circumstances, the method includes managing the filling and verification of the plurality of packagings in that order such that the entire order is prepared for collation together and shipment with minimized delays associated with operating multiple packaging stations.

In a further aspect, the packaging station is a manual packaging station. The manual packaging station includes at least one storage carousel with canisters of medications, a staging bar configured to temporarily retain the canisters, and a counting mechanism for dispensing a desired number of pills from the canisters. The manual packaging station also includes a loading table for holding a tray of the packagings to be filled. The operation of this manual packaging station includes delivering filling instructions to an operator so as to include directions on how to move canisters and how to dispense and fill medications from the canisters into the packagings on the tray. To this end, delivering the filling instructions may include determining a current batch of canisters needed to fill the packagings on the tray and prompting the worker to move canisters between the storage carousels and the staging bar to assemble the batch on the staging bar. Then the worker is prompted to take each canister to the counting mechanism to dispense the desired quantity of pills. Each dispensed set of pills is used at the loading table to fill the compartments of the packagings in the tray. This process is repeated for all canisters in the batch, and then the entire process is repeated for all batches needed to finish an order of packagings.

In another aspect, the loading table includes a shutter assembly for holding the tray. The shutter assembly includes a shutter located above each of the packagings with an opening configured to provide access to only one of the compartments of each packaging. Delivering the filling instructions then includes actuating the shutters so that only a first compartment is open for filling and activating a LED below each first compartment that is to be filled. The operator then fills these compartments and confirms that all of the intended compartments have received the medication. The first compartments are then imaged for use in downstream verification of the filling, and the process repeats for each compartment. In embodiments where the shutters are rotatable shutters, an actuator coupled to a gear train causes simultaneous indexed rotation of each shutter to provide access to the same compartment of each packaging. The LED may be configured to emit a light frequency that is optimized to maximize contrast of the pills or medications from the packaging during filling. The same type of shutter assembly and loading table may also be used as a manual verification station for comparing the intended filling of packagings with the actual filling during a verification process. If any compartments are incorrectly filled, the verification station can prompt the operator on how to correct these deficiencies.

In a further aspect, operating the packaging station further includes retrieving a sorted list of pending orders for a plurality of patients. A pending order is assigned to the manual packaging station only when sufficient inventory is available at that station. Furthermore, the pending orders assigned to the manual packaging station are prioritized in order to minimize the number of canister exchanges needed between batches, to further improve the efficiency of the filling process. Any time that the operator is prompted to move a canister from a first location to a second location during this filling process, the manual packaging station illuminates a LED or a display to prompt scanning of the canister and movement of the canister to the second location. Upon arrival at the second location, the LED or display will not be extinguished without verified scans of both the second location and the canister again, thereby ensuring that no mistakes are made during movement of multiple canisters.

In another embodiment according to the invention, an apparatus for filling a plurality of packagings includes a controller having a processor and a memory. The apparatus also includes program code resident in the memory and configured to be executed by the processor. The program code operates to load a plurality of prescriptions and generate filling instructions based at least in part on the loaded prescriptions. The medications of the prescriptions are allocated into compartments of separate packagings for each specified pass time or dosage as needed. The program code further operates a packaging station to fill the plurality of packagings according to the filling instructions and then verifies that each of the plurality of packagings has been accurately filled.

The apparatus may include at least one manual packaging station, at least one automated packaging station, and a verification station. As noted above, the verification station may be a loading table and shutter mechanism as used with the manual packaging stations. The use of these various packaging stations enables the orders of multiple patients to be allocated and filled most efficiently. Moreover, the provision of separate packagings for each pass time or each as needed use of medications for a patient greatly simplifies the administration of multiple prescriptions to a patient. Thus, the apparatus of the current invention improves patient compliance and reduces the time necessary to provide medications to a plurality of patients each month or other periodic time interval.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

FIG. 6 is a top view of the shutter assembly on the loading table of FIG. 5.

FIG. 7 is a side view of the shutter assembly of FIG. 6.

FIG. 8 is a front view of the shutter assembly of FIG. 6.

FIG. 9 is a top view of a tray used with the shutter assembly of FIG. 6 and the medication packaging of FIG. 2A.

FIG. 10 is a front view of the tray of FIG. 9.

FIG. 19C is a schematic chart used to illustrate the generation of packaging instructions based on the four prescriptions of FIG. 19B.

FIG. 19D is a schematic chart used to illustrate the generation of packaging instructions based on the four prescriptions of FIG. 19B as well as any patient preferences or drug contraindications.

DETAILED DESCRIPTION

Figure 1:
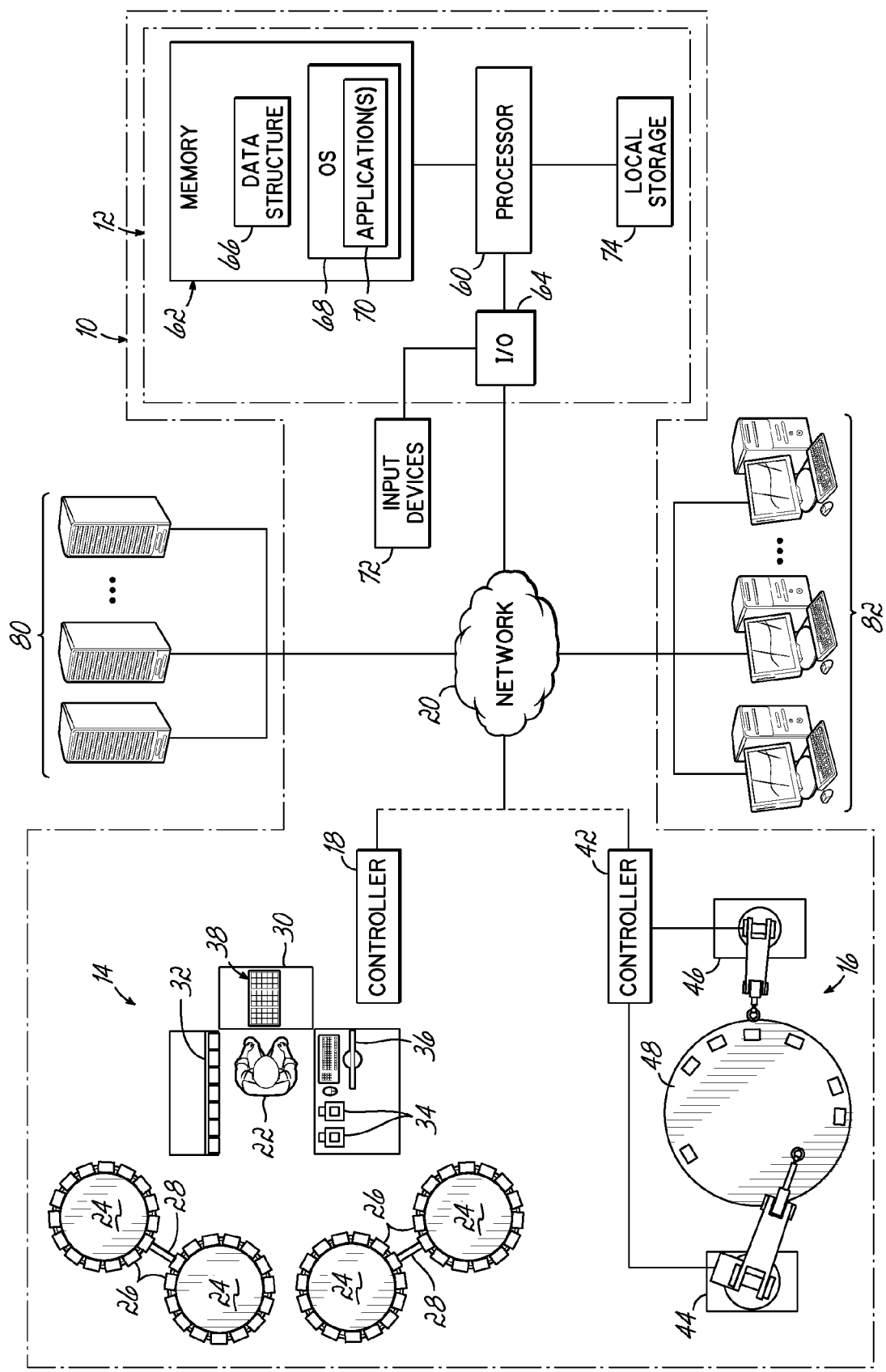
FIG. 1 is a schematic view of an exemplary embodiment of a drug packaging system according to the invention, the drug packaging system including a manual packaging station and an automated packaging station

With reference to FIG. 1, one exemplary embodiment of a drug packaging system 10 consistent with the invention is shown. The drug packaging system 10 includes a controller 12, one or more manual packaging stations 14, and one or more automated packaging stations 16. The controller 12 is configured to actuate the manual packaging stations 14 and the automated packaging stations 16 to fill a plurality of patient specific drug packages with a plurality of medications. One example of the patient specific drug packaging used throughout the following description is a blister pack (not shown in FIG. 1) described in further detail with reference to FIGS. 2A and 3 below. It will be understood that other types of drug packaging may be used in other embodiments of the invention. The blister packs are designed for distributing medications that are administered to a patient as part of long-term, maintenance care for chronic ailments and conditions. Patients, such as elderly or senior patients, may daily dispense and consume one or more medications (such as oral medications or other solid products) from one of the blister packs at pass times during the day, such as morning, lunchtime, evening, and bedtime. The blister packs conveniently simplify the administration of multiple medications by grouping all of the unit doses to be taken at a particular pass time into a single drug package. As a result, the blister packs improve drug delivery accuracy and medication regimen compliance, especially for senior aged patients who may be living at home independently or cared for in an assisted-care facility. Consequently, the manual and automated packaging stations 14, 16 are configured to optimize the filling process so that a maximum number of patients, each of whom may require 120 blister packs or more per month, may be served monthly by the drug packaging system 10. For example, in the scenario when additional blister packs are prepared for PRN or "take as needed" use, any number of blister packs may be filled for a particular patient in each month. The following description will focus on the regularly scheduled medication passes, but it will be understood that additional PRN blister packs or other blister packs may also be filled using the apparatus and methods described below.

With continued reference to FIG. 1, the manual packaging station 14 includes a machine controller 18 operatively connected to the controller 12 via network 20. The machine controller 18 of the manual packaging station 14 is configured to execute program code configured to direct one or more elements of the manual packaging station 14 to provide filling instructions to an employee 22 stationed at the manual packaging station 14, thereby causing the employee 22 to fill patient specific drug packages (e.g., the blister packs). The manual packaging station 14 is described in detail below, but further includes storage carousels 24 with canisters 26 of medications and indicator panels 28, a loading table 30, a staging bar 32 for holding canisters 26, at least one counter 34, a visual display monitor 36, a shutter assembly 38 at the loading table 30, and a tray 40 for holding blister packs at the shutter assembly 38. The manual packaging station 14 may be used as a primary packaging filling station, an alternative to the automated packaging station 16 to fill all of the blister packs in an order, as a supplemental station to fill only those blister packs requiring manual attention or filling (e.g., medications not automatically dispensable from cassettes, for example), or as a verification station for post-processing quality assurance following filling at the automated packaging station 16 or another manual packaging station 14.

Similarly, the automated packaging station 16 includes a machine controller 42 operatively connected to the controller 12 via network 20. The machine controller 42 of the automated packaging station 16 is configured to execute program code configured to operate filling machinery, such as a first robot 44 and a second robot 46 at a turntable assembly 48, to fill patient specific drug packages (e.g., the blister packs). The automated packaging station 16 and the operation thereof are described in detail in commonly-owned U.S. patent application Ser. No. 13/529,554 to Carson et al., the disclosure of which is hereby incorporated by reference in its entirety. In brief summary, the first robot 44 is configured to move cassettes containing medications to and from the turntable assembly 48 from storage carousels (similar to those carousels 24 shown in FIG. 1 at the manual packaging station 14). The turntable assembly 48 receives empty blister packs from magazines and rotates them past a plurality of stations, including a feeder base (not shown) that simultaneously actuates any combination of cassettes thereon to dispense the medications into the appropriate blister packs. The turntable assembly 48 may then rotate the blister packs through additional stations (not shown) such as alternative loading stations, fill and product verification stations which use optics or laser spectroscopy to verify the filling, and a printing station configured to print and apply covers to the bodies of the blister packs. The second robot 46 is stationed to remove filled and covered blister packs and place them into trays 40 substantially similar to those discussed above. The trays 40 may then be moved to downstream processing and shipping or to a manual packaging station 14 for further verification, should that additional verification be required. This process of verification is described in further detail below. The combined use of both the manual packaging station 14 and the automated packaging station 16 in the drug packaging system 10 provides efficient and accurate filling and verification of trays of blister packs to be delivered to a patient.

The controller 12 is shown in further detail in FIG. 1. To this end, controller 12 includes processor 60, memory 62, and I/O interface 64. Controller 12 further includes data structure 66 and operating system 68 resident in memory 62, where operating system 68 may further include one or more applications 70 configured to execute within operating system 68. In this regard, one of the applications 70 executed by the controller 12 is programmed to convert a list of prescribed medications and dosage instructions for a patient into filling instructions that explain how to fill the up to 120 blister packs at the manual packaging station 14, at the automated packaging station 16, or at both stations 14, 16. It will be appreciated that the machine controllers 18 and 42 may also include configurations similar to the configuration described above for controller 12. Input devices 72 may be operatively connected to controllers 12, 18, 42, for inputting data and/or prescriptions into the drug packaging system 10. Input devices 72 include, for example, a keyboard, a computer mouse, a barcode scanner, an optical scanner, electronic file or data transfer mechanisms, and other known scanning or input mechanisms. In addition, controller 12 includes local storage 74, which may also be operatively connected to machine controllers 18, 42.

Furthermore, drug packaging system 10 may be operatively connected to one or more resources over network 20, such as external resources 80 and/or remote terminals 82. External resources 80 may include data systems configured to communicate and interface with drug packaging system 10. For example, external resources 80 may include a drug information database, and an external system may be configured to receive a query from drug packaging system 10 corresponding to one or more drug types, the external resources 80 being configured to process the received query and transmit data related to the one or more drug types to drug packaging system 10. In addition, remote terminals 82 may be configured to transmit data to and receive data from drug packaging system 10. For example, remote terminals 82 may be configured to receive input from one or more users and transmit the input data to drug packaging system 10.

The routines executed to implement the embodiments of the invention, whether implemented as part of an operating system 68 or a specific application 70, component, program, object, module or sequence of operations executed by one or more specific or general purpose controllers of the control system will be referred to herein as "computer program code" or simply "program code." For example, referring to FIG. 1, the computer program code typically comprises one or more instructions that are resident at various times in various memory 62 and/or storage devices operatively connected to controllers 12, 18, 42 of the drug packaging system 10, and that, when executed by one or more processors 60 of the controllers 12, 18, 42 of the drug packaging system 10, may cause the controllers 12, 18, 42 to perform the steps necessary to execute steps, elements, and/or blocks embodying the various aspects of the invention. In addition, those skilled in the art will recognize that embodiments of the invention are not limited to particular types or configurations of processors or memory and/or storage devices.

Figure 2A:
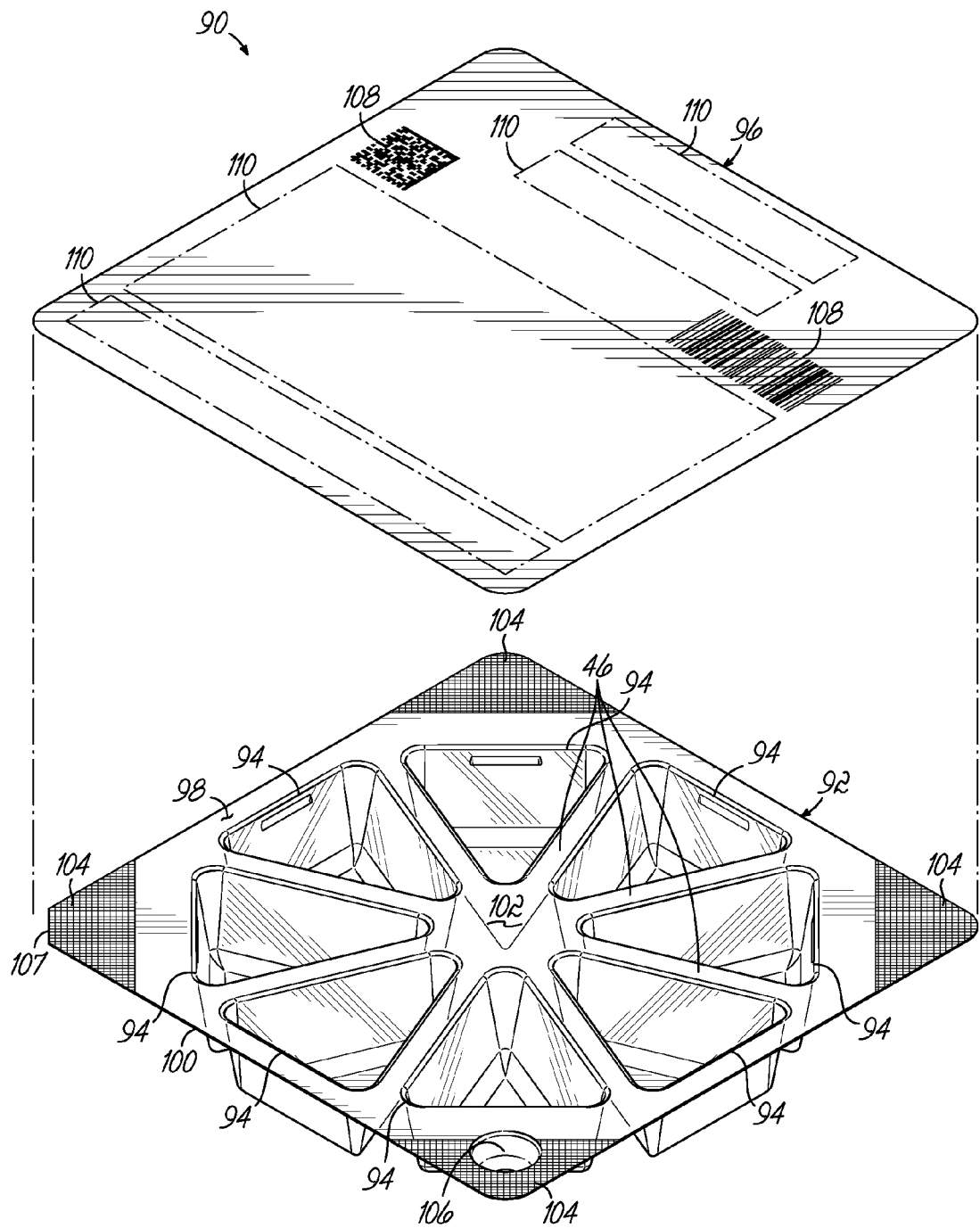
FIG. 2A is a partially exploded perspective view of one embodiment of medication packaging filled by the drug packaging system of FIG. 1.
Figure 3:
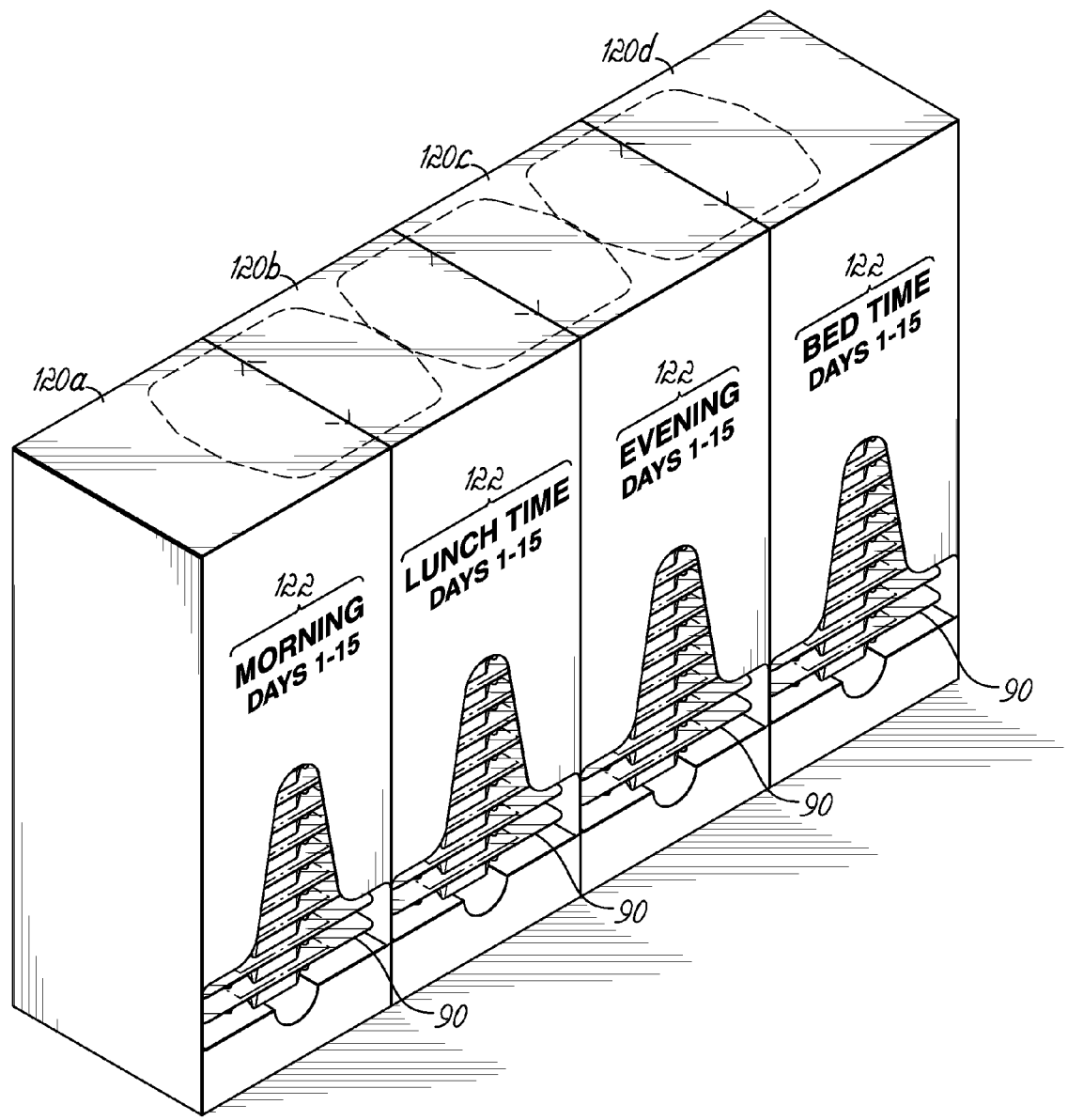
FIG. 3 is a perspective view of a set of cartons containing the medication packaging of FIG. 2A after a filling process.

Before describing the particular details of the manual packaging station 14 and its operation, it will be advantageous to describe the particular types of medication packaging designed for use with the drug packaging system 10. In this regard, one embodiment of a blister pack 90 used in the filling process is shown in FIGS. 2A and 3. The blister pack 90 may be the medication packaging described in detail in commonly-owned U.S. patent application Ser. No. 13/153,900 to Carson et al., the disclosure of which is hereby incorporated by reference in its entirety. To this end, the blister pack 90 includes a body 92 with a plurality of compartments 94 and a lidding sheet in the form of a cover 96. The cover 96 is joined to the body 92 in order to seal closed the compartments 94. In the representative embodiment, the number of compartments 94 is eight, but the total number of compartments 94 may be modified in other embodiments. Each of the compartments 94 is configured to receive and hold a unit dose or a portion of a unit dose of a medication. For example, the compartments 94 may be configured to receive one tablet, a partial or half tablet, multiple tablets, or a dose in a smaller blister package. After the medications are placed into the compartments 94 and the cover 96 is attached to the body 92, the blister pack 90 is thus sealed to prevent the ingress of environmental contaminants and then is in a state prepared for subsequent distribution to a patient.

Figure 2B:
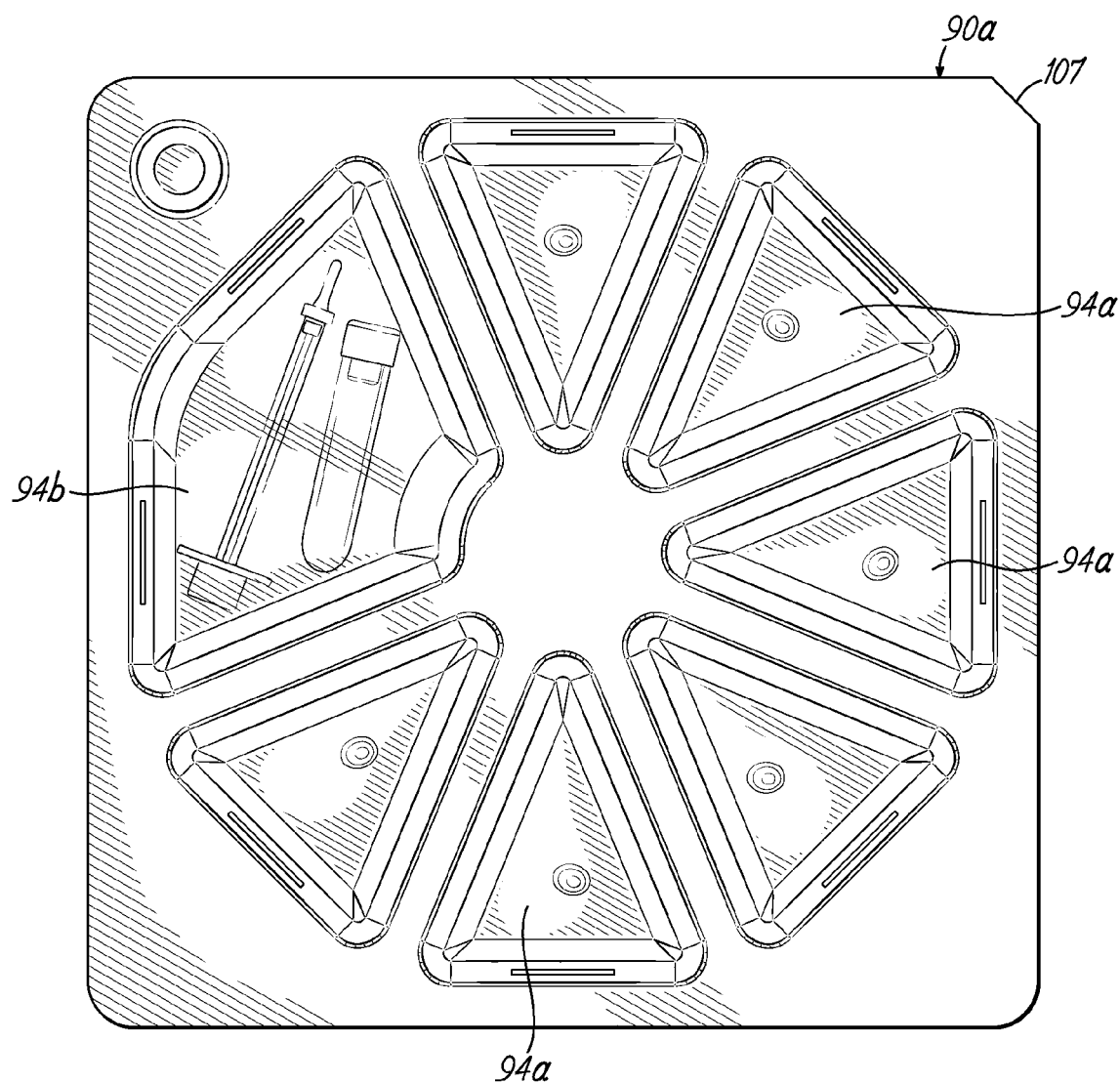
FIG. 2B is a bottom view of another embodiment of a medication packaging filled by the drug packaging system of FIG. 1.
Figure 2C:
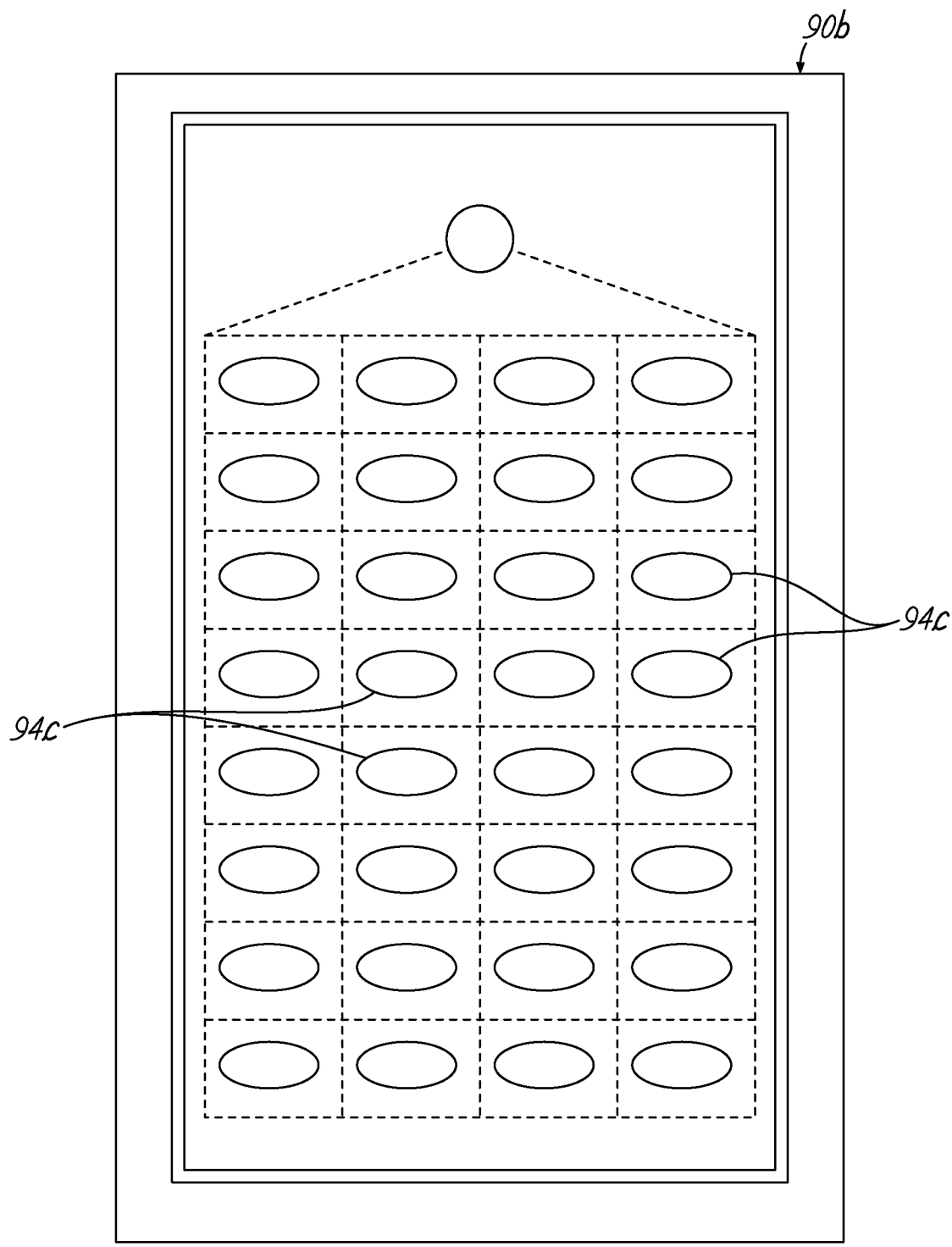
FIG. 2C is a top view of another embodiment of a medication packaging filled by the drug packaging system of FIG. 1.

As described above, the number of compartments 94 in the blister pack 90 and the blister pack design itself may be modified in other embodiments of the drug packaging system 10. Two examples of such modified packagings 90a, 90b are shown in FIGS. 2B and 2C. FIG. 2B illustrates an alternative blister pack 90a having a similar general shape as the blister pack 90 shown in FIG. 2A, but two of the wedge-shaped compartments 94a for holding a unit dose have been replaced and combined into one larger (and possibly deeper), elongate compartment 94b. As schematically shown in FIG. 2B, this larger compartment 94b is configured to hold larger items such as vials of medication or injectable medications. This blister pack 90a may be filled using the equipment of the manual packaging station 14 described in full detail below without significant modifications to that equipment. FIG. 2C illustrates an alternative blister card 90b configured to receive a two-dimensional matrix or grid of unit doses of a particular medication for a month (or some other time period within the month). To this end, the blister card 90b includes about 30 individual blister compartments 94c configured to receive daily doses of a particular medication. A similar type of packaging to this blister card 90b is described in commonly-owned U.S. Pat. No. 7,328,801 to Iossi, the disclosure of which is hereby incorporated by reference in its entirety. It will be understood that the equipment of the below-described manual packaging station 14 would require some modification to accommodate the blister cards 90b, but the principles of filling operation would remain the same.

Returning to the embodiment shown in FIG. 2A, the body 92 includes a top surface 98 that surrounds each of the compartments 94 and extends to an outer periphery 100 of the body 92. The compartments 94 of the illustrated embodiment are formed as triangular or wedge-shaped cavities extending downwardly from the top surface 98 and arranged about a central region 102 of the top surface 98. The top surface 98 may include corner regions 104 modified with a pattern of surface-area reducing features that consist of non-planar structures formed into the material of the body 92. These features at the corner regions 104 assist a patient with easy removal of the cover 96 after delivery of the filled blister pack 90 to the patient. The top surface 98 is free of score lines, lines of weakening, perforated seams, and the like. This structural omission is permitted because the individual compartments 94 are not intended to be severed from the body 92.

The body 92 of the blister pack 90 also includes an indexing feature 106 in the representative form of a blind, hollow post that is disposed in the vicinity of one of the corner regions 104 in the representative embodiment. The indexing feature 106 projects away from the plane of top surface 98 in the same direction as the compartments 94. The indexing feature 106 may be utilized to rotationally orient the body 92, for example, relative to the tray 40 or relative to the turntable assembly 48 previously described. In this manner, the angular orientation of multiple different blister packs 90 can be reproducibly established for positioning the compartments 94 at known and fixed positions during a filling operation. In addition, another of the corner regions 104 adjacent to the corner region 104 with the indexing feature 106 further includes a notch 107 cut away from the corner region 104. This notch 107 is used to verify the orientation of the blister pack 90 upon manual entry into packaging magazines (not shown) of the automated packaging station 16. The notch 107 is oriented as a generally parallel cut to the outermost wall of the closest compartment 94.

The cover 96 is adapted to be heat sealed or otherwise adhered to the body 92 after the filling process. The cover 96 is a thin sheet of material including machine readable indicia 108 that may be scanned after the filling process. Although two different machine readable indicia 108 are shown on the cover 96, it will be understood that more or fewer of these indicia 108 may be printed on the cover 96 in other embodiments consistent with the invention. The cover 96 may also include human readable labels 110 containing information on the medications contained within the blister pack 90 and the intended patient. The machine readable indicia 108 and human readable labels 110 may be printed on the cover 96 prior to adherence of the cover 96 to the body 92. More specifically, the covers 96 may be printed with any known type of machine readable indicia 108 (e.g., barcodes, OCR, OVR) and any type of human readable labels 110 by a station configured to print and apply these labels in series immediately after the blister pack 90 are filled and verified. As will be described in further detail below, this station operates to print only partial or different indicia 108 and labels 110 in the event of an error detected during verification, thereby prompting operators to address these errors manually during downstream processing.

As briefly described above, the blister packs 90 are best suited for distributing medications that are administered to a patient on a regular or irregular dosage interval as part of long-term, maintenance care. Each of the medications may be administered to the patient by oral or other consumption once a day (QD), two times a day (BID), three times a day (TID), four times a day (QID), or on irregular or different intervals (e.g., once per day on Mondays, Wednesdays, and Fridays). Certain oral medications should be administered to the patient by oral consumption during a specific medication pass (such as only at bed time or morning). The dosage interval for each medication and any time-of-day restrictions, personal administration time preferences, and/or drug contra-indications may be factors used to allocate the medications to a specific blister pack 90 designated for administration in a particular medication pass. The consideration of each of these factors in determining how a month-long (i.e., 30-day) supply of blister packs 90 or medication passes should be filled is described in further detail below. Once the medications have been allocated to the appropriate blister packs 90 for a 30-day period (hereinafter referred to generally as a "month"), then the filling process described in further detail below may be conducted at the manual packaging station 14 to fill each of the blister packs 90 for that month. It will be understood that the "month" may begin on any day of a calendar week or month depending on when the medications are being filled and delivered to a particular patient, and it will also be understood that the term "month" could also refer to a 28-day period, a 31-day period, etc. in other embodiments.

With reference to FIG. 3, filled blister packs 90 may be distributed in a set of multiple cartons 120a, 120b, 120c, 120d for delivery to the residence of the patient. Each of the cartons 120a, 120b, 120c, 120d may initially contain or house up to a month's supply of blister packs 90 containing medication passes intended to be administered to the patient at nominally the same designated time on successive days of a month as identified by indicia 122 on the cartons or the human readable labels 110 on the covers 96 of the blister packs 90. In the illustrated example, the cartons 120a, 120b, 120c, 120d may contain respective stacks of blister packs 90 sufficient to provide a half-month supply (in the exemplary embodiment) of medications for administration at four different daily times each day in a given month. However, each of the cartons 120a, 120b, 120c, 120d may be reconfigured and resized to provide a full month supply of medications for administration at the four times each day. It will be appreciated that the cartons 120a, 120b, 120c, 120d may be reconfigured as a single package or any number of different packages corresponding to subsets of the blister packs 90 to be delivered to the patient as a supply of medicament, whether used during schedule medication passes or for PRN purposes. It will also be understood that the end consumer or patient may obtain blister packs 90 from the cartons 120a, 120b, 120c, 120d either manually or by loading the cartons 120a, 120b, 120c, 120d into a mechanized, electronically controlled dispenser that controls distribution of the blister packs 90 automatically per the prescriptions.

In the foregoing and following description, reference is made generally to "oral medications." Each of the oral medications configured to fill the blister packs 90 may be any type of ingestible substance capable of being categorized as an oral medication. It will be understood that the use of the term "oral medications" does not limit the blister packs 90 to being filled with just orally consumed medications, as other types of medications applied in different manners may also be inserted in the filling process. The ingestible substance comprising each of the oral medications may include, but is not limited to, one or more pharmaceuticals, medicaments, one or more compositions, one or more drugs, one or more vitamins, one or more mineral supplements, and one or more placebos, either alone or in combination, and may be dispensed by prescription or over-the-counter. The medications may be provided in various dosage forms such as pills, tablets, capsules, vials, ampoules, gel capsules, solids, liquids, powders, etc. A "unit dose" in the context of this invention is an amount of the medication or solid product that is administered to a patient in a single dose.

Figure 4:
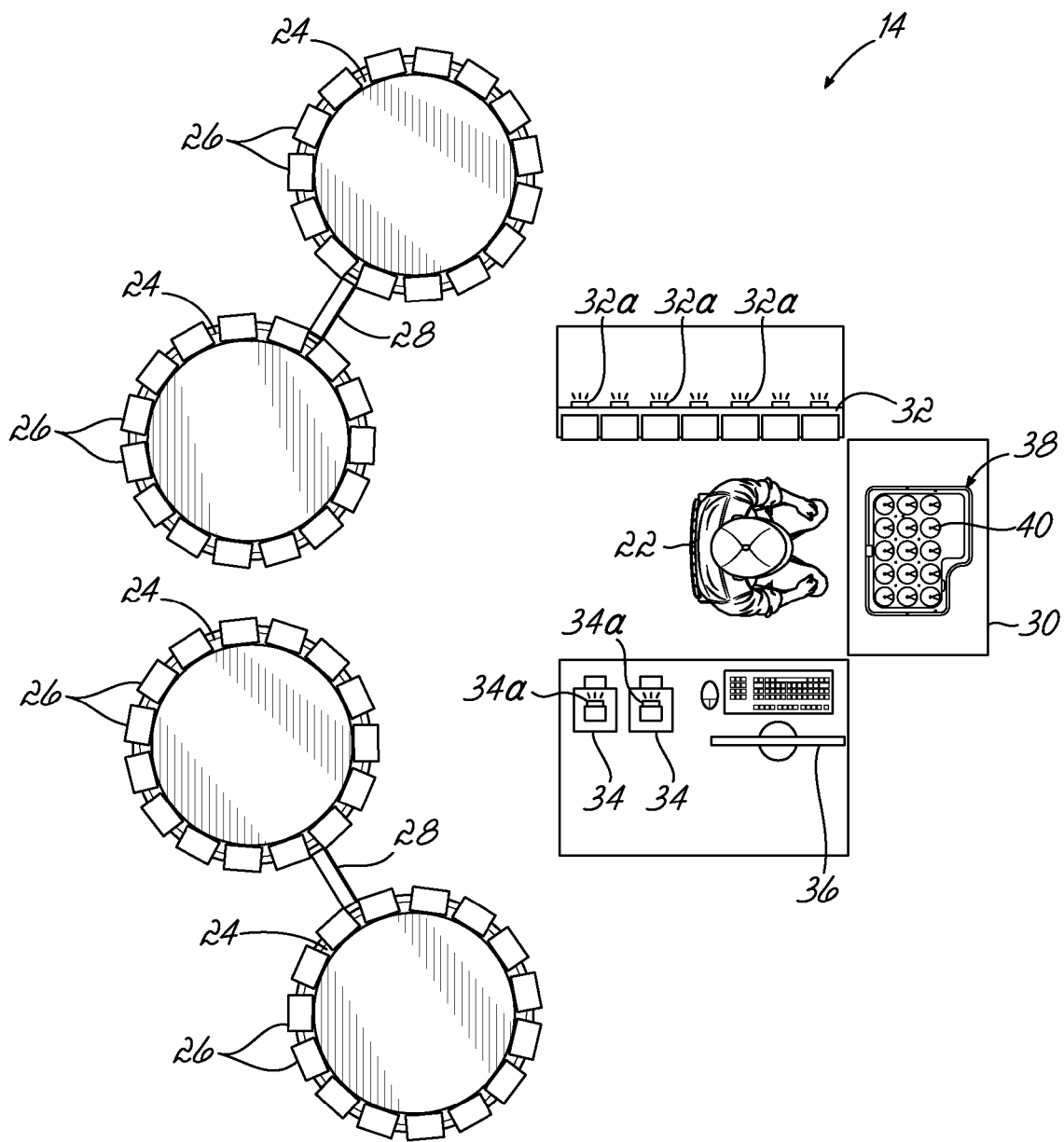
FIG. 4 is a top view of a manual packaging station in accordance with an embodiment of the invention.

Now with specific reference to FIGS. 4 through 14B, the manual packaging station 14 according to an exemplary embodiment of the current invention is shown in further detail. As shown in the illustration of the entire manual packaging station 14 at FIG. 4, the manual packaging station 14 includes the plurality of storage carousels 24, each adapted to hold various canisters 26 filled with different medications. One or more indicator panels 28, also known as light trees, are positioned adjacent the storage carousels 24. The operator 22 may read messages on the indicator panels 28 that instruct her as to where to pick up and drop off canisters 26 for movement to and from the staging bar 32, for later use of the medications at the loading table 30. The loading table 30 includes the shutter assembly 38 and an array of light emitting diodes (LEDs) (not shown in FIG. 4) below the shutter assembly 38. The shutter assembly 38 is configured to receive the tray 40 filled with various blister packs 90 or other medication packagings to be filled with the medications. For example, each tray 40 may hold fifteen blister packs 90 as shown in FIG. 4. As described in detail below, the shutter assembly 28 provides selective access to only one compartment 94 in each blister pack 90 at a time, thereby simplifying the filling or verification process for the operator 22.

The staging bar 32 holds a plurality of canisters 26 adjacent to the loading table 30 and the counters 34 so that each of the medications needed to fill the plurality of blister packs 90 in a particular tray 40 is readily available during the filling process. The staging bar 32 includes indicator lights 32a configured to indicate to the operator 22 where to place or remove canisters 26 during the batch picking process described below. Each of the counters 34 is configured to receive a particular canister 26 and to count/dispense a number of unit doses of the medication held therein based on an input command from the operator 22. The counters 34 may also include indicator lights 34a such as LEDs that indicate when to move canisters 26 to or from the counters 34. The visual display monitor 36 illustrates actions for the operator 22 to take during the filling process and also illustrates the status of the various elements of the manual packaging station 14. It will be understood that the actual layout of the storage carousels 24, the loading table 30, the staging bar 32, the counters 34, and the visual display monitor 36 may be modified from the schematic example shown in FIG. 4 without departing from the invention.

Figure 5:
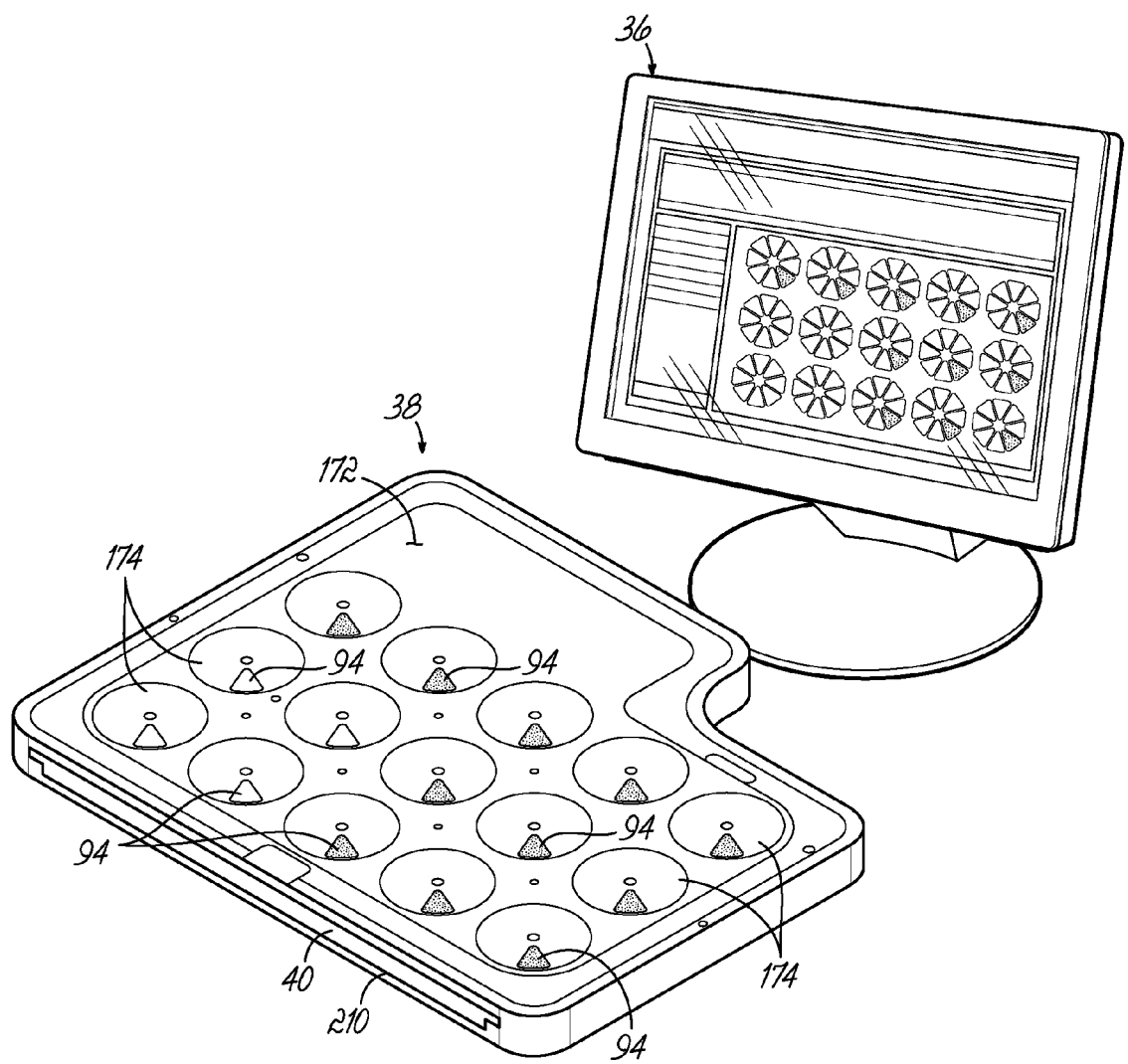
FIG. 5 is a top perspective view of a loading table and a shutter assembly used with the manual packaging station of FIG. 4.

Further details of the loading table 30 and the shutter assembly 38 and tray 40 used at the loading table 30 to fill a set of blister packs 90 are shown in FIGS. 5 through 14B. With reference to FIG. 5, the visual display monitor 36 is shown adjacent to the shutter assembly 38 instead of next to the loading table 30, although it will be understood that the particular placement of the visual display monitor 36 may be configured to best suit the operator 22. With the visual display monitor 36 in the position shown, FIG. 5 illustrates the correlation seen by an operator 22 during a filling or verification process of blister packs 90 located in a tray 40 within the shutter assembly 38. To this end, the shutter assembly 38 blocks access to all compartments 94 of the blister packs 90 except for one in each blister pack 90. In the circumstance where a unit dose of a certain medication must be positioned or verified in all fifteen of the open compartments 94, the LEDs light each of the compartments 94 from the bottom of the shutter assembly 38 as schematically shown. At the same time, these compartments 94 are also highlighted with a similar lighting or marking on the visual display monitor 36, which shows a layout of all of the blister packs 90 in the tray 40. If only a partial set of the compartments 94 were to be filled or verified by manual inspection, then only those compartments 94 would be lit up by the LEDs in the shutter assembly 38. Thus, the operator 22 can have confirmation on where to place or verify the placement of medications from multiple prompting sources, thereby reducing the likelihood for errors made in the filling and verification process. Once each of the blister packs 90 in the tray 40 have been filled or inspected as prompted at the visual display monitor 36, the operator 22 can remove the tray 40 and replace it with another tray 40 for filling or verification to continue the process.

With reference to FIGS. 6 through 8, the shutter assembly 38 includes a main body 170 as shown without a tray 40 inserted or a top plate 172 in position. Thus, FIG. 6 illustrates the various drive and control components of the shutter assembly 38. To this end, the shutter assembly 38 includes a plurality of shutter gears 174 disposed in a matrix within an outer periphery 176 defined by the main body 170. Each of the shutter gears 174 includes an outer toothed periphery 178, a central bearing shaft 180, and a triangular or wedge-shaped opening 182 located between the periphery 178 and the bearing shaft 180. The openings 182 are aligned with one another across all of the shutter gears 174 so as to provide access through the shutter gears 174 to a corresponding compartment 94 of respective blister packs 90 located underneath the shutter gears 174. In the exemplary embodiment of FIG. 6, fifteen total shutter gears 174 are provided, but it will be understood that the shutter assembly 38 may be reconfigured with any number of shutter gears 174 as required for trays 40 to be used in the shutter assembly 38. The shutter gear 174 is further described with reference to FIGS. 12A and 12B below.

Each of the shutter gears 174 are operatively coupled to each other by a plurality of idler gears 184. As shown in FIG. 6, each idler gear 184 is located between four adjacent shutter gears 174. Each idler gear 184 includes a central bearing shaft 186 and a toothed periphery 188 engaged with the toothed peripheries 178 of the adjacent four shutter gears 174. Consequently, as each shutter gear 174 rotates in unison in a first direction (e.g., clockwise), each idler gear 184 simultaneously rotates in a second direction (e.g., counterclockwise) opposite the first direction. The plurality of idler gears 184 therefore ensures that all shutter gears 174 remains in alignment with one another while transferring driving movement from a single shutter gear 174 to all other shutter gears 174. The idler gear 184 is further described with reference to FIGS. 14A and 14B below.

As noted above, one of the shutter gears 174 is driven by engagement with a drive gear 190. The drive gear 190 includes a toothed periphery 192 engaged with the toothed periphery 178 of the shutter gear 174 and an output 194 of a stepper motor 196. Thus, the stepper motor 196 is configured to actuate simultaneous rotational movement of all shutter gears 174. The drive gear 190 is also engaged with a placement gear 198 along respective toothed peripheries 192, 200. As will be readily understood, the drive gear 190 and the placement gear 198 are each centered on central bearing shafts 202 analogous to the bearing shafts 180, 186 of the shutter gears 174 and the idler gears 184. The placement gear 198 also includes a plurality of sensor apertures 204 arranged in radial rows extending from the bearing shaft 202 to the toothed periphery 200. The number of radial rows of sensor apertures 204 is equivalent to the number of rotational positions of the shutter gears 174 and the number of compartments 94 in each blister pack 90 to be filled at the shutter assembly 38. The sensor apertures 204 may rotate through an optical sensor (not shown) of a controller box 206 positioned proximate to the shutter gears 174 and the stepper motor 196 within the shutter assembly 38. In this regard, the position of the shutter gears 174 may be sensed and/or controlled by the stepper motor 196 dependent upon detection of the sensor apertures 204. The placement gear 198 is further described with reference to FIGS. 13A and 13B below.

With reference to FIGS. 7 and 8, the main body 170 of the shutter assembly 38 also includes a top opening 208 (described in further detail with reference to FIG. 11 below) adapted to receive the top plate 172 and a tray slot 210 which opens at one side of the main body 170. The tray slot 210 is sized and shaped to receive a tray 40 (described briefly above and in further detail with reference to FIGS. 9 and 10 below) In addition to the previously-described connections to the stepper motor 196 and the placement gear 198, the controller box 206 may also include additional sensors for detecting the presence of a tray 40 and the identity of the tray 40. For example, the controller box 206 may include a push switch 212 configured to be actuated whenever a tray 40 is fully inserted into the tray slot 210 of the shutter assembly 38. Then a separate identification scanner such as a bar code reader 214 (schematically shown in FIG. 6) in the shutter assembly 38 may be used to verify the identity of the particular tray 40 inserted by scanning the unique barcode located on the tray 40. Identifying the tray 40 inserted allows the controller box 206 to communicate with the filling software described in detail below to determine which medications need to be used to fill the blister packs 90 in the tray 40. It will be understood that additional or different types of sensors may be used in other embodiments of the shutter assembly 38, and also that the sensors 212, 214 shown may be relocated depending upon the particular size and configuration of the tray 40 (e.g., to match where the barcode is located on the tray 40).

More specifically, a new tray 40 of empty blister packs 90 may be inserted into the shutter assembly 38 through insertion into the tray slot 210. Once the tray 40 actuates the push switch 212 and the barcode on the tray 40 is scanned with the barcode scanner 214, the shutter assembly 38 may lock the tray 40 in the tray slot 210 until all necessary filling or verification steps have been completed. This locking step may be performed by one or more locking members 216 in the form of blocking pegs that may block movement of the tray 40 out of the tray slot 210 until removal is approved by the machine controller 18. These locking members 216 may be actuated and released by any known mechanism operatively connected to the controller 18. The previously-mentioned assembly of LEDs 218 is also schematically shown in FIG. 8 and is arranged within the main body 170 of the shutter assembly 38 and below the tray slot 210. There may be more than one LED 218 for each compartment 94 of a blister pack 90 or shared LEDs 218 for multiple compartments 94 depending on the particular layout required by the end user of the shutter assembly 38.

An exemplary embodiment of the tray 40 used with the shutter assembly 38 is shown in FIGS. 9 and 10. The tray 40 includes a central portion 220 having a plurality of sets of cavities 222 adapted to receive the compartments 94 of multiple blister packs 90 to be filled at the shutter assembly 38. Additionally, the central portion 220 also includes an indexing cavity 224 located adjacent to each set of cavities 222, the indexing cavity 224 configured to receive the indexing feature 106 of a blister pack 90. Thus, when a plurality of blister packs 90 are loaded into the tray 40 with the top surface 98 of the body 92 facing upwardly, each blister pack 90 is oriented similarly to other blister packs 90 by virtue of the engagement of the indexing features 106 with the indexing cavities 224. An exemplary blister pack 90 is shown in position in the tray 40 in phantom in FIG. 9. The sets of cavities 222 and the indexing cavities 224 are deep enough to fully receive the corresponding compartments 94 and indexing features 106 of the blister packs 90, such that the top surfaces 98 reside adjacent to a top 226 of the central portion 114.

The tray 40 also includes a pair of alignment rails 228 extending from opposing sides of the central portion 220 adjacent a bottom 230 of the central portion 220. The alignment rails 228 are configured to slide within the tray slot 210 of the shutter assembly 38 to securely hold the tray 40 in position in the shutter assembly 38. The alignment rails 228 do not extend along the entire length of the opposing sides. The central portion 220 may also include a tray indexing feature 232 such as a corner aperture configured to be detected by a sensor of the shutter assembly 38 to ensure proper orientation of the tray 40 within the tray slot 210. The central portion 220 may also include one or more through-bores 234 that may be countersunk as shown in FIG. 10. The through-bores 234 may be used for alignment purposes or for locking purposes, as well understood. The tray 40 may also be used to collect blister packs 90 filled at the automated packaging machine 16, and each tray 40 is configured to collate and hold portions of orders for a patient until final packaging into cartons 120*a*, 120*b*, 120*c*, 120*d* or other outer packages.

Figure 11:
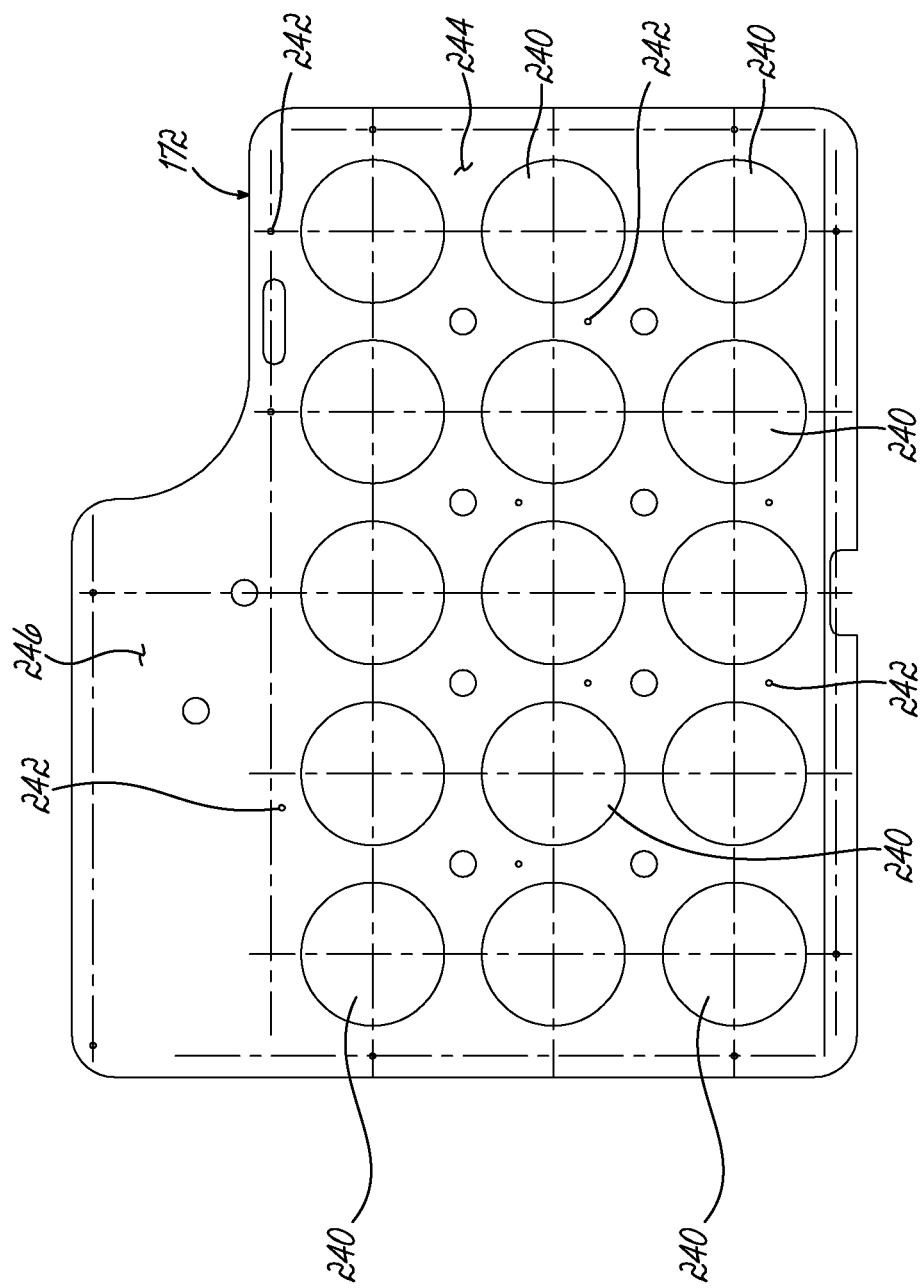
FIG. 11 is a top view of a cover plate used with the shutter assembly of FIG. 6.

With reference to FIG. 11, one embodiment of a top plate 172 of the shutter assembly 38 is shown. The top plate 172 is shaped to sit within the top opening 208 of the main body 170 of the shutter assembly 38. The top plate 172 covers the majority of the operating components within the shutter assembly 38 to protect an operator 22 from the moving components. The top plate 172 includes a plurality of shutter apertures 240 adapted to provide access to the shutter gears 174 and more particularly, to the openings 182 in the shutter gears 174. Regardless of the position of the shutter gears 174, the operator 22 will have access to the same compartment 94 of each blister pack 90 in the tray 40 through the shutter apertures 240 and the openings 182. The top plate 172 also includes a plurality of fastener apertures 242 positioned around the plurality of shutter apertures 240. Similarly, the main body 170 of the shutter assembly 38 also includes corresponding fastener apertures 244 configured to be aligned with the fastener apertures 242 in the top plate 172. As will be readily understood, conventional fasteners may be used in these fastener apertures 242, 244 to retain the top plate 172 in position at the top opening 208 of the main body 170. The top plate 172 includes a primary portion 244 configured to block access to the tray 40 within the tray slot 210 and a projecting portion 246 configured to block access to the drive components such as the drive gear 190, the motor 196, and the controller box 206, thereby matching the shape of the main body 170 of the shutter assembly 38.

Figure 12B:
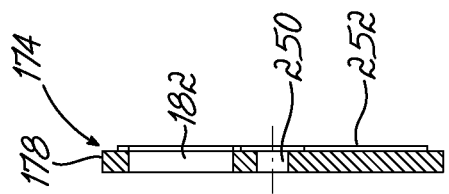
FIG. 12B is a side view of the shutter gear of FIG. 12A.
Figure 12A:
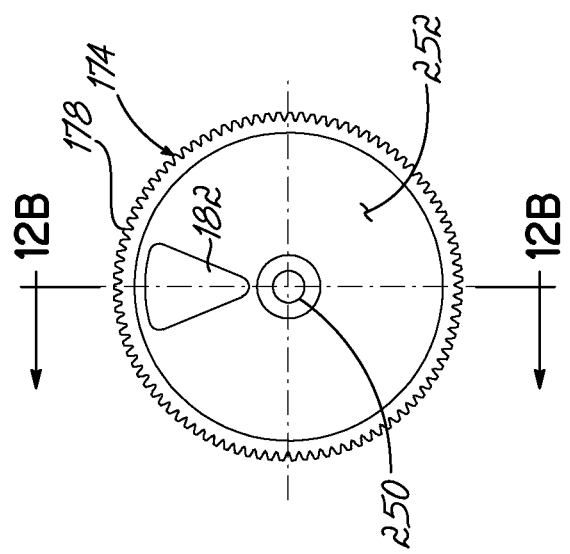
FIG. 12A is a top view of a shutter gear of the shutter assembly of FIG. 6.

With reference to FIGS. 12A and 12B, one of the shutter gears 174 located in the shutter assembly 38 includes the toothed periphery 178 and a central opening 250 for the bearing shaft 180 previously described. The shutter gear 174 also includes the opening 182 configured to provide access to one of the compartments 94 of a blister pack 90. As most clearly shown in FIG. 12B, the toothed periphery 178 of the shutter gear 174 is recessed slightly from a top face 252 of the shutter gear 174. This spacing from the top face 252 prevents the toothed periphery 178 from abutting and rubbing against the top cover 172 when inserted into the main body 170 of the shutter assembly 38. It will be appreciated that the wedge-shaped opening 182 may be resized or reshaped in other embodiments. For example, when the modified blister pack 90*a* shown in FIG. 2B is used with the shutter assembly 38, the wedge-shaped opening 182 may be made larger to accommodate larger items going into larger combined compartments.

Figure 13B:
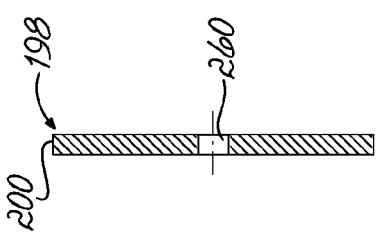
FIG. 13B is a side view of the placement gear of FIG. 13A.
Figure 13A:
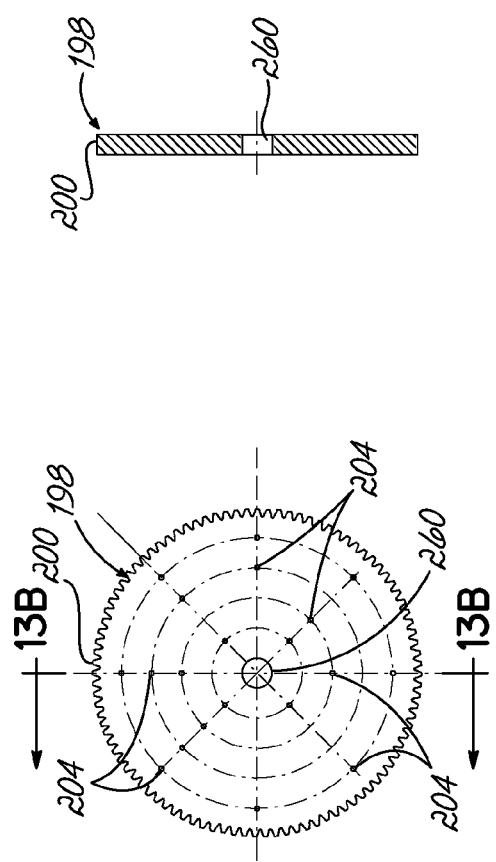
FIG. 13A is a top view of a placement gear of the shutter assembly of FIG. 6.

With reference to FIGS. 13A and 13B, the placement gear 198 located in the shutter assembly 38 includes the toothed periphery 200 and a central opening 260 for the bearing shaft 202 previously described. The placement gear 198 also includes the sensor apertures 204 configured to be detected by the optical sensor of the controller box 206 to thereby communicate the rotational position of the placement gear 198 and the corresponding shutter gears 174. As most clearly shown in FIG. 13B, the placement gear 198 is substantially plate-shaped. It will be understood that the placement gear 198 is similarly sized as the shutter gears 174 such that the placement gear 198 and the shutter gears 174 have the same gear ratio with respect to the drive gear 190 and therefore the same rotational speed. However, the placement gear 198 and the positioning and number of the sensor apertures 204 may be modified to be different in other embodiments, with the sensor apertures 204 still corresponding to movements of the opening 182 in the shutter gears 174.

Figure 14B:
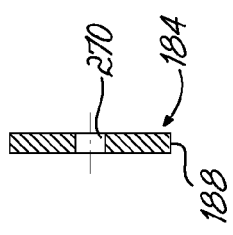
FIG. 14B is a side view of the idler gear of FIG. 14A.
Figure 14A:
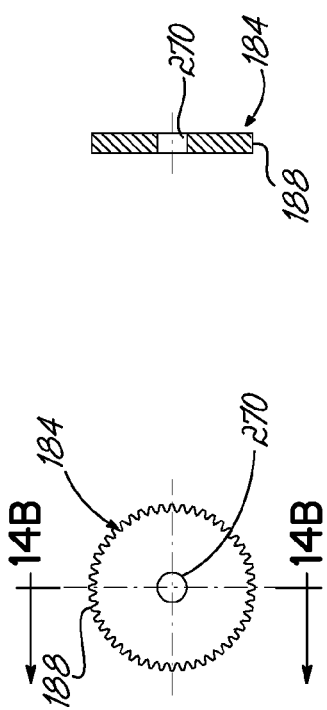
FIG. 14A is a top view of an idler gear of the shutter assembly of FIG. 6.

With reference to FIGS. 14A and 14B, one of the idler gears 184 located in the shutter assembly 38 includes the toothed periphery 188 and a central opening 270 for the bearing shaft 186 previously described. As most clearly shown in FIG. 14B, the idler gear 184 is substantially plate-shaped. Each of the idler gears 184 is smaller in dimension than the shutter gears 174, but the same gear ratio is maintained by keeping each idler gear 184 identical in size and each shutter gear 174 identical in size. The rotation of the shutter gear 174 connected to the drive gear 190 is transmitted by opposite-direction rotation of the idler gears 184 throughout the matrix of shutter gears 174. This enables accurate and uniform placement of the openings 182 in each of the shutter gears 174 so that the same compartment 94 of the blister packs 90 is open for access to the operator 22 simultaneously.

As noted above, the shutter assembly 38 and the tray 40 may be reconfigured for any particular type and any particular number of blister packs 90. The exemplary embodiment is configured to permit filling of fifteen blister packs 90 at once, which balances the convenience of filling more blister packs 90 per tray against reasonable size limitations of the manual packaging station 14 and the shutter assembly 38. It will be understood that the shutter assembly 38, and more particularly the shutter gears 174, may be used in other filling operations not described in detail herein. To this end, the shutter gears 174 may be used in a filling process for different medicament containers such as bottles or vials, and may also be used in filling applications where the items being loaded into containers are not medications. Moreover, the shutter gears 174 may be reconfigured as rotatable shutter plates without the toothed periphery 178 in other embodiments where the shutter mechanism for each blister pack 90 is to be driven separately. In another example, the shutter assembly 38 may replace the rotatable shutter gears 174 with independently actuated shutter doors arranged in a matrix to fit blister packs of different configurations, such as the blister card 90*b* having a matrix of compartments 94*c* described above with reference to FIG. 2C, in other embodiments consistent with the invention. Consequently, the rotatable shutters or other shutter mechanisms may be used in various filling operations.

Furthermore, the shutter assembly 38 may be used during a verification process of blister packs 90 filled at an automated packaging station 16 or another manual packaging station 14. In this regard, a certain percentage of trays 40 may be flagged for manual verification or a number of blister packs 90 may be flagged for independent verification due to an error sensed during the filling process. Regardless of the reasoning for requiring verification, the tray 40 may be inserted into the shutter assembly 38 as described above. If any covers 96 need to be removed to provide access to the compartments 94, these covers 96 are peeled off prior to insertion of the tray 40 into the tray slot 210. The shutter assembly 38 then operates to rotate the shutter gears 174 and illuminate the LEDs 218 to indicate which compartments 94 require manual verification and which medications should be located in those compartments 94 will be shown on the visual display monitor 36. The verifying operator 22 can then verify that the correct medication is located in the correct compartments 94, or take corrective action if such corrective action is required. Once each of the flagged compartments 94 has been verified by the operator 22, the tray 40 may be removed from the shutter assembly 38 and additional covers 96 may be printed and applied to the blister packs 90 that had no covers 96 or the covers 96 removed for verification. Consequently, the shutter assembly 38 and the manual packaging station 14 provide additional uses beyond just the filling process.

To this end, the previously-described arrangement of elements within the manual packaging station 14 allows an operator 22 to fill a plurality of blister packs 90 with medications prescribed to a patient or verify that previously-filled blister packs 90 have been correctly filled with medications for the intended patient. The filling process enables high speed and accuracy for a manual process. By preventing access to the majority of the compartments, the operator 22 is guided to fill or verify only those compartments 94 of the blister packs 90 that require attention immediately. This reduces the likelihood of inserting a medication into the wrong compartment 94 or verifying the wrong compartment 94 during a verification process. Moreover, the operators 22 can fill or verify an entire 15 day supply of blister packs 90 or 15 PRN blister packs 90 at once in the shutter assembly 38, which enables the operator 22 to only perform exchanges of trays 40 at the same time that new batches of canisters 26 need to be picked from the storage carousels 24. Especially when used in combination with one or more automated packaging stations 16 in the drug packaging system 10, the manual packaging station 14 enables high quality and accuracy to be achieved with minimized time used per blister pack 90. The methods and processes implemented by the drug packaging system 10 and by the manual packaging station 14 are described in greater detail below with reference to a number of operational flowcharts shown in the figures. Except when otherwise discussed, the following methods and processes are implemented by the exemplary embodiment of the drug packaging system 10 as described in detail above.

In this regard, some embodiments of the invention may include systems and methods for dynamically sorting one or more prescriptions into a patient specific pharmacy order. The patient specific pharmacy order may include one or more patient specific drug packages to be filled with one or more drugs indicated by the one or more drug prescriptions. In some embodiments consistent with the invention, each prescription may be analyzed, and packaging instructions corresponding to the appropriate dosage of each drug to be placed in each patient specific drug package (e.g., the blister packs 90) of the patient specific pharmacy order may be generated. For example, the patient specific drug package may correspond to a time of day the patient should take the drug including morning, lunchtime, evening, bedtime, etc. In addition, the patient specific drug package may correspond to a particular day of the week, or a specific date (e.g. Jan. 1, 2012), such that the analysis and dynamic sorting may generate packaging instructions corresponding to one or more patient specific drug packages that may be specific to a time of day, day of the week, and/or a specific calendar date.

In these embodiments, one or more prescriptions of a drug prescription order may be loaded, and each prescription may include prescription data which may indicate the patient and/or a unique patient identifier, the drug type, dosage amount, the dosing instructions, and/or patient dosage or administration time preferences. In some embodiments, the one or more loaded prescriptions may be analyzed to determine the patient associated with each loaded prescription, the drug type of each prescription, the dosage amount of each prescription, and/or the dosing instructions for each prescription.

In some embodiments, analyzing the prescription data of each prescription associated with a patient prescription group may include analyzing the indicated drug type of each prescription associated with a patient prescription group to determine drug contra-indications for one or more prescriptions associated with the patient prescription group. Moreover, generating patient specific drug packaging data for the patient associated with the patient prescription group may be based, at least in part, on the determined drug contra-indications.

In some embodiments, analyzing the prescription data of each prescription associated with a patient prescription group may include analyzing the indicated dosage amount of each prescription associated with a patient prescription group to determine the prescribed dosage amount of each prescription associated with the patient prescription group. Furthermore, generating patient specific drug packaging data for the patient associated with the patient prescription group may be based, at least in part, on the determined prescribed dosage amount of each prescription.

In some embodiments, analyzing the prescription data of each prescription associated with a patient prescription group may include analyzing the indicated dosing instructions of each prescription associated with a patient prescription group to determine the prescribed dosing instructions of each prescription associated with the patient prescription group. In addition, generating patient specific drug packaging data for the patient associated with the analyzed patient prescription group may be based, at least in part, on the determined prescribed dosage amount of each prescription.

In some embodiments, analyzing the prescription data of each prescription associated with a patient prescription group may include analyzing the indicated patient administration time preferences of each prescription associated with a patient prescription group to determine the patient preferences regarding one or more prescriptions of the patient prescription group. Furthermore, generating patient specific drug packaging data for the patient associated with the patient prescription group may be based, at least in part, on the indicated patient administration time preferences of each prescription.

In some embodiments, packaging instructions corresponding to each patient specific drug package of a patient specific pharmacy order may be generated based, at least in part, on the patient specific packaging data. The packaging instructions may also be referred to as filling instructions herein. In some embodiments, the packaging instructions may include program code executable by a control system of a drug packaging system such that the control system may direct an operator or machinery to distribute prescribed dosages of one or more drugs into one or more patient specific drug packages, such that a patient specific pharmacy order may be filled. In some embodiments, the packaging instructions may correspond to a manual packaging station 14. In other embodiments, the packaging instructions may correspond to an automated packaging station 16. As such, in some embodiments, the generated packaging instructions may be based, at least in part, on the type of packaging station 14, 16 that may be packaging the patient specific drug packages of the patient specific pharmacy order.

FIGS. 15 through 32B provide sequences of operations that may be performed by some embodiments consistent with the invention. Moreover, embodiments of the invention provided as sequences of operations for example, in FIGS. 15 through 32B, may be embodied in program code resident in various memory 62 and/or storage devices 74 and may be configured to be executed by one or more processors 60 of a drug packaging system 10 consistent with some embodiments of the system. In addition, while the invention has been illustrated by a description of various embodiments and while these embodiments have been described in considerable detail, the applicant does not intend to restrict or in any way limit the scope of the appended claims to such detail. For example, the blocks of any of the flowcharts may be re-ordered, processed serially and/or processed concurrently without departing from the scope of the invention. Moreover, any of the flowcharts may include more or fewer blocks than those illustrated consistent with embodiments of the invention.

While the invention has and hereinafter will be described in the context of fully functioning systems, those skilled in the art will appreciate that the various embodiments of the invention are capable of being distributed as a program product in a variety of forms, and that the invention applies equally regardless of the particular type of computer readable media used to actually carry out the distribution. Examples of computer readable media include, for example, non-transitory recordable type media such as volatile and nonvolatile memory devices, floppy and other removable disks, hard disk drives, USB drives, optical disks (e.g. CD-ROM's, DVD's, Blu-Ray discs, etc.), among others.

Figure 15:
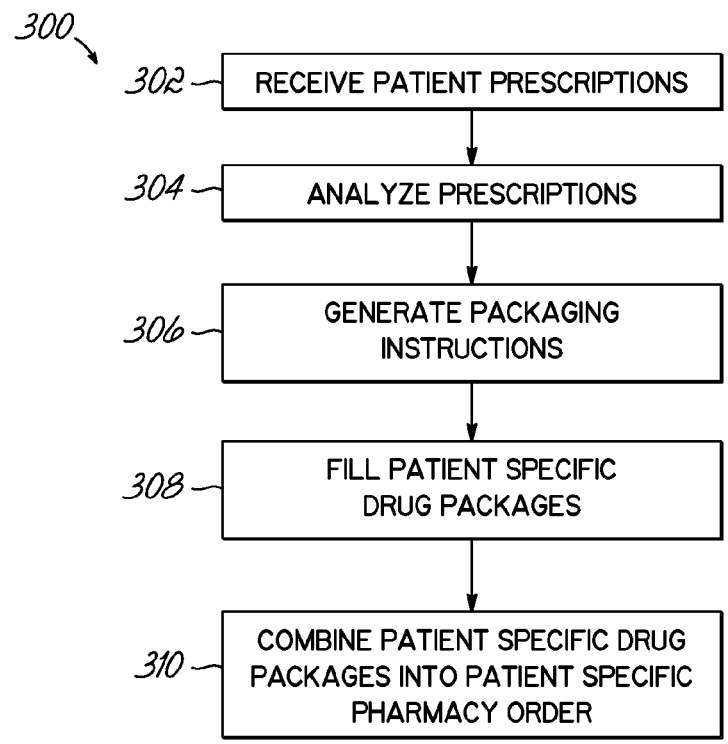
FIG. 15 is a flowchart of sequences of operations that may be performed by one or more processors of the drug packaging system of FIG. 1.

Referring to FIG. 15 which discloses flowchart 300, flowchart 300 provides a sequence of operations that may be performed by some embodiments of a drug packaging system 10 consistent with the invention. The drug packaging system 10 receives one or more patient prescriptions (block 302). For example, referring to FIG. 1, the drug packaging system 10 may receive the one or more patient prescriptions from the input devices 72, where the input devices 72 may include a barcode scanner and the patient prescriptions may be in the format of scannable barcodes. The drug packaging system 10 may receive the one or more patient prescriptions from the input devices 72, where the input devices may include a keyboard and/or mouse, and a user may input one or more prescriptions utilizing an interface configured to communicate prescriptions and prescription data to the drug packaging system 10. In some embodiments, the drug packaging system 10 may receive one or more patient prescriptions from a remote terminal 82 configured to communicate prescriptions and prescription data to the drug packaging system 10. In addition, the drug packaging system 10 may be configured to receive one or more prescriptions from external resources 80, where the external resources may be configured to communicate prescriptions and prescription data to the drug packaging system 10.

The drug packaging system 10 analyzes the received prescriptions (block 304), and the drug packaging system 10 generates packaging instructions based, at least in part, on the analyzed prescriptions (block 306). As discussed previously, the packaging instructions may indicate the specific drugs and the dosage of each drug to be placed in a patient specific drug package 90. For example, referring to FIG. 2A, the packaging instructions may indicate the medication and dosage of each medication to be placed in a particular compartment 94 of blister pack 90. Moreover, the generated packaging instructions may include data indicating the prescribed combination of the patient specific drug packages 90 such that a patient specific pharmacy order may be filled. The drug packaging system 10 may then fill the patient specific drug packages 90 based on the generated packaging instructions.

The drug packaging system 10 may combine the filled patient specific drug packages 90 into a patient specific pharmacy order based, at least in part, on the generated packaging instructions (block 310). For example, referring to FIGS. 1 through 3, drug packaging system 10 may receive one or more patient prescriptions, analyze the received prescriptions, generate packaging instructions, where the packaging instructions indicate each drug and the dosage of each drug to be placed in each compartment 94 of the blister pack 90. After filling the compartments 94 of one or more blister packs 90 based on the generated packaging instructions, the drug packaging system 10 may combine the blister packs 90 based at least in part on the generated packaging instructions to complete a patient specific pharmacy order similar to the patient specific pharmacy order shown in FIG. 3.

Figure 16:
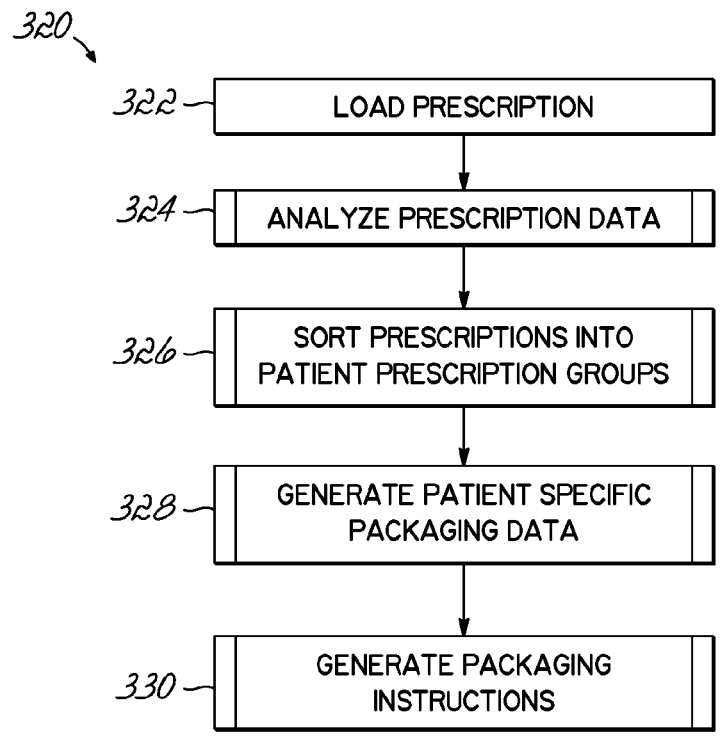
FIG. 16 is a flowchart of sequences of operations that may be performed by the drug packaging system of FIG. 1 to generate packaging instructions from prescription data.

In FIG. 16, flowchart 320 illustrates a sequence of operations that may be performed by a drug packaging system 10 consistent with some embodiments of the invention. The drug packaging system 10 loads one or more patient prescriptions (block 322). As disclosed above, the drug packaging system 10 may receive one or more patient prescriptions from a plurality of sources 72, 80, 82, and the drug packaging system 10 may load the prescriptions into memory 62 and/or storage locations 74 operatively connected to the drug packaging system 10. For example, referring to FIG. 1, the drug packaging system 10 may load the prescriptions into data structure 66, local storage 74, memory and/or data structures associated with external resources 80, and/or memory and/or data structures associated with remote terminals 82.

As discussed previously, the prescriptions may include prescription data, where the prescription data may indicate the patient and/or a unique patient identifier, the drug type, dosage amount, the dosing instructions, and/or patient administration time preferences. The drug packaging system 10 analyzes the prescription data of each prescription (block 324). The drug packaging system 10 sorts the prescriptions into patient prescription groups based, at least in part, on the analyzed prescription data of each prescription (block 326). Sorting the prescriptions into patient prescription groups may be utilized by a drug packaging system 10, such that the drug packaging system 10 may receive and/or load prescriptions corresponding to a plurality of patients.

The drug packaging system 10 may generate patient specific packaging data based, at least in part, on the analyzed prescription data of each prescription associated with a patient prescription group (block 328). For example, in some embodiments, patient specific packaging data may be based, at least in part, on a contra-indication between two drugs included in prescriptions associated with a patient prescription group. Moreover, in some embodiments, patient specific packaging data may be based, at least in part, on patient administration time preferences indicated in the prescription data or other sources, including for example, an external server including patient preference data associated with a patient. For example, prescription data for one or more prescriptions associated with a patient prescription group may indicate that the patient prefers or the prescribing physician recommends taking two lower dosage pills of a particular drug as opposed to one high dosage pill of the same drug, and as such, the generated patient specific packaging data may be based, at least in part, on the indicated preference. In another example, prescription data for the patient may indicate that the patient does not awaken before lunchtime, and therefore no morning medication pass times should be presented to the patient.

The drug packaging system 10 may generate packaging instructions based at least in part on the generated patient specific packaging data (block 330). Referring to FIG. 1, the drug packaging system 10 may generate packaging instructions for manual packaging station 14 and/or for automated packaging station 16. As such, in some embodiments, the packaging instructions may be based at least in part on the type of packaging station 14, 16 that will fill the patient specific drug packages 90 of the patient specific pharmacy order.

Figure 17:
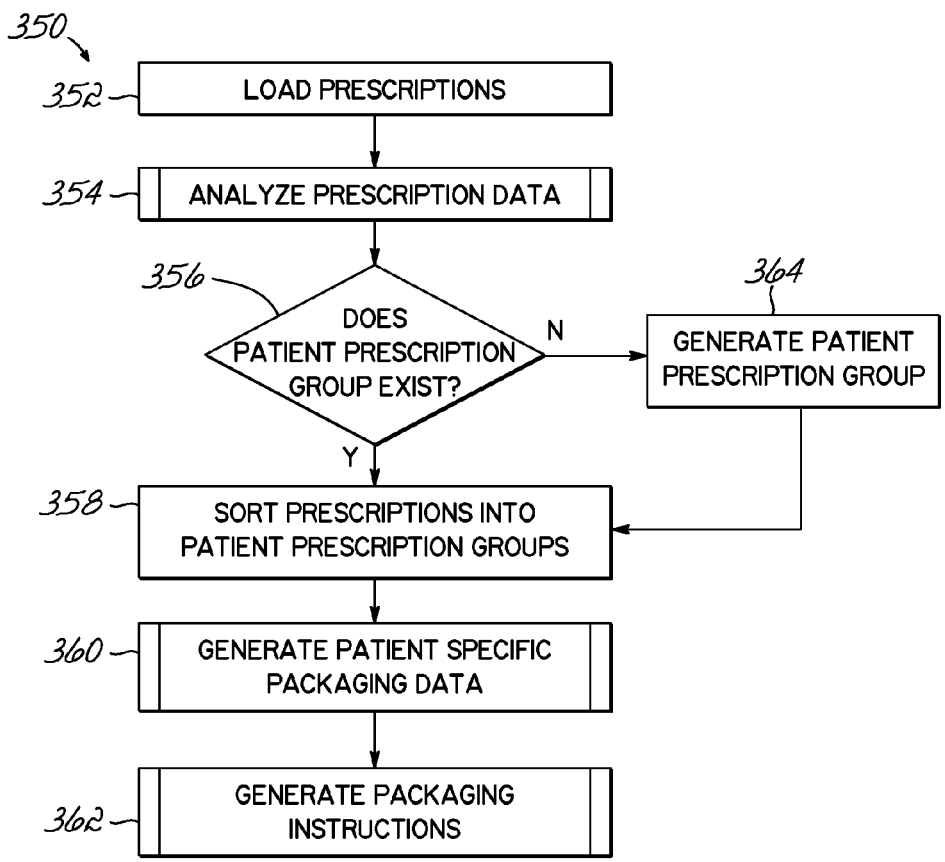
FIG. 17 is a flowchart of sequences of operations that may be performed by the drug packaging system of FIG. 1 to determine if a new prescription applies to a current patient or a new patient.

Referring now to FIG. 17, flowchart 350 illustrates a sequence of operations that may be performed by a drug packaging system 10 consistent with some embodiments of the invention. A drug packaging system 10 consistent with some embodiments of the invention may load the prescriptions (block 352), and analyze the prescription data of each prescription (block 354). The drug packaging system 10 may determine whether a patient prescription group associated with a patient identified in the prescription data of each prescription exists in the drug packaging system 10 (block 356). The patient prescription groups and associated prescriptions may be stored in memory 62 and/or storage locations 74 operatively connected to the drug packaging system 10. As such, the drug packaging system 10 may thereby operate to update a previously generated patient prescription group with new prescriptions loaded into the drug packaging system 10.

In response to determining that the patient prescription group does exist in the memory 62 and/or storage location 74, the drug packaging system 10 may sort prescriptions into the patient prescription group associated with the patient identified in the prescription data of each prescription (block 358). The drug packaging system 10 may generate patient specific packaging data based at least in part on the analyzed prescription data of each prescription associated with a patient prescription group (block 360), and the drug packaging system 10 may generate packaging instructions based at least in part on the patient specific packaging data (block 362). In response to determining that the patient prescription group does not exist in the memory 62 and/or storage location 74 at block 356, the drug packaging system 10 may generate a patient prescription group associated with a patient identified in prescription data of a loaded prescription (block 364), and then the sequence of operations continues at block 358 as described above.

Figure 18:
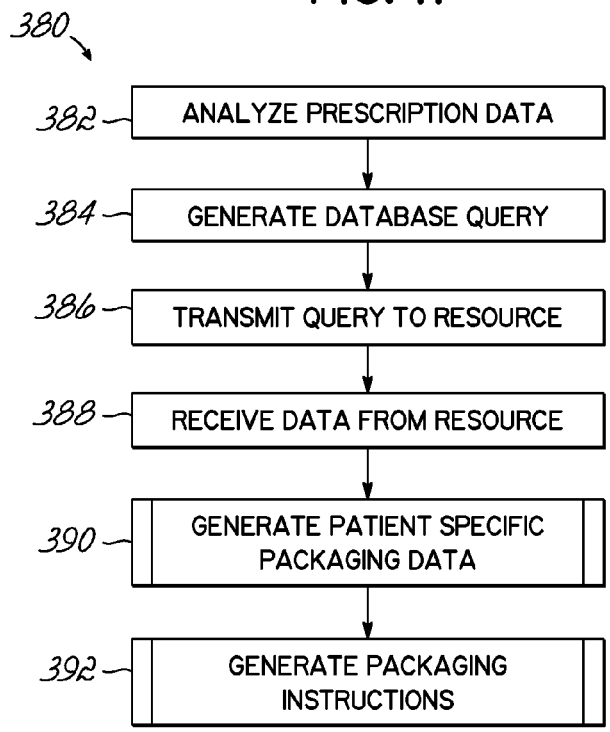
FIG. 18 is a flowchart of sequences of operations that may be performed by the drug packaging system of FIG. 1 to analyze prescription data.

Referring to FIG. 18, flowchart 380 illustrates a sequence of operations that may be performed by a drug packaging system 10 consistent with some embodiments of the invention. The drug packaging system 10 may analyze prescription data of one or more prescriptions (block 382), and the drug packaging system 10 may generate a database query based at least in part on the analyzed prescription data (block 384). For example, referring to FIG. 1, the analyzed prescription data may indicate the drug type of one or more prescriptions for a patient, and drug packaging system 10 may generate a database query based on the indicated drug types. The generated query may be transmitted to a resource (block 386), for example, external resources 80, remote terminals 82, and/or local storage 74. The drug packaging system 10 may receive data from the queried resource (block 388), for example, the resource may return drug contra-indication data, patient administration time preference data, patient medical data, etc. Based at least in part on the data received from the queried resource, the drug packaging system 10 may generate patient specific packaging data (block 390), and the drug packaging system 10 may generate packaging instructions based, at least in part, on the generated patient specific packaging data (block 392).

Figure 19A:
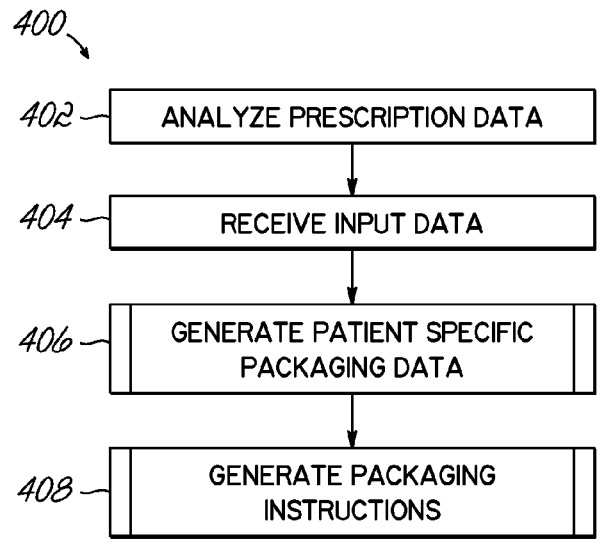
FIG. 19A is a flowchart of sequences of operations that may be performed by the drug packaging system of FIG. 1 to generate packaging instructions from other input data.

In some embodiments, a drug packaging system 10 consistent with embodiments of the invention may receive input data from one or more sources, and the patient specific drug packages (e.g., blister packs 90) may be filled with one or more drugs of prescribed dosages based, at least in part, on the received input data. Referring to FIG. 19A, flowchart 400 illustrates a sequence of operations that may be performed by the drug packaging system 10. In some embodiments, the drug packaging system 10 may analyze prescription data of each prescription for a patient (block 402). The drug packaging system 10 may receive input data from one or more sources. For example, referring to FIG. 1, drug packaging system 10 may receive input data from input devices 72, remote terminals 82, and/or external resources 80. Based at least in part on the received input data and/or the analyzed prescription data, the drug packaging system 10 may generate patient specific drug packaging data (block 406), and the drug packaging system 10 may generate packaging instructions based, at least in part, on the generated patient specific drug packaging data (block 408).

Figure 19B:
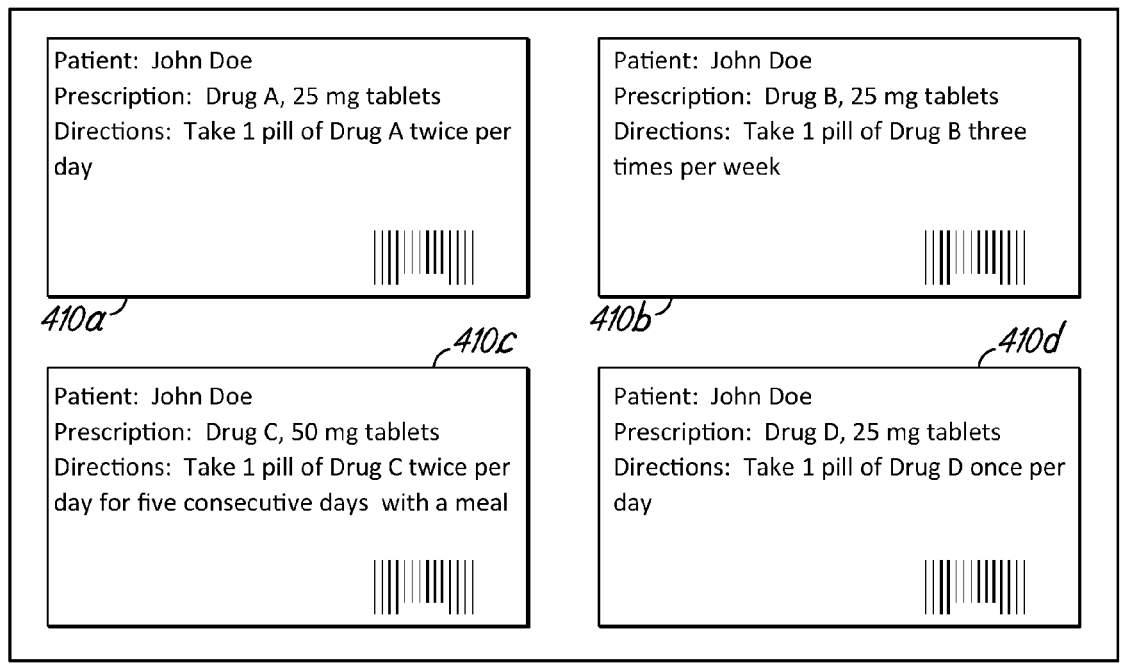
FIG. 19B is a schematic view of four prescriptions used in an exemplary operation of the drug packaging system of FIG. 1 to generate packaging instructions.

One simplified example of producing filling instructions from a series of prescriptions is shown schematically in FIGS. 19B through 19D. Referring now to FIG. 19B, which provides four exemplary prescriptions 410a, 410b, 410c, 410d, where the exemplary prescriptions 410a, 410b, 410c, 410d include prescription data comprising a patient name, drug name, drug strength, drug form, dosing amount, and/or dosing instructions. Using embodiments consistent with the invention, the exemplary prescriptions 410a, 410b, 410c, 410d and the included prescription data may be analyzed and patient specific packaging data corresponding to the patient may be generated based, at least in part, on the patient name, drug name, drug strength, drug form, dosing amount, and/or dosing instructions.

FIG. 19C provides an exemplary chart 412 which illustrates patient specific packaging data corresponding to the exemplary prescriptions 410a, 410b, 410c, 410d of FIG. 19B. As shown in FIG. 19C, patient specific packaging data may be generated by analyzing loaded prescriptions, where the patient specific packaging data indicates a patient specific drug package in which one or more different drugs are to be packaged. Chart 412 includes a plurality of blister packs 90, where each blister pack 90 includes a plurality of compartments 94. The compartments 94 are configured to hold one or more medications that a patient is prescribed. Those skilled in the art will recognize that chart 412 is a relatively simplified example used to illustrate patient specific packaging data, where the patient specific packaging data may comprise a variety of data structures and formats readable by controllers of a drug packaging system 10.

Chart 412 illustrates patient specific packaging data for seven days of a patient specific pharmacy order, where a blister pack 90 corresponds to a specific date and time of the day (morning, lunchtime, evening, bedtime). In this exemplary embodiment, each blister pack 90 includes eight blister compartments 94. The patient specific packaging data indicates the appropriate compartment 94 of a blister pack 90 into which each tablet of a prescription should be placed. As such, chart 412 illustrates exemplary drug packaging data that may be generated from the four exemplary prescriptions of FIG. 19B.

FIG. 19D provides exemplary chart 414 which illustrates patient specific packaging data corresponding to the exemplary prescriptions of FIG. 19B. As such, chart 414 of FIG. 19D is an alternative exemplary embodiment of patient specific packaging data as compared to chart 412 of FIG. 19C. Moreover, the patient specific packaging data illustrated in chart 414 illustrates an example where the patient specific packaging data is generated based, at least in part, on prescription data associated with the loaded prescriptions, patient preference data received from an external resource, and/or drug contra-indication data received from an external resource. In this example, patient administration time preference data indicates that the patient does not awaken each day in the morning time period and that the drugs of prescriptions 410c and 410d (e.g., Drug C and Drug D) of FIG. 19B have a contra-indication, and should not be taken at the same dosing time.

Based at least in part on the prescription data, the patient preference data, and the drug contra-indication data, the patient specific drug packaging data is generated. As opposed to chart 412, chart 414 includes blister packs 90 corresponding to only three times of day (lunchtime, evening, bedtime) because the patient preference data indicated that the patient does not awaken in time to take medication at the morning time slot. As such, blister packs 90 associated are not filled, and hence, patient specific packaging data is not generated for morning blister packs 90. Moreover, as shown in chart 414, the patient specific packaging data indicates that the drugs of prescriptions 410c and 410d (e.g., Drug C and Drug D) of FIG. 19B are not packaged to be taken by the patient at the same dosing time, because the drug contra-indication data indicated that the drugs may have an undesirable effect when administered at the same time. Thus, the chart 414 of filling instructions in this alternative embodiment takes into consideration patient preference and drug contra-indication, as well as other factors.

It will be understood that the generation of the filling instructions (e.g., the allocations of medications to compartments 94 in blister packs 90) may also be tailored to fit the particular packaging station 14, 16 that will be used to fill the blister packs 90. For example, if the automated packaging station 16 described in co-pending U.S. patent application Ser. No. 13/529,554 (incorporated by reference above) is to be used to fill blister packs 90 of a particular medication pass, then the filling instructions will be tailored to allocate only one medication to all first compartments 94 of the blister packs 90, only one medication to all second compartments 94, and so on. This allocation will enable the automated packaging station 16 to not require relative movement between cassettes and blister packs 90 during the filling of all blister packs 90 for that medication pass. If the manual packaging station 14 is to be used to fill the blister packs 90, then the filling instructions will be tailored to limit the number of separate pill counting and filling steps that must take place to fill an entire medication pass worth of blister packs 90. In both circumstances, the filling instructions will also be tailored to limit the number of empty compartments 94 left in the blister packs 90 as long as that effort does not interfere with the operation at the respective packaging stations 14, 16. These and other factors will be incorporated into the analysis of the prescriptions and the generation of the filling instructions, as exemplified in the charts 412, 414 described above.

As such, in some embodiments, the drug packaging system 10 may load a plurality of prescriptions corresponding to a plurality of patients. In these embodiments, the drug packaging system 10 may be configured to sort the prescriptions into patient prescription groups based on the patient identified in the prescription data of each loaded prescription, such that the drug packaging system 10 may process and fill patient specific pharmacy orders for each unique patient of the plurality of patients.

Those skilled in the art will recognize that the exemplary environment illustrated in FIG. 1 is not intended to limit the invention. Indeed, those skilled in the art will recognize that other alternative hardware and/or software environments may be used without departing from the scope of the embodiments of the invention. For example, controllers 12, 18, and 42 may be embodied in one or more controllers configured to perform the functions described above with regard to controllers 12, 18, and 42. Those skilled in the art will also recognize that the invention contemplates all types of controllers including computing systems and other programmable electronic devices configured with processors, memory and/or storage devices, including, for example, client computers, server computers, portable computers, handheld computers, embedded controllers, general purpose controllers, special purpose controllers, etc.

Once the packaging or filling instructions are generated based on the various prescription data and patient preferences as described in FIGS. 15 through 19D, the instructions are ready for delivery to the manual packaging station 14 or to the automated packaging station 16. With reference to the manual packaging station 14 that is the focus of the description below, the operator 22 may then follow the prompts created by the controller 18 of the manual packaging station 14 to fully package and/or verify the proper packaging of the order for a patient.

With reference to the flowcharts shown in FIGS. 20 through 32B, an exemplary filling and verification process for the blister packs 90 is shown and described in detail below. In the exemplary embodiment, each order for a particular month and a particular patient will have been broken into filling instructions for up to 120 or more individual blister packs 90 (i.e., thirty days times four medication passes per day), and each order will be filled completely before moving to the next order. Thus, 120 individual blister packs 90 will be separated into eight trays 40 of fifteen each. The trays 40 will generally be organized such that the first tray 40 filled at the shutter assembly 38 represents the morning medication pass for days 1-15 of the month, the second tray 40 represents the morning medication pass for days 16-30 of the month, the third tray 40 represents the lunchtime medication pass for days 1-15 of the month, and so on. Once each of the eight trays 40 for a month has been filled with the appropriate medications, the trays 40 are delivered to post-filling verification and packaging. This post-filling packaging may include additional loading of non-cassette dispensable medication products, additional verification by a pharmacist or certified pharmacy technician when appropriate per federal and state laws, and reprinting and application of new covers 96 to the blister packs 90 where needed. The post-filling packaging may also include collation and consolidation of the order into cartons 120a, 120b, 120c, 120d and other packaging, such as when the order includes non-blister pack medications or PRN blister packs 90, and shipping to the patient. As outlined above, it will be appreciated that more or fewer blister packs 90 and trays 40 may be used for a given "month" and the example above is shown for illustrative purposes only.

An example of a particular order may be as follows: a patient is instructed to take in the morning two pills of drug A every day; one pill of drug B on Mondays, Wednesdays, and Fridays; and one-half pill of drug C every three days. Assuming the first day of the "month" is a Monday, the first blister pack 90 (for Monday) should have a pill of drug A in compartment 1, a pill of drug A in compartment 2, a pill of drug B in compartment 3, and a half-pill of drug C in compartment 4. The second blister pack 90 (for Tuesday) should have a pill of drug A in compartment 1, a pill of drug A in compartment 2, and nothing in compartments 3 and 4. The third blister pack 90 (for Wednesday) should have a pill of drug A in compartment 1, a pill of drug A in compartment 2, a pill of drug B in compartment 3, and nothing in compartment 4. The fourth blister pack 90 (for Thursday) should have a pill of drug A in compartment 1, a pill of drug A in compartment 2, nothing in compartment 3, and a half-pill of drug C in compartment 4. The filling process will fill each of the pills of compartment 1 for a particular tray 40 followed by all the pills for compartment 2, etc. The process may be modified to minimize empty compartments 94 in other embodiments with more medications per blister pack 90.

Figure 20:
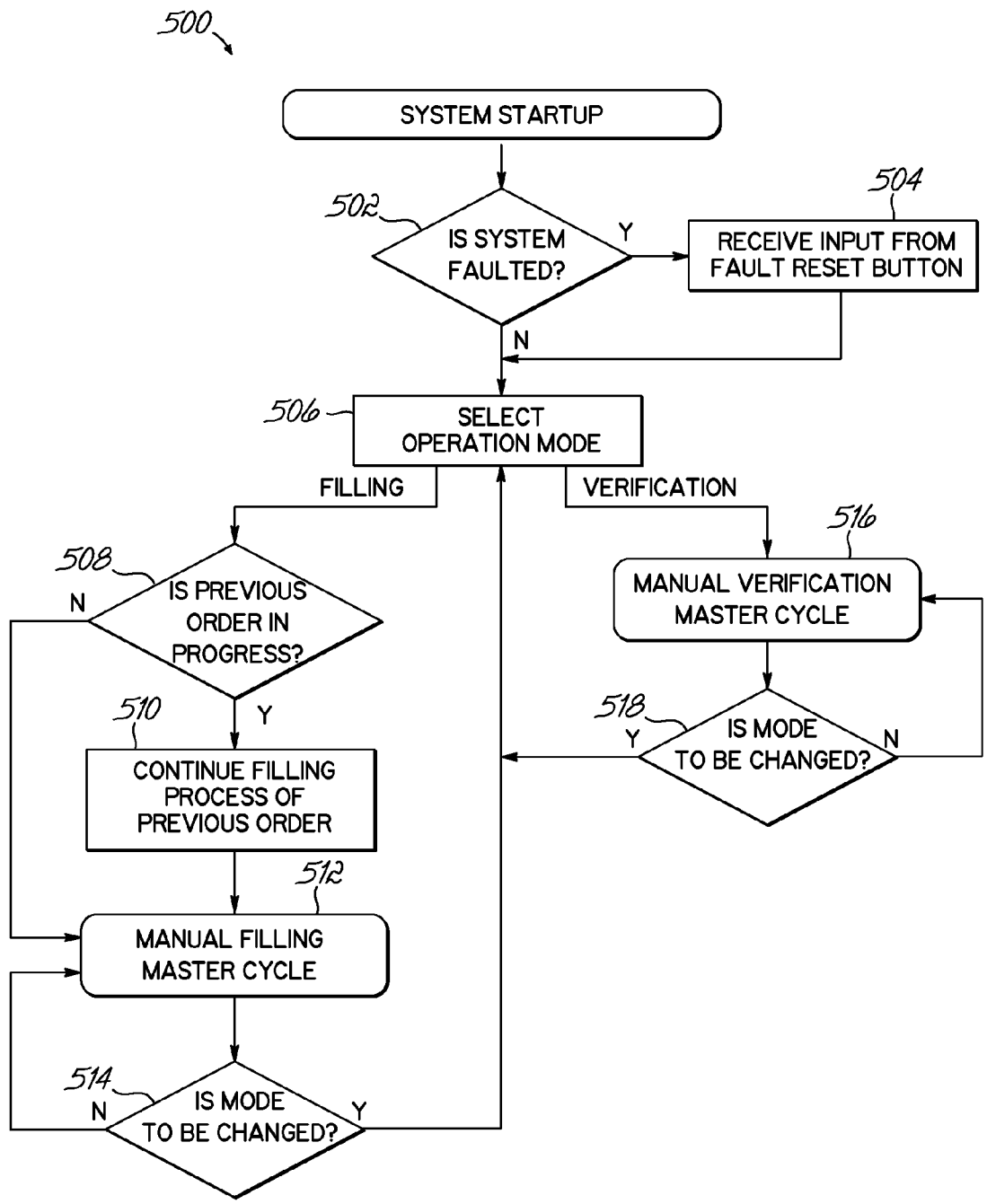
FIG. 20 is a flowchart showing a sequence of operations that may be performed during system startup of the manual packaging station of FIG. 4.

With reference to FIG. 20, flowchart 500 illustrates a sequence of operations that may be performed by the manual packaging station 14 during a system startup. In this regard, the sequence begins at startup of the manual packaging station 14 by having the machine controller 18 check to see if the system 14 was faulted at the last system shutdown (block 502). If so, then the controller 18 waits to receive input from a fault reset button, which may be incorporated in the visual display monitor 36 (block 504). Once this input is received, or if the manual packaging system 14 was not faulted at step 502, then the controller 18 receives a selection of the operation mode (block 506). This operation mode may be "Verification" for use of the manual packaging station 14 to inspect previously-filled blister packs 90, or the mode may be "Filling" for use of the manual packaging station 14 to fill blister packs 90 (block 906).

If the selected operation mode is "Filling", then the controller 18 determines if a previous order was in progress before the last system shutdown (block 508). If a previous order was in progress and interrupted, then the controller 18 operates the manual packaging station 14 to continue filling the previous order (block 510). Once this process is complete, or if there were no previous order that had been interrupted, the controller 18 operates a manual filling master cycle that is further described with reference to FIG. 21 below (block 512). After running this manual filling master cycle 512, the controller 18 checks to see if any input has been received from the operator 22 to change the operation mode (block 514). If the operation mode is not to be changed, then the manual filling master cycle 512 repeats. If the operation mode is to be changed, then the controller 18 returns to step 506 to select the operation mode again. Alternatively, if the selected operation mode is "Verification", then the controller 18 operates a manual verification master cycle that is further described with reference to FIGS. 32A and 32B below (block 516). After running this manual verification master cycle 516, the controller 18 checks to see if any input has been received from the operator 22 to change the operation mode (block 518). If the operation mode is not to be changed, then the manual verification master cycle 516 repeats. If the operation mode is to be changed, then the controller 18 returns to step 506 to select the operation mode.

Figure 21:
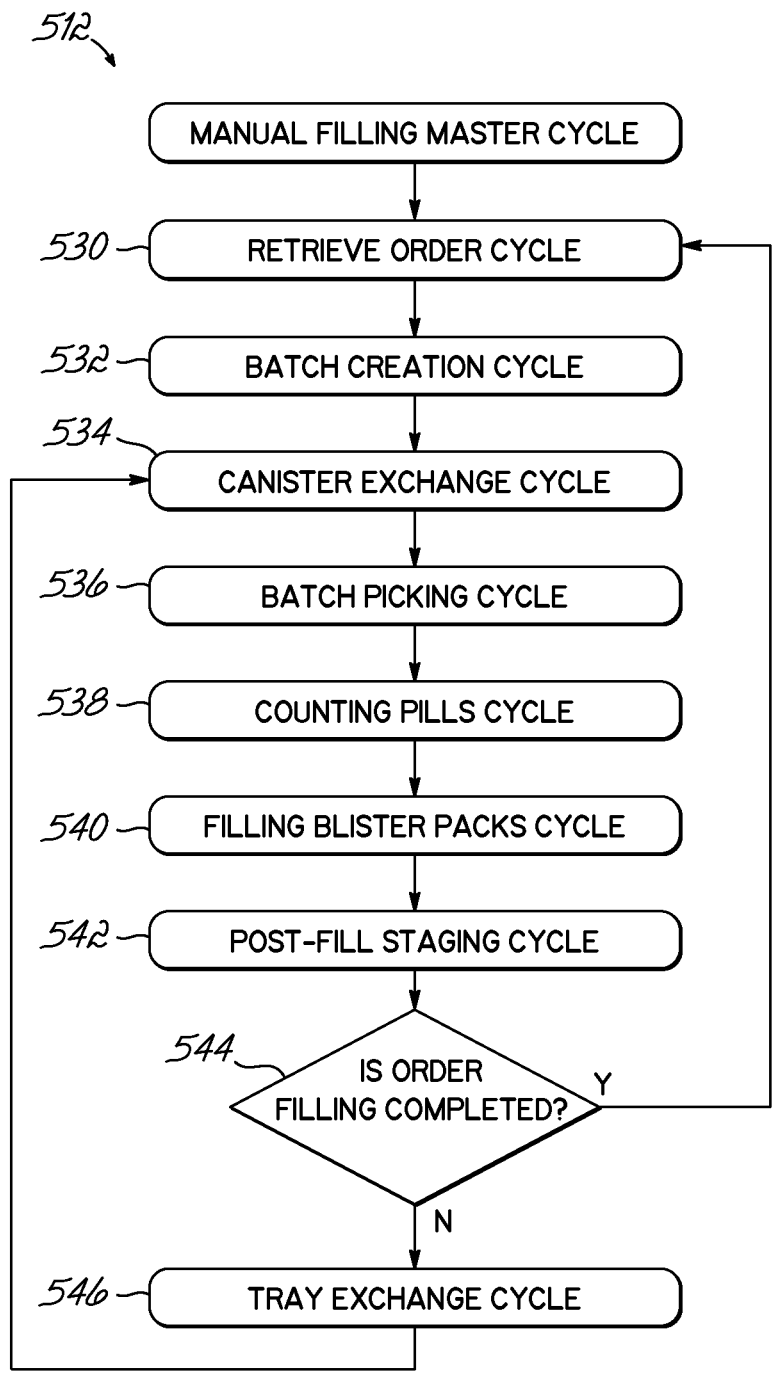
FIG. 21 is a flowchart showing a sequence of operations that may be performed during the manual filling master cycle of FIG. 20.

With reference to FIG. 21, the series of operations defining the manual filling master cycle 512 is shown in further detail. The manual filling master cycle 512 begins with the controller 18 of the manual packaging machine 14 performing a retrieve order cycle (block 530), further described in FIG. 22 below, to select a new order to fill at the manual packaging machine 14. The controller 18 then performs a batch creation cycle (block 532) as described and shown in FIG. 23 below to create a batch of medications required for a single pass time of blister packs 90 (two or more trays 40) or one or more trays 40 of PRN blister packs 90. Next, the controller 18 operates a canister exchange cycle (block 534) and a batch picking cycle (block 536) that ensure the canisters 26 at the staging bar 32 match what is required by the current batch. The canister exchange cycle 534 is described with reference to FIGS. 24A and 24B below and includes a series of canister returns to the carousels 24. The batch picking cycle 536 is described with reference to FIGS. 25A and 25B below and includes a series of retrievals of canisters 26 from the carousels 24.

Then, the controller 18 will perform a counting pills cycle (block 538) that will direct the operator 22 to take one canister 26, place it on one of the pill counters 34, and count out the required number of pills for the current tray 40, as described in detail in FIGS. 26A and 26B below. The controller 18 then performs a filling blister packs cycle (block 540) that prompts the operator 22 to place the counted pills into the appropriate compartments 94 of the empty blister packs 90, as shown and described in FIGS. 29A and 29B below. As described in detail below, the controller 18 will direct the operator 22 to put the canister 26 back to the staging bar 32 and move another canister 26 from the staging bar 32 to the counters 34, thereby repeating the counting and filling cycles 538, 540 for all canisters 26 to be used from the batch of canisters 26 on the staging bar 32. Once all blister packs 90 of a tray 40 are filled, the controller 18 will operate a post-fill staging cycle (block 542), which is shown in FIG. 30 and directs the operator 22 to take the tray 40 out of the shutter assembly 38, place a cover on the tray 40, and take the tray 40 to a post-fill staging area.

The controller 18 will then determine if the filling is completed for the order (block 544). If filling is completed for the order, then the controller 18 will check to see if a shutdown request or request to change operational modes has been received. The controller 18 will then return to the retrieve order cycle of step 530 as described above to obtain a new order. If the filling is not completed for the order at step 544, the controller 18 will perform a tray exchange cycle (block 546) as described and shown in FIG. 31. The tray exchange cycle 546 prompts the operator 22 to insert another tray 40 for the same batch or for the next batch into the shutter assembly 38. Once all trays 40 for the batch's medication pass time (or all PRN blister packs 90 for that batch) are filled, the controller 18 will get a new batch for the next medication pass time of the same order by returning to the canister exchange cycle of step 534. That process repeats for all pass times in the order. These related series of operations are described in further detail below.

Figure 22:
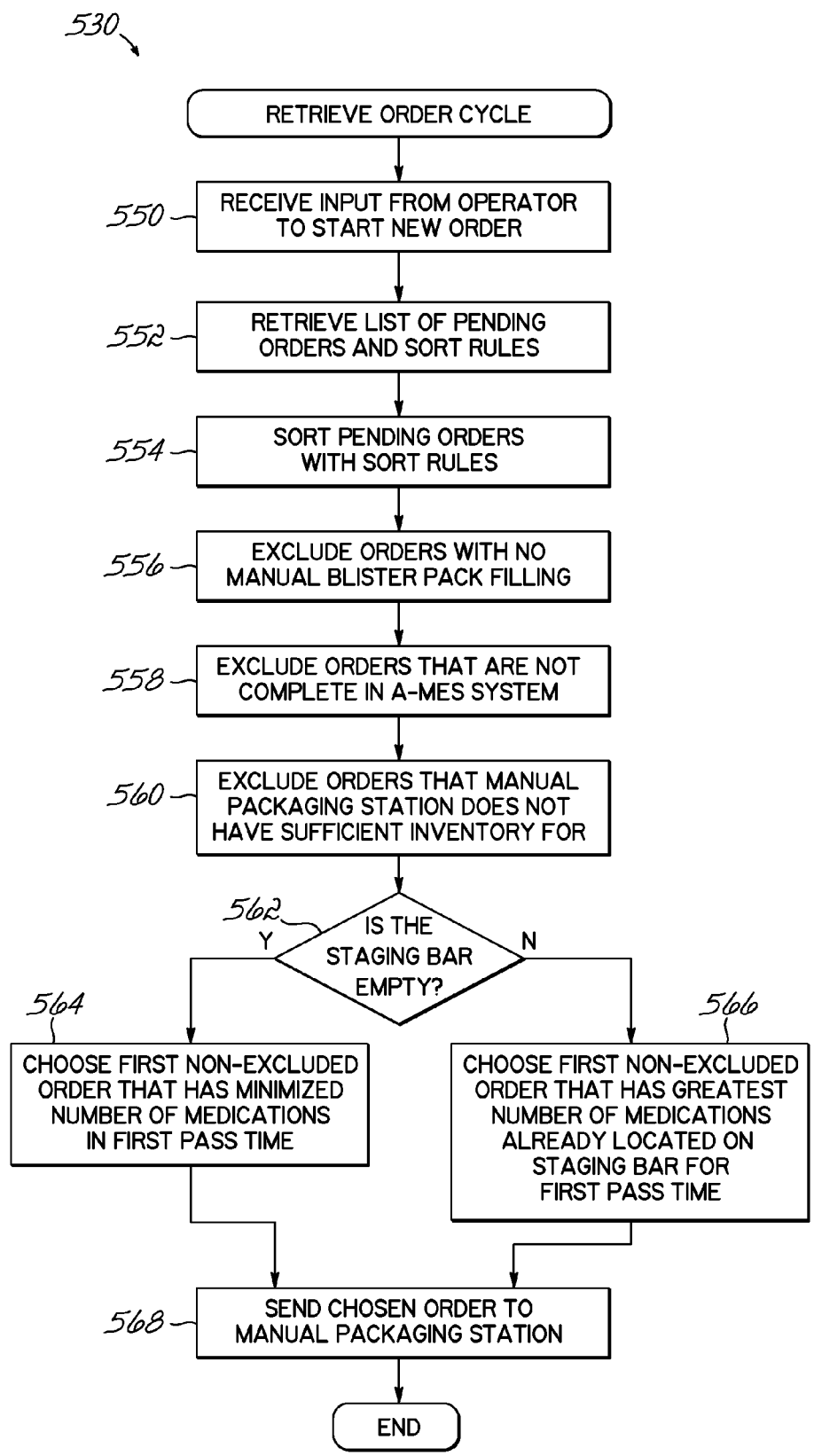
FIG. 22 is a flowchart showing a sequence of operations that may be performed during the retrieve order cycle of FIG. 21.

With reference to FIG. 22, the retrieve order cycle 530 of the manual filling master cycle 512 is shown in further detail. The cycle 530 begins with the controller 18 receiving input from the operator 22 to start a new order (block 550). For example, there will be a button produced on the display monitor 36 to request a new order. This button will only be enabled to the operator 22 when no order is active. When the operator 22 clicks this button, the manual packaging station 14 will request a new order from the Host Interface or controller 12. In this regard, the controller 12 (or the machine controller 18) will retrieve a list of pending orders and sort rules (block 552). The Host Interface will use this set of sort rules in combination with additional factors to determine the order to send back to the manual packaging station 14. These sort rules can be defined by the operator 22 with a set of fields to group by, and a set of fields to sort those groups by (either ascending or descending for each).

For example, a sort rule might be defined with group by fields of: DATE_TO_SHIP, CYCLE_START_DATE, PACKAGE_TYPE, ORDER_NUMBER, and PASS_TIME. The sort rule might be further defined with sort by fields of: DATE_TO_SHIP (ascending), CYCLE_START_DATE (ascending), and PASS_TIME (ascending). In this case, when an order is requested, the Host Interface would take all the picks that it has received and group them so that all the picks with the same DATE_TO_SHIP, CYCLE_START_DATE, PACKAGE_TYPE, ORDER_NUMBER, and PASS_TIME are in the same group. This essentially generates a list of groups. Those groups would then be sorted by DATE_TO_SHIP, then by CYCLE_START_DATE, and then by PASS_TIME. The system will take the top group in the list, and build a list of all pick records that match the "sort by" fields of that record. In this example, it would now have a list of picks that all have the earliest DATE_TO_SHIP, then CYCLE_START_DATE, then PASS_TIME, but would be for any number of orders.

Returning to FIG. 22, the controller 12 will generate a list of orders by sorting the pending orders with the sort rules determined as described above (block 554). To narrow the list down to a single order to fill, some additional filters will be used. The controller 12 will exclude any orders in the list with no manual blister pack filling, such as those blister packs 90 to be filled by the automated packaging station 16 (block 556). Next, the controller 12 will exclude any orders which the system has not completely received (block 558). In this regard, each pick/order record may include a field called ITEM_COUNT. This reflects the number of records that will be in the entire order when completed in an A-MES (automated manufacturing execution system) order management system, and all records in the order will have the same value for this field. When the system has received as many records for an order as the ITEM_COUNT field of those records, the order is then available to be used for filling and would not be excluded in this filtering step 558. Next, for each order, the controller 12 will make sure there is enough inventory in canisters 26 in the carousels 24 to complete the order, excluding the order from the available list if there is not enough inventory available to fill the entire order at the manual packaging station 14 (block 560). This process may also trigger a replenishment or refill request for the canisters 26 that do not contain sufficient inventory to avoid exclusion of the orders in the future.

Additionally, the controller 18 will determine if the staging bar 32 is empty or has a batch of canisters 26 in position from a previous order (block 562). In view of this determination, the controller 12 will look at the list of orders still remaining in the sorted list and check them for commonality with the canisters 26 currently on the staging bar 32, should there be any canisters 26 there. If there are no canisters 26 on the staging bar 32, the controller 12 will choose the first non-excluded order from the list whose earliest pass time (e.g., the first batch to be collected) has the fewest number of unique NDCs (i.e., National drug code designations) or medications to be pulled from the carousels 24 (block 564). If there are canisters 26 located on the staging bar 32, the controller 12 will calculate, for each non-excluded order in the list, the number of NDCs or medications in the order's earliest pass time that are in common with the medications (NDCs) on the staging bar 32, and will choose the order with the highest value for this calculation (block 566), to thereby minimize the number of canisters 26 that need to be exchanged between the carousels 24 and the staging bar 32. Once the order has been determined, the controller 12 will send the chosen order to the PalmPak Fill application and the machine controller 18 (block 568) and the retrieve order cycle 530 ends.

Figure 23:
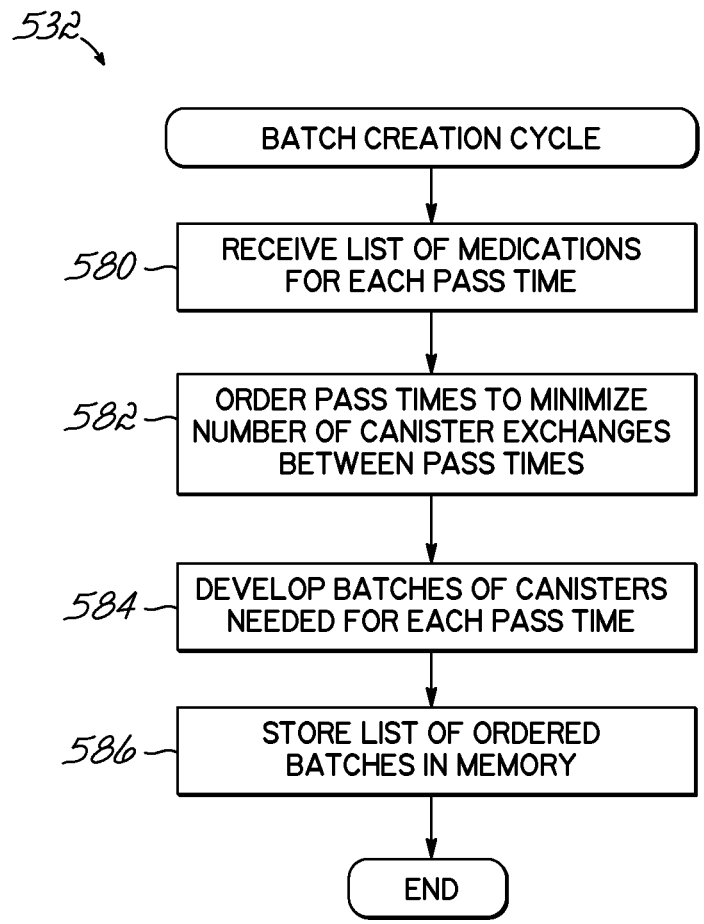
FIG. 23 is a flowchart showing a sequence of operations that may be performed during the batch creation cycle of FIG. 21.

With reference to FIG. 23, the controller 18 will then generate a plurality of batches by using all the picks for the pass times or PRN requirements of the order, as shown in the series of operations forming the batch creation cycle 532. To this end, the controller 18 retrieves a list of medications or "picks" for each pass time in the order (block 580). The controller 18 then orders the pass times to minimize the number of canister exchanges that need to take place between adjacent pass times (block 582). Similar to the selection of an order with minimal canister 26 movement required for the first pass time described above, this ordering improves the efficiency of the manual packaging station 14 by minimizing operator 22 workload. The controller 18 develops batches of canisters 26 that will be needed for the ordered list of pass times (block 584). These batches will define how the following series of operations are performed and repeated to fill the entire order of blister packs 90. The information for the batches will then be stored in a memory file local to the manual packaging station 14 (block 586). At this point, the display monitor 36 will visually show (in a list or some other format) the canisters 26 needed to fill the first tray 40 or the first medication pass, as well as the active order number and the status of all mechanical equipment and scanners communicating with the controller 18. The batch creation cycle 532 then ends and the controller 18 moves on to the canister exchange cycle 534, to move unnecessary canisters 26 back to the carousels 24.

Figure 24A:
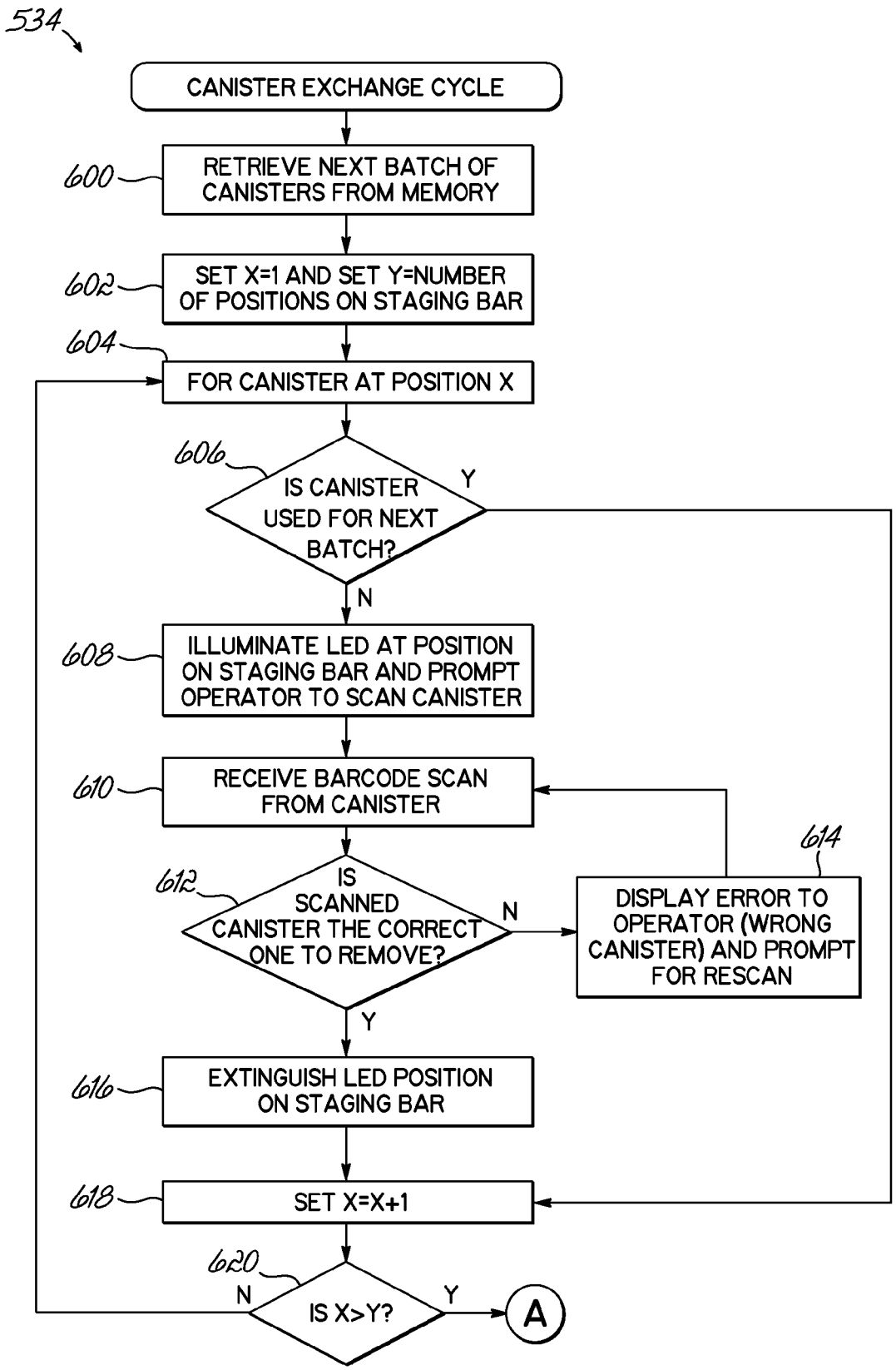
FIG. 24A is a flowchart showing a sequence of operations that may be performed during the canister exchange cycle of FIG. 21.
Figure 24B:
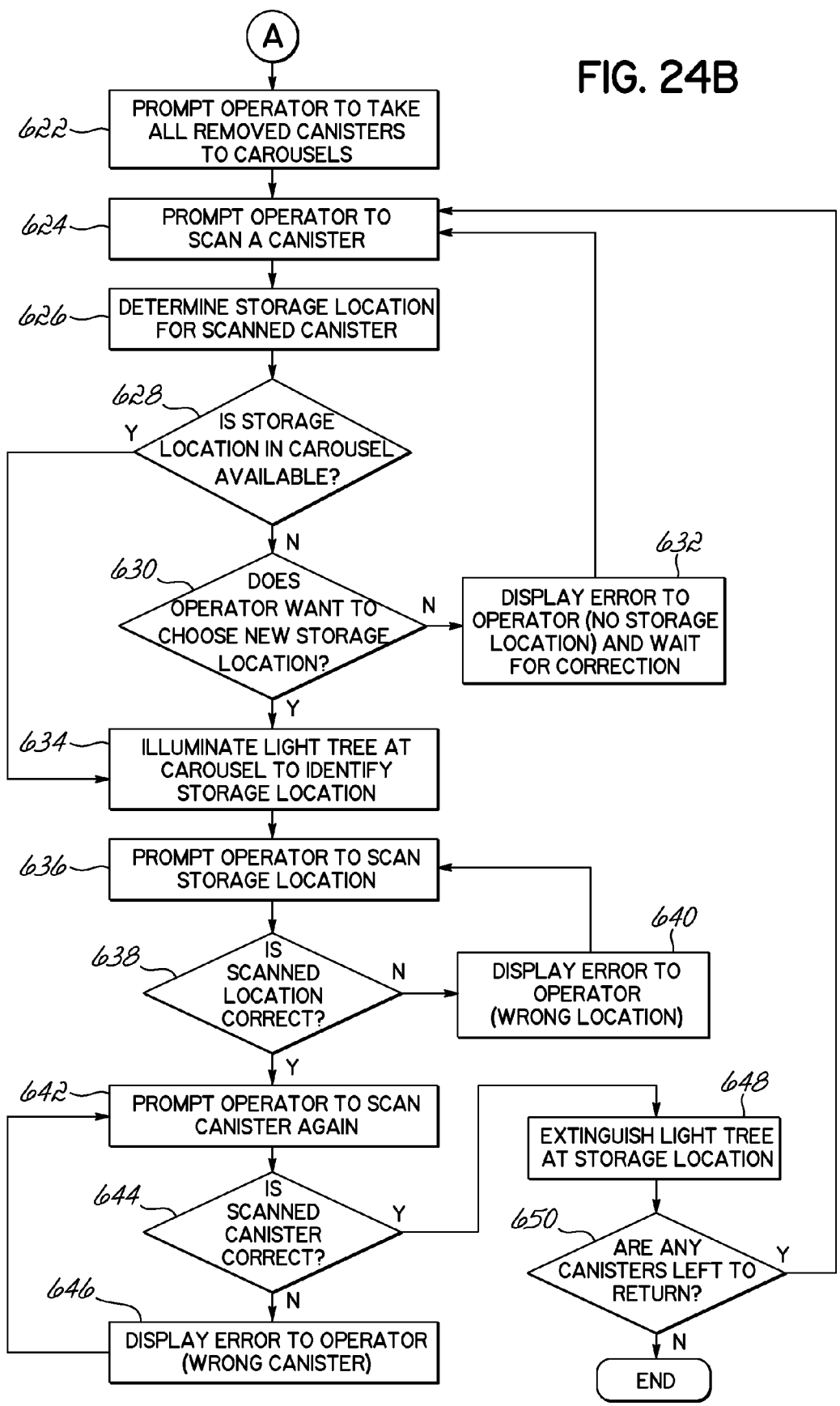
FIG. 24B is a flowchart showing a further sequence of operations that may be performed during the canister exchange cycle of FIG. 24A.

With reference to FIGS. 24A and 24B, the series of operations defining the canister exchange cycle 534 are shown in further detail. In sum, once a batch has been made active by the controller 18, the manual packaging station 14 will direct the operator 22 to put back any canisters 14 that are on the staging bar 20 that will not be used by the new batch. First, the controller 18 will retrieve the next batch of canisters 26 to be used from memory (block 600). The controller 18 will also set a variable X equal to 1 and another variable Y equal to the total number of positions on the staging bar (block 602). For the canister at position X (block 604), the controller 18 determines if the canister 26 at that position is used in the next batch (block 606). If the canister 26 is unnecessary for the next batch, the operator 22 will be prompted to take this canister 26 and all unneeded canisters 26 off the staging bar 32.

More specifically, if the canister 26 at position X is determined to be not needed for the next batch, the controller 18 will illuminate the indicator light 32a for that location in the staging bar 32 with a LED flashing red, and an associated display will read "Scan" To prompt the operator 22 to scan the canister 26 (block 608). The display monitor 36 will also illustrate a representation of the staging bar 32 with the same flashing LED and "Scan" display shown schematically. The operator 22 should take the designated canister 26 out of the staging bar 32 and scan the canister 26, which verifies that the correct canister 26 was taken. The controller 18 receives this barcode scan from the canister 26 (block 610) and then determines if the scanned canister 26 is the correct one to remove (block 612). If the scanned canister 26 is incorrect, the controller 18 will cause an error to be displayed (on the display monitor 36 or otherwise) to the operator regarding the wrong canister 26 and will prompt for a rescan (block 614). If the scanned canister 26 is verified to be correct, the operator 22 should then put the canister 26 onto a cart and the light at the staging bar 32 location be extinguished (block 616). The controller 18 then increments the variable X by one (block 618) and checks if X exceeds Y (block 620), which would indicate that all positions on the staging bar 32 have been checked. If X does not exceed Y, then the controller returns to step 604 to begin the process for the next location in series. To this end, if there are any other canisters 26 not needed by the next batch, then another light at a different staging bar 32 location will turn on. The operator 22 should continue removing canisters 26 from the staging bar 32 and placing them on the cart as long as staging bar 32 lights come on.

The operator 22 will be able to tell that the last canister 26 not needed for the next batch has been removed because no more indicator lights 32a on the staging bar 32 will illuminate. Instead, the controller 18 will prompt the operator 22 to take the canisters 26 to the carousels 24 (block 622) and prompt the operator 22 to scan one of the canisters (block 624). Simultaneously, the display monitor 36 will also instruct the operator 22 to take the canisters 26 to the carousels 24. The operator 22 should take any one of the canisters 26 that was removed from the staging bar 32 and scan it. At this point, the controller 18 will determine where in the carousels 24 the scanned canister 26 should be placed (block 626). The canister 14 was assigned a zone (e.g., gold, emerald, or ruby) and a carousel number when it was first placed into the carousel 24 from a replenishment process not described herein. The controller 18 will use the carousel number and zone to find a storage location for the canister 26.

The controller 18 will determine if any storage locations in the carousel 24 are available for the canister 26 (block 628). If no carousel 24 location can be found for a specific canister 26, the controller 18 will inform the operator 22 that no locations could be found in the canister's carousel 24 and zone and will ask the operator 22 if a new storage location should be chosen (e.g., in a different zone or carousel 24) (block 630). If the operator 22 does not want to choose a new storage location, the controller 18 will display an error to the operator regarding no storage location being available (block 632) and will wait on correction, such as by waiting for an inventory operator to remove a canister 26 from the carousel 24 so a location can open up. Meanwhile, the controller 18 may return to step 624 to prompt the operator 22 to scan another canister 26.

If the operator 22 answers Yes to choosing a new storage location at step 630, or if a storage location is available in the carousels 24 at step 628, the light panel 28 will turn on for the appropriate shelf of the chosen carousel 24 to identify the storage location (block 634). As with other operational steps described herein, the indicator panel 28 and the display monitor 36 will each show the location on the carousel 24 where the canister 26 should go. The controller 18 will prompt the operator 22 to go to the storage location and scan the storage location (block 636). The operator 22 should take the canister 26 from the cart, go to the carousel 24, and manually spin the carousel 24 so the specified position is visible. The operator 22 should then scan the location to verify that he/she is at the right location in the carousel 24. The controller 18 determines whether the scanned location is the correct storage location for the canister 26 (block 638). If the scanned location is not correct, the controller 18 displays an error to the operator 22 about the wrong location being scanned (block 640) and returns to step 636 to prompt a scan again. Once the correct location has been scanned, the operator 22 will be prompted to scan the canister 26 (block 642). Although the operator 22 scanned the canister 26 when it was removed from the staging bar 32, this extra scan is used to make sure the operator 22 still holds the correct canister 26. This process of scanning the location and then scanning the canister 26 will be reused consistently in all phases of the operational process. The controller 18 then determines if the scanned canister 26 is correct (block 644). If the scanned canister 26 is incorrect, the controller 18 displays an error to the operator 22 regarding the wrong canister 26 being scanned (block 646) and returns to step 642 to prompt another scan of the canister 26. Once the correct location and the correct canister 26 have been scanned, the controller 18 extinguishes the light tree 28 and the operator 22 places the canister 26 in the storage location.

The controller 18 then determines if there are anymore removed canisters 26 left to be replaced in the carousels 24 (block 650). If there are any more canisters 26 that had previously been removed from the staging bar 32, the controller 18 returns to step 624 and the operator 22 will be directed to scan another canister 26, such that the return process of operations is repeated for that canister 26. If there are no canisters 26 left that were removed from the staging bar 32 at step 650, the canister exchange cycle 534 ends and the controller 18 progresses to the batch picking cycle 536 to pull new canisters 26 from the carousel 24 and place them on the staging bar 32.

Figure 25A:
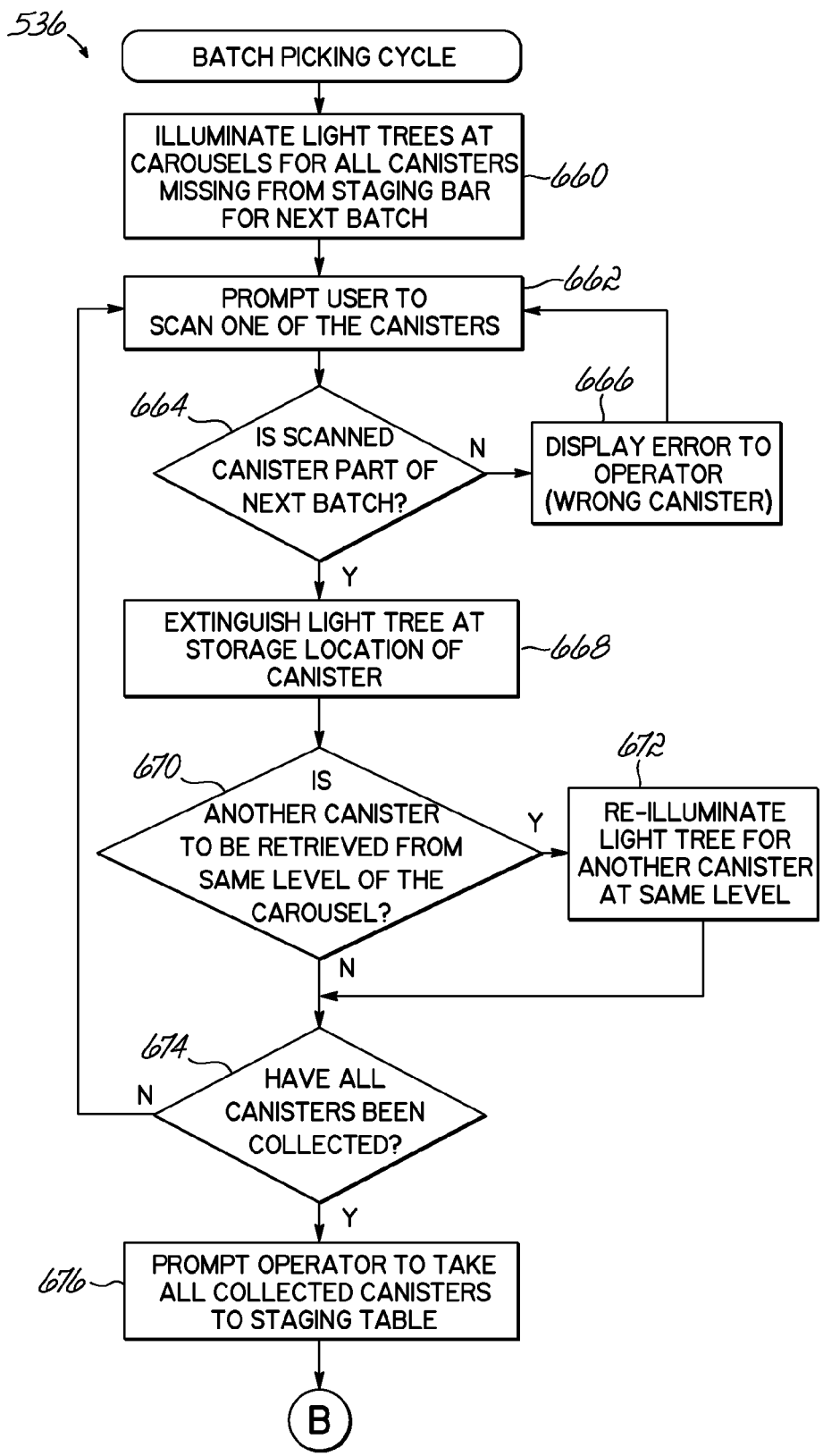
FIG. 25A is a flowchart showing a sequence of operations that may be performed during the batch picking cycle of FIG. 21.
Figure 25B:
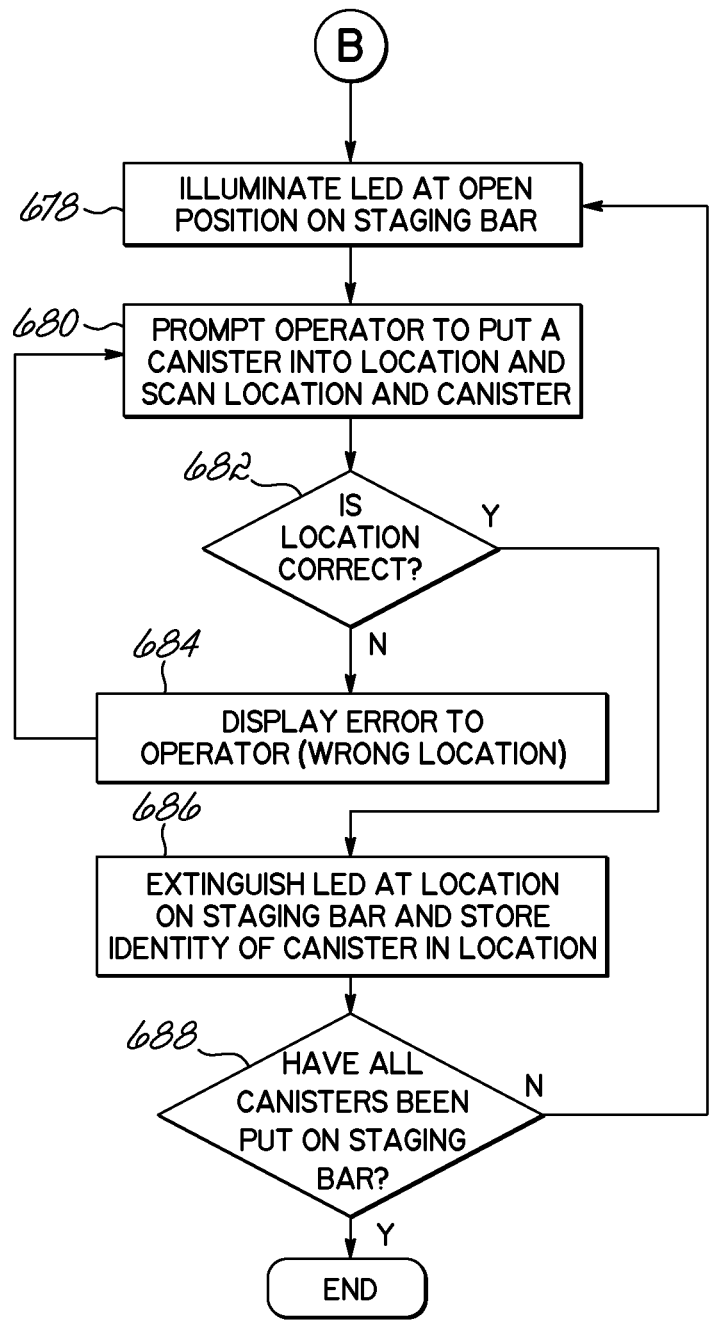
FIG. 25B is a flowchart showing a further sequence of operations that may be performed during the batch picking cycle of FIG. 25A.

With reference to FIGS. 25A and 25B, the series of operations defining the batch picking cycle 536 are shown in further detail. This cycle 536 will be similar to the canister exchange cycle 534 described above in that the operator 22 will pull all needed canisters 26 from the carousels 24, and then take all canisters 26 to the staging bar 32 and put the canisters 26 into staging bar 32 locations. The display monitor 36 will again show the operator 22 what step is being performed at any given time during the batch picking cycle 536.

The controller 18 will have previously identified which medications and canisters 26 are needed for the next batch. If a medication is found that does not have a canister 26 in the staging bar 32, or has a canister 26 with insufficient inventory in the canister 26 to fulfill the filling of the medicament pass, the system will choose a canister 26 for that medication to pull from the carousel 24. It will be appreciated that at least one canister 26 for that medication must have been in the carousel 24 at the time of order retrieval; otherwise the batch would not have been created in the first place because an inventory check was performed at that step. If more than one canister 26 is found that contains the required drug, the canister 26 containing medication with the earliest expiration date will be chosen.

Once the system has chosen the list of canisters 26 needed from the carousel 24, the controller 18 will illuminate the indicator panels 28 for the appropriate shelves of the appropriate carousels 24 for all of the needed canisters 26 simultaneously (block 660). The controller 18 will also prompt the operator 22 to select and scan one of the canisters 26. Each illuminated indicator panel 28 will tell the location on the carousel 24 where the operator 22 should go to retrieve a canister 26. If two or more canisters 26 are needed from the same carousel 24 and shelf, i.e. they would both use the same location on the same indicator panel 28, then the controller 18 will turn on that indicator panel 28 with the location for a first of the canisters 26. Once the first canister 26 is retrieved, as described in the next paragraph, the controller 18 will change the panel's display to indicate the carousel location for the other canister 26.

The operator 22 should go to one of the illuminated carousels 24, manually spin the carousel 24 to the specified location, and retrieve the canister 26 there. The operator 22 should then scan the canister 26 at that location. The controller 18 will verify if the canister 26 scanned was in the list of canisters 26 to be removed (block 664), and emit an error signal to the operator about scanning a wrong canister 26 if not (block 666). If the scan was of a correct canister 26, the controller 18 will extinguish the indicator panel 28 at that location (block 668). As described previously, the controller 18 determines if another canister 26 on the same level is to be retrieved (block 670). If another canister 26 needed for the batch uses the same location on the indicator panel 28, the panel 28 will immediately turn back on with the location for the other canister 26 (block 672). The controller 18 checks after each verified scan whether all canisters 26 have been collected for the batch (block 674). Thus, the operator 22 will repeat the above process of picking canisters 26 from carousel locations until all indicator panels 28 have been extinguished.

Once all light trees 28 have been extinguished, the operator 22 can put the canisters 26 that were removed to locations on the staging bar 32. The controller 18 will choose a location on the staging bar 32 that does not currently have a canister 26 assigned, and activate the LED at that location (block 678). For example, the LED at that location will blink green, and the associated display will read "Put." The controller 18 will also prompt the operator 22 to put a canister 26 in that location and then scan the location and the canister 26 (block 680). The operator 22 should place the canister 26 in that staging bar 32 location, and then scan the location, followed by the canister 26, with the controller 18 validating at each scan. To this end, the controller 18 determines whether the scanned location is correct (block 682). If the location is incorrect, an error is displayed to the operator about the wrong location (block 684); otherwise, the scanned canister 26 will be associated to the location. At that point, the LED on the staging bar 32 will be deactivated or extinguished by the controller 18 and the location of the canister 26 stored in local memory (block 686). The controller 18 then checks whether all canisters 26 have been put on the staging bar 32 from the batch picked from the carousels 24 (block 688). If more canisters 26 require placement on the staging bar 32, the controller 18 returns to step 678 and repeats the process for all canisters 26 that were removed from the carousels 24. Once all required canisters 26 are in the staging bar 32, the controller 18 ends the batch picking cycle 536 and moves onto the next step of counting out pills from one of the canisters 26.

It will be understood that if the controller 18 requires more canisters 26 than available locations on the staging bar 32, the controller 18 will direct the operator 22 to pick only as many canisters 26 from the carousels 24 as will fit on the staging bar 32. The controller 18 will then direct the operator 22 to put those canisters 26 to the staging bar 32, which will fill all staging bar 32 locations. The controller 32 will operate the counting and filling steps for the batch with the canisters 26 that have been picked, but another canister exchange cycle 534 and batch picking cycle 536 will need to be performed later during the same batch, before moving onto the next batch.

In some circumstances, it is possible for a canister 26 to be in the carousel 24 at the time the batch request is made and the order is retrieved, but before the operator 22 gets to the picking step, a replenishment operator takes the canister 26 out of the carousel 24. This circumstance may happen because replenishment of canisters 26 in the carousels 24 may generally occur at the same time the carousels 24 are being used to fill orders. There are two possible scenarios in these circumstances. The first scenario is where the replenishment operator has removed the canister 26 before the controller 18 turns any of the indicator panels 28 on, for example during the replacing of unneeded canisters 26 back into the carousels 24. In that case, the controller 18 will know at the time of turning on the indicator panels 28 which canisters 26 still have valid carousel locations, and will only turn those lights on. If no canisters 26 in the batch have valid carousel locations, then the controller 18 will provide an error indication (including a red indicator panel on the display monitor 36), and the operator 22, after waiting for a replenishment operator to put the canister 26 back into the carousel 24, will click a Retry button on the display monitor 36 to retry the picking operation.

The second scenario is if the canister 26 is removed by the replenishment worker after the indicator panel 28 is already on. This scenario could happen, for example, if the system turns on multiple indicator panels 28, and the operator 22 goes to pick the first canister 26, but the replenishment operator pulls the second canister 26 from the carousel 24. Then when the operator 22 arrives at the second illuminated location, there will be no canister 26 in that location (or potentially even a different canister 26). To remedy this situation, the display monitor 36 will have a button to start positioning the canisters 26 on the staging bar 32 that have been scanned. The operator 22 can then skip the location with a problem and move on to other locations, scanning the canisters 26 as normal. When the operator 22 gets back to the staging bar 32, not all of the canisters 26 will have been scanned, so the controller 18 will still be waiting for a canister scan. The operator 22 can instead click an override button on the display monitor 36 to start positioning canisters 26 on the staging bar 32. The controller 18 will then enable the operator 22 to take only those canisters 26 removed from the carousel 24, put those canisters 26 to the staging bar 32 using the normal process, and then return to the picking process. At that time, the controller 18 will recheck the location of any canisters 26 still needed to determine if they are now in a carousel 24 again or if they are still at a replenishment workstation, in which case the operator 22 will be forced to wait as described above.

Figure 26A:
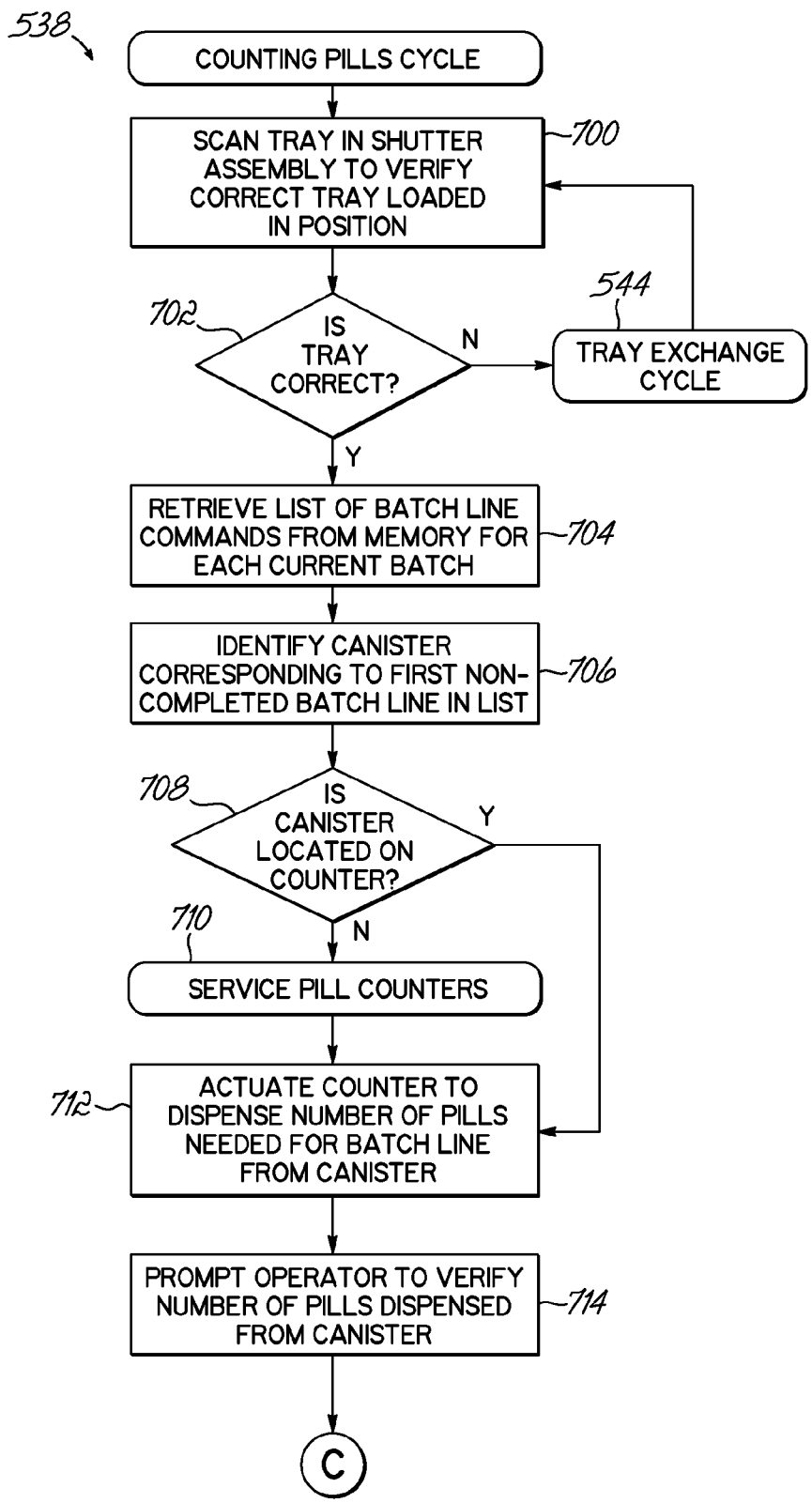
FIG. 26A is a flowchart showing a sequence of operations that may be performed during the counting pills cycle of FIG. 21.
Figure 26B:
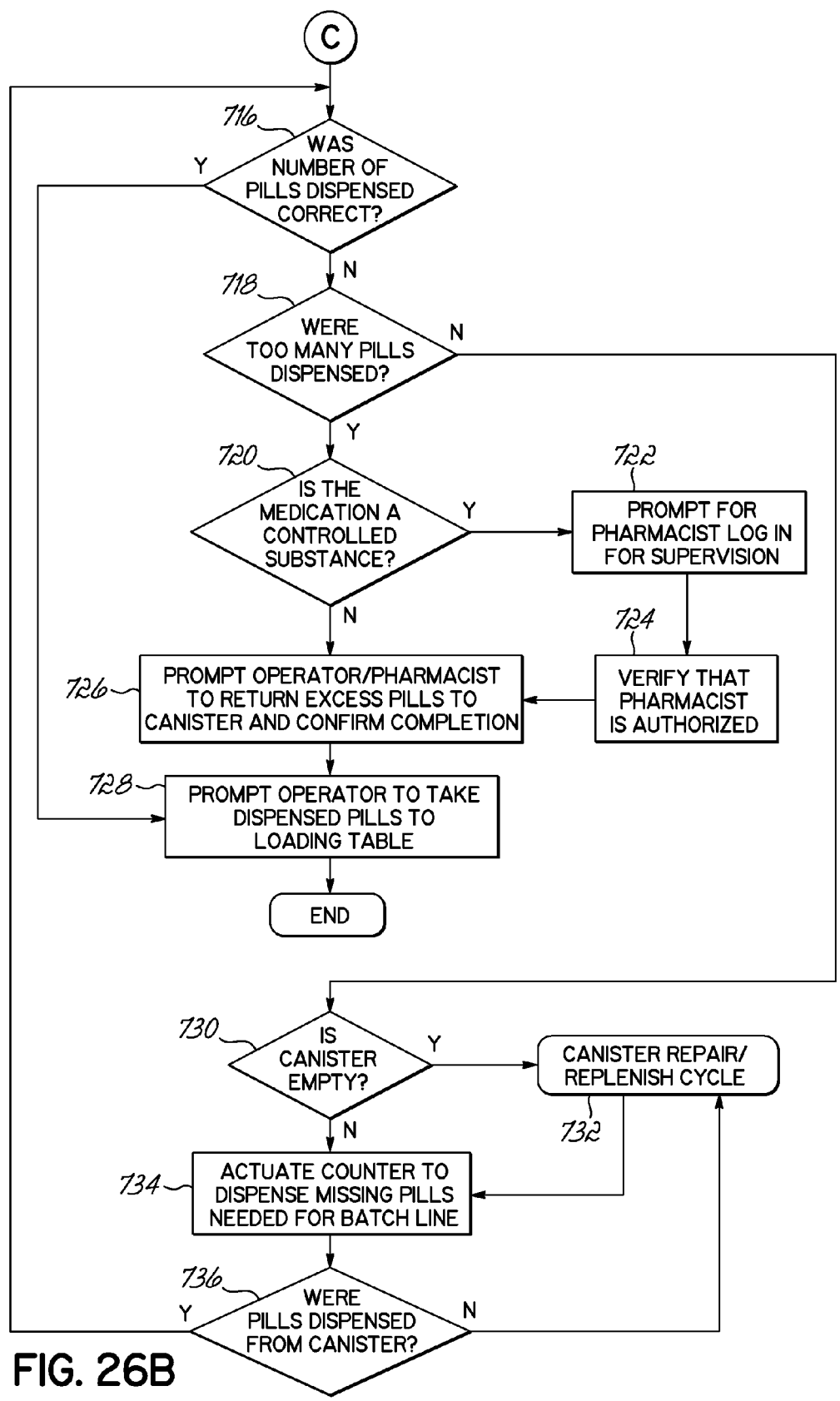
FIG. 26B is a flowchart showing a further sequence of operations that may be performed during the counting pills cycle of FIG. 26A.

With reference to FIGS. 26A and 26B, the series of operations defining the counting pills cycle 538 is shown in further detail. The controller 18 begins this cycle 538 by scanning the tray 40 within the shutter assembly 38 at the loading table 30 to verify if the correct tray for this batch is in position (block 700). If the controller 18 determines that the tray 40 is incorrect (at block 702), the controller 18 will actuate the tray exchange cycle 544 to replace the tray 40 as described in further detail with reference to FIG. 31 below. If the tray 40 is validated, the controller 18 will maintain the tray 40 locked in the shutter assembly 38 and will retrieve a list of batch line commands from memory pertaining to the current batch being filled (block 704). Now the controller 18 will effectively execute the batch file one batch line at a time. The batch file was created when the batch was started and consists of multiple batch lines. Each medication to be used in filling the blister packs 90 is assigned a different batch line. Also, the same medication would require two batch lines if that medication is taken from two canisters 26 because one canister 26 does not have enough inventory. Further, the same canister 26 would require two batch lines if it is going into two different compartments 94 of the blister packs 90 because the patient needs to take two of that pill for the order. The combination of canister 26 and compartment 94 number uniquely identifies a batch line.

The controller 18 will identify the first non-completed batch line in the list of the batch file, and locate the canister 26 on the staging bar 32 that corresponds to that batch line (block 706). The controller 18 will determine if the canister 26 is on the counter 34 already (at block 708) and will actuate a service pill counters cycle (block 710) if the canister 26 is not on the staging bar 32. At this point, the dispensing of pills by the counter 34 can occur. Initially, this will be done by an operator 22 manually typing into the pill counter 34 the number of pills needed. In that case, the controller 18 will tell the operator 22 on the display monitor 36 the number of pills required. Alternatively, and as shown in FIGS. 26A and 26B, the controller 18 automatically sends a command to the pill counter 34 to automatically dispense the proper number of pills needed for the batch line from the canister 26 (block 712). Therefore the system will have a parameter that tells whether the counters 22 will dispense manually or by a message sent from the software to the counter 22.

The controller 18 will then prompt the operator to verify the number of pills that were dispensed from the canister 26 (block 714). Depending on the number of pills input by the operator 22, the controller 18 determines whether the number of pills dispensed was correct (block 716). If the count of pills dispensed is not correct, the controller 18 will determine whether too many pills were dispensed (block 718) and will take different actions depending on whether the actual number of pills dispensed is less than or more than the number of pills requested. If the number of dispensed pills is less than the requested amount, then the controller 18 may be able to request more pills to complete the transaction. If the number of dispensed pills is more than the requested amount, then the controller 18 will guide the operator 22 to replace the excess stock.

If the controller 18 determines that too many pills were dispensed at step 718, the controller 18 will check to see if the medication is a controlled substance (block 720). If the medication is a controlled substance, then the controller 18 will prompt the operator 22 for a pharmacist (RPh) login by entry of an RPh username and password (block 722). This prompt will be generated even if the process is configured to require a pharmacist login at startup for overseeing the process, and the pharmacist that logs in at this step does not need to be the same as the one logged in to oversee the process. Once the operator 22 has contacted a pharmacist and the pharmacist has logged in, the controller 18 will verify that the pharmacist is authorized to confirm movements of controlled substances (block 724). The controller 18 will tell the pharmacist the quantity of the medication that needs to be returned to the canister 26 and prompt the pharmacist to return that quantity to the canister 26, then confirm this return (block 726). If, on the other hand, the medication is not controlled, the controller 18 can bypass the pharmacist login step and simply prompt the operator 22 to return the necessary amount to the canister 26 at step 726. It will be understood that in either case the canister inventory will be decreased by the required amount of the product. Once the pharmacist or operator 22 has confirmed that the product has been returned to the canister 26, then the controller 18 can update the inventory management application of the return of stock accordingly. The controller 18 then proceeds to prompt the operator to take the dispensed pills to the loading table (block 728) and goes to the filling blister packs cycle 540 described in detail below.

If the controller 18 determines that not enough pills were dispensed at step 718, the controller 18 will prompt the operator 22 to check to see whether the canister 26 is empty (block 730). If the operator 22 answered "Yes," i.e. the canister 26 is empty, the canister 26 will have to be replenished. In that case the system will adjust the canister inventory quantity to 0 and a canister repair/replenishment service (block 732) will be performed as described below with reference to FIGS. 28A and 28B. If the operator 22 answers "No" (or after replenishment is complete at step 732), the controller 18 will send a new command to actuate the counter 22 to dispense the remaining quantity (block 734), and again check the feedback from the counter 22 to see if the number of dispensed pills is now correct (block 736). If the count is still not correct, then the controller 18 will actuate the canister repair/replenishment service 732 as described above. If the count is now corrected, then the controller 18 returns to step 716 to verify again that the total number of pills counted out is correct before prompting the operator 22 to take those pills to the loading table.

Figure 27A:
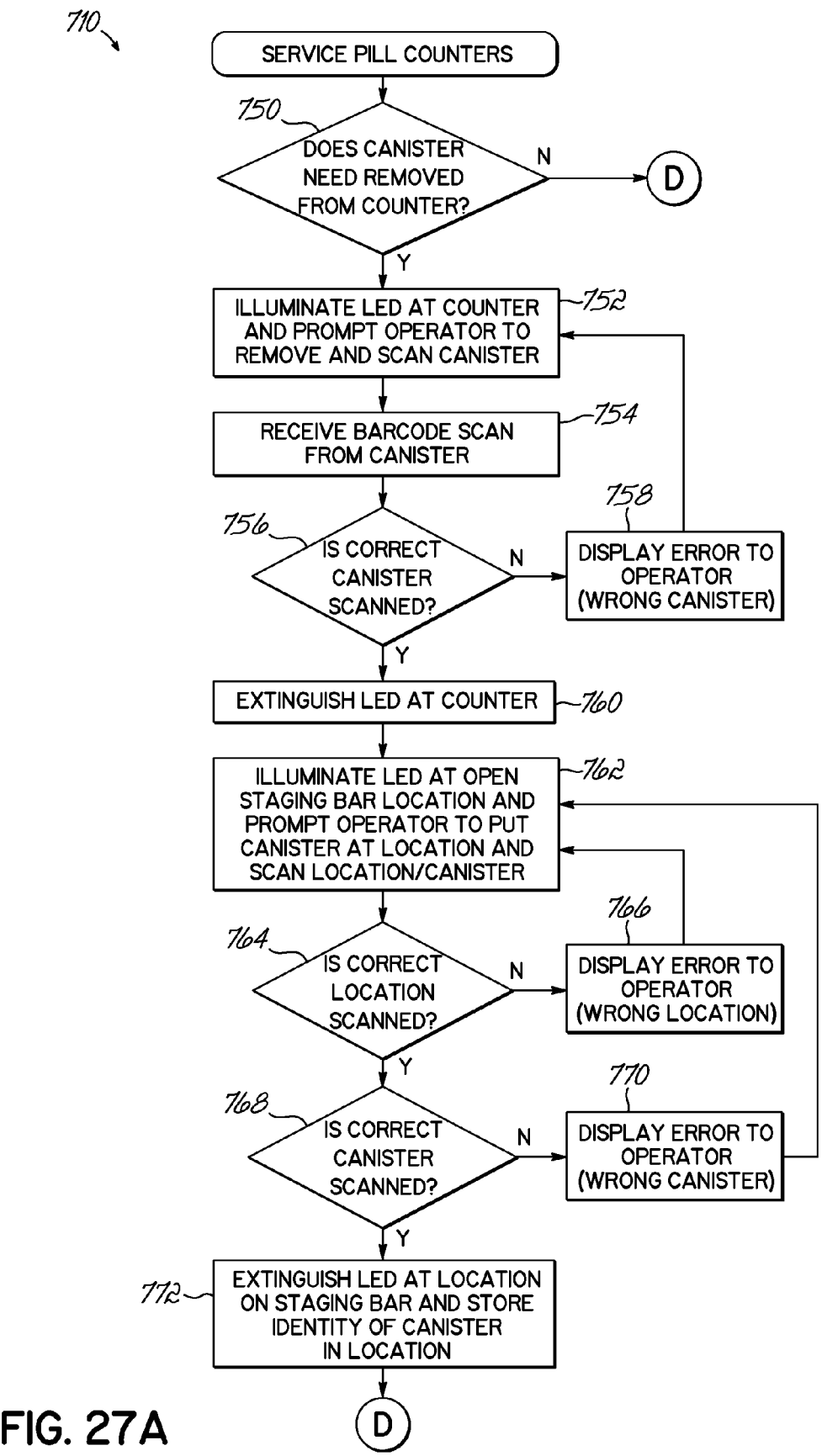
FIG. 27A is a flowchart showing a sequence of operations that may be performed during the service pill counters cycle of FIG. 26A.
Figure 27B:
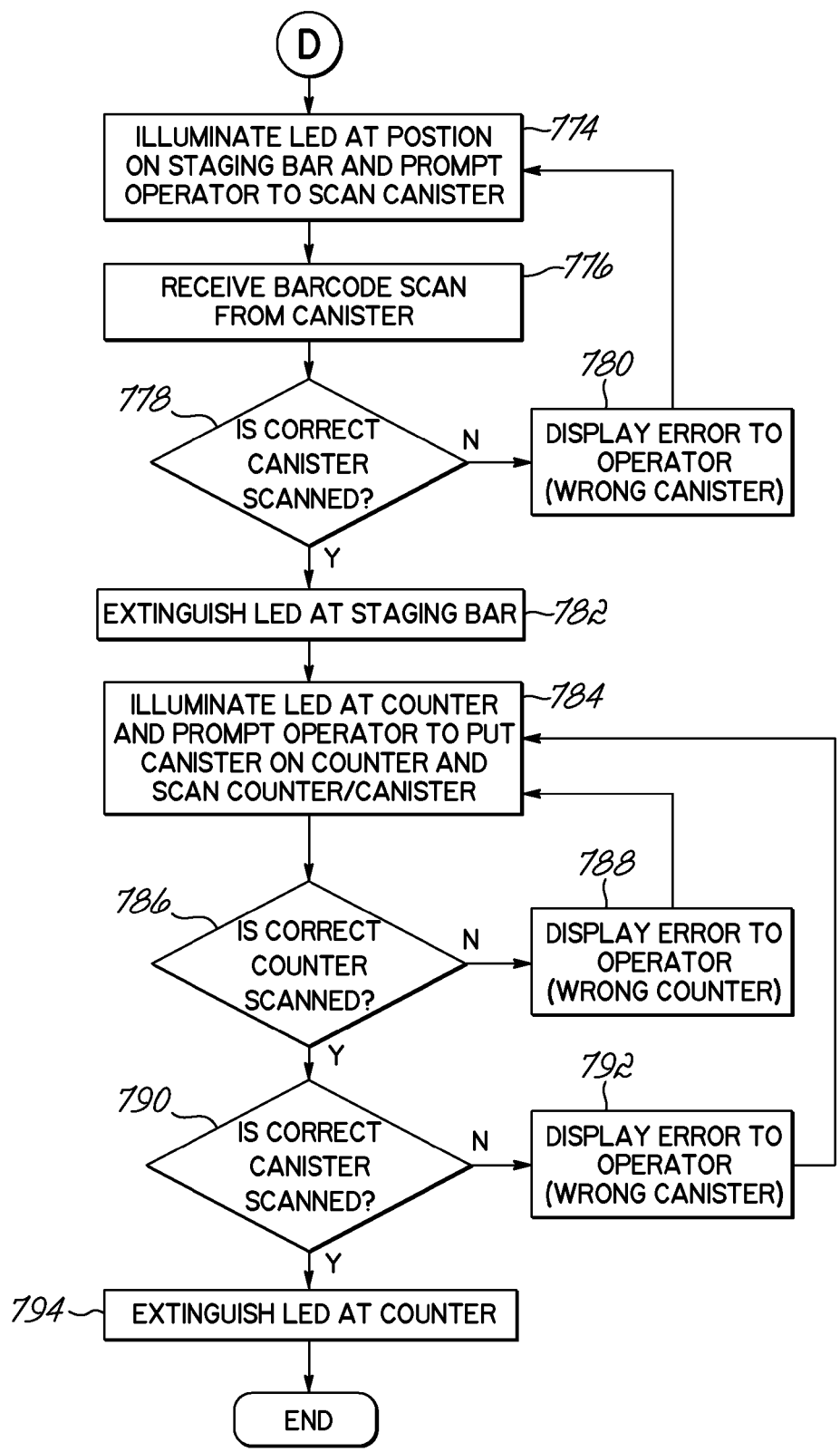
FIG. 27B is a flowchart showing a further sequence of operations that may be performed during the service pill counters cycle of FIG. 27A.

The series of operations collectively defining the aforementioned service pill counters cycle 710 is shown in further detail in FIGS. 27A and 27B. In this regard, the controller 18 begins by determining if a canister 26 needs to be removed from the counter 34 (block 750). If a canister 26 does need to be removed from the counter 34, then the controller 18 will illuminate the light at the counter 34 in red and will prompt the operator 22 to remove and scan the canister 26 by reading "Scan" (block 752). The controller 18 will then receive the barcode scan from the operator 22 of a canister 26 (block 754). The controller 18 then determines whether the correct canister 26 was scanned (block 756), and an error is displayed to the operator 22 regarding the incorrect canister 26 being scanned if the verification fails (block 758). Once the correct canister 26 has been scanned, the controller 18 extinguishes the LED at the counter 34 (block 760) to indicate the correct canister 26 has been removed.

The controller 18 then activates or illuminates the LED light at an open location on the staging bar 32 in green and prompts the operator 22 to put the canister 26 at that location and scan the location and the canister 26 (block 762). Once the scan of the location has been received, the controller 18 verifies if the correct location has been scanned (block 764) and will then display an error to the operator 22 regarding the wrong location if the location scanned is incorrect (block 766). If the location scanned is correct, the controller 18 will verify whether the correct canister 26 was scanned in the location (block 768). If this verification fails, the controller 18 displays an error to the operator 22 regarding the wrong canister 26 being scanned (block 770) and waits for another scan at step 762. Once the correct location and canister 26 have been scanned and verified by the controller 18, then the controller 18 extinguishes the LED at the location on the staging bar 32 and stores the identity of the canister 26 in that location in local memory (block 772). The controller 18 is then ready to put a new canister 26 on the pill counter 34.

At this point, or if no canister 26 needs removed at step 750 described above, the controller 18 will illuminate the light at the next canister's location on the staging bar 32 in red, and the display adjacent the canister 26 will prompt the operator 22 to remove and scan the canister 26 by reading "Scan" (block 774). The operator 22 should take the canister 26 from the staging bar 32 and scan it. The controller 18 will receive the barcode scan of the canister 26 from the operator 22 (block 776). The controller 18 will then verify that the correct canister 26 was scanned (block 778), displaying an error to the operator 22 regarding the wrong canister 26 being scanned if not correct (block 780). The controller 18 will then return to step 774 to prompt the scan of the correct canister 26. If the scan was correct, the controller 18 will extinguish the light on the staging bar 32 (block 782).

The controller 18 will then illuminate the light at one of the pill counters 34 (block 784). For example, the pill counter light 34a will flash an associated LED green and a counter display will read "Put" to prompt the operator to put the canister 26 on the counter 34 and scan the canister 26 and the counter 34. Once the scan of the location has been received, the controller 18 verifies if the correct counter 34 has been scanned (block 786) and will then display an error to the operator 22 regarding the wrong counter 34 if the counter 34 scanned is incorrect (block 788). If the counter 34 scanned is correct, the controller 18 will verify whether the correct canister 26 was scanned at the counter 34 (block 790). If this verification fails, the controller 18 displays an error to the operator 22 regarding the wrong canister 26 being scanned (block 792) and waits for another scan at step 784. Once the correct counter 34 and canister 26 have been scanned and verified by the controller 18, then the controller 18 extinguishes the LED at the counter 34 (block 794) and the service pill counters cycle 710 ends.

It will be understood that there may be two pill counters 22 at the manual packaging station 14: one for full pills and one for partial pills. If all the pills for the current batch line are full pill quantities, then the controller 18 will direct the operator 22 to put the canister 26 on the first counter 34. If all the pills for the current batch line are partial pill quantities less than one, then the controller 18 will direct the operator 22 to put the canister 26 on the second counter 34. If the pill quantities are a combination, such as quantities of 1.5, or where some blister packs 90 will get a full pill and some will get a fraction of a pill, then the batch line will be split. The controller 18 will first direct the operator 22 through the complete process for the drug using the integral quantities, including putting the canister 26 back on the staging bar 32 when done. Later, the system will direct the operator 22 to pull the same canister 26 from the staging bar 32 and process it again for the fractional quantities at the other counter 34 (thereby performing two service pill counters cycles 710).

Figure 28A:
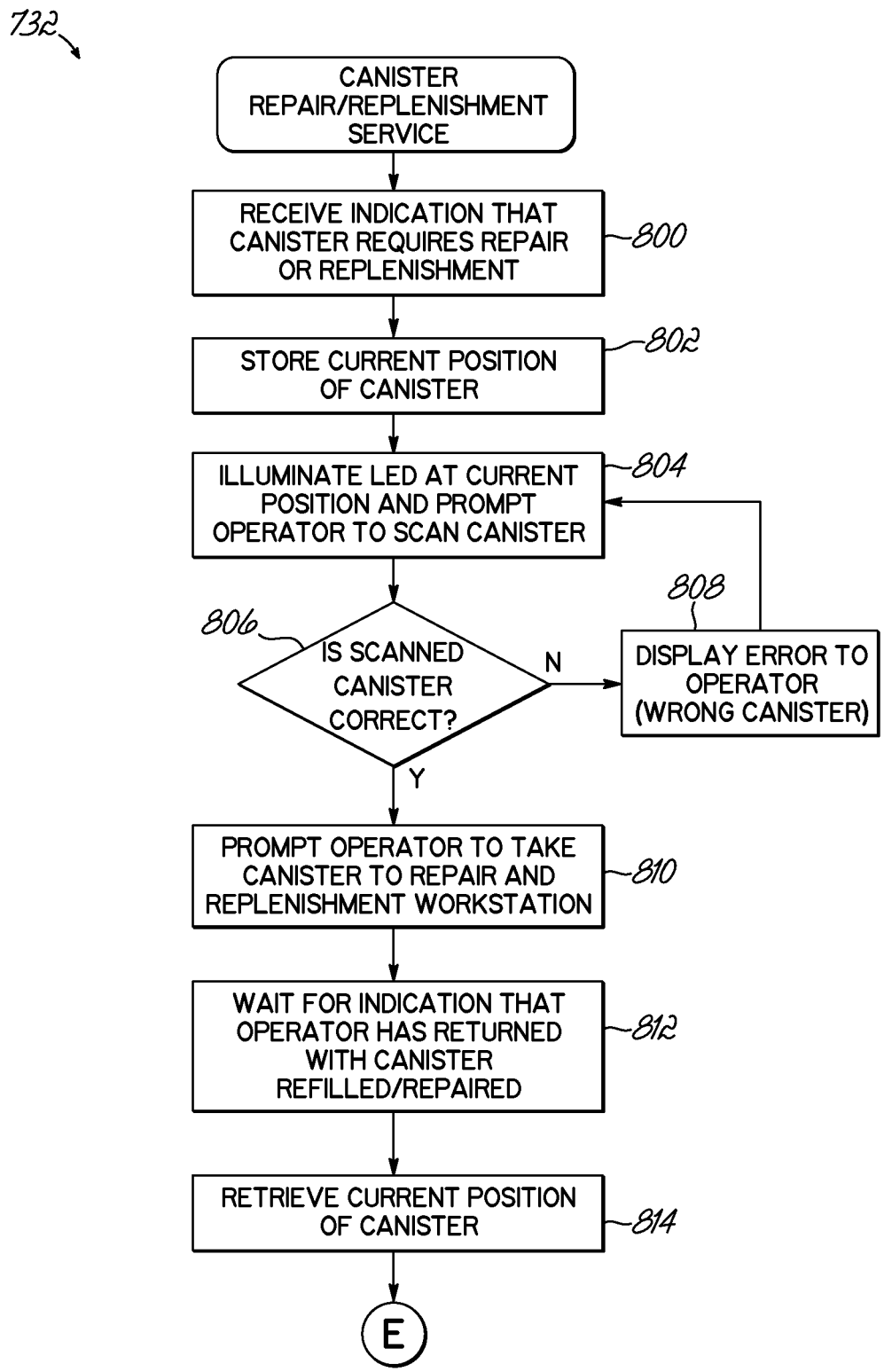
FIG. 28A is a flowchart showing a sequence of operations that may be performed during the canister repair/replenishment service cycle of FIG. 26A.
Figure 28B:
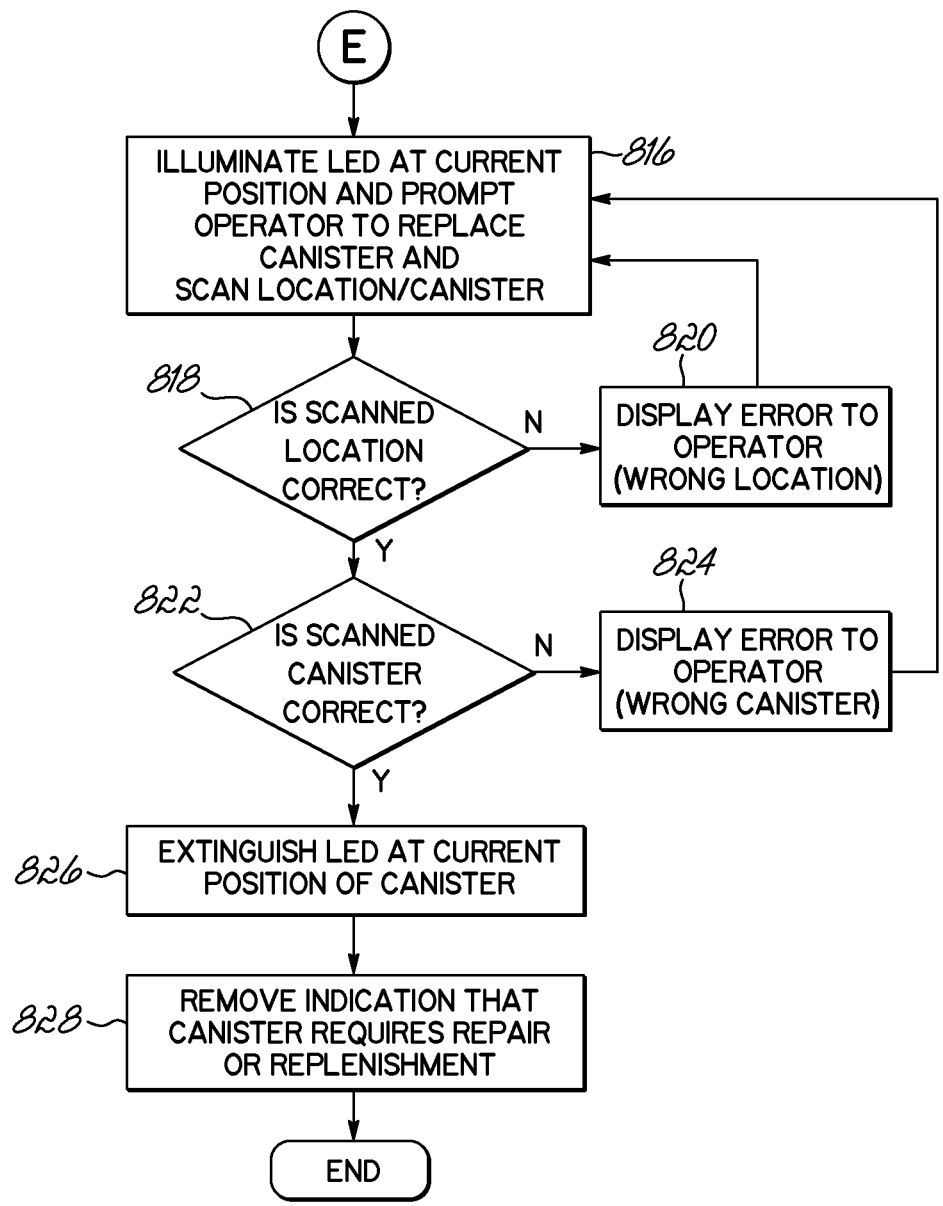
FIG. 28B is a flowchart showing a further sequence of operations that may be performed during the canister repair/replenishment cycle of FIG. 28A.

The series of operations defining the canister repair/replenishment service cycle 732 is shown in further detail with reference to FIGS. 28A and 28B. The controller 18 will receive an indication that a canister 26 requires repair or replenishment of stock (block 800). For example, during the previously-described counting pills cycle 538, this indication will come when the controller 18 determines that a canister 26 is empty or when the canister 26 will not dispense the required number of pills at the pill counter 34. When such an indication is received, the controller will store the current position of the canister 26 (block 802) and then the controller 18 will then turn on the light at the current position, with its LED flashing red and its display reading "Scan" (block 804). At this point the operator 22 should take the canister 26 from its current location and scan the canister 26 to verify that the correct canister 26 is being taken. The controller 18 then verifies if the correct canister 26 was scanned (block 806). If the scan fails to validate the correct canister 26, then the controller 18 displays an error to the operator 22 about the wrong canister 26 being scanned (block 808) and the controller 18 waits for another scan. If the scan is verified to be correct, the light will turn off at the current location and the controller 18 will prompt the operator 22 to take the canister 26 to a repair and replenishment station. Next, the operator 22 needs to perform a repair or replenishment to the canister 26 (not described in detail herein because this occurs at an unrelated station to the manual packaging station 14).

Once the operator 22 has completed the replenishment to the canister 26, he can confirm on the display monitor 36 that the replenishment is completed (block 812). Once this indication is provided to the controller 18, the controller 18 retrieves the saved current position of the canister 26 (block 814). The controller 18 also illuminates the light for the current location and prompts the operator 22 to return the canister 26 and to scan the location and the canister 26 by making the LED flash green and the display read "Put" (block 816). The operator 22 should put the canister 26 at the desired current location and follow the standard process of scanning the location barcode, followed by the canister 26. The controller 18 determines if the correct location is scanned (block 818) and displays an error to the operator 22 regarding the incorrect location if the validation fails (block 820). The controller 18 also determines if the correct canister 26 is scanned (block 822) and displays an error to the operator 22 regarding the incorrect canister 26 if the validation fails (block 824). Once the validation passes, the controller 18 extinguishes the light on the current location (block 826). The controller 18 will then remove the indication that the canister 26 requires repair or replenishment (block 828) and returns to the previous actions in progress, e.g., the canister repair/replenishment service 732 ends.

Figure 29A:
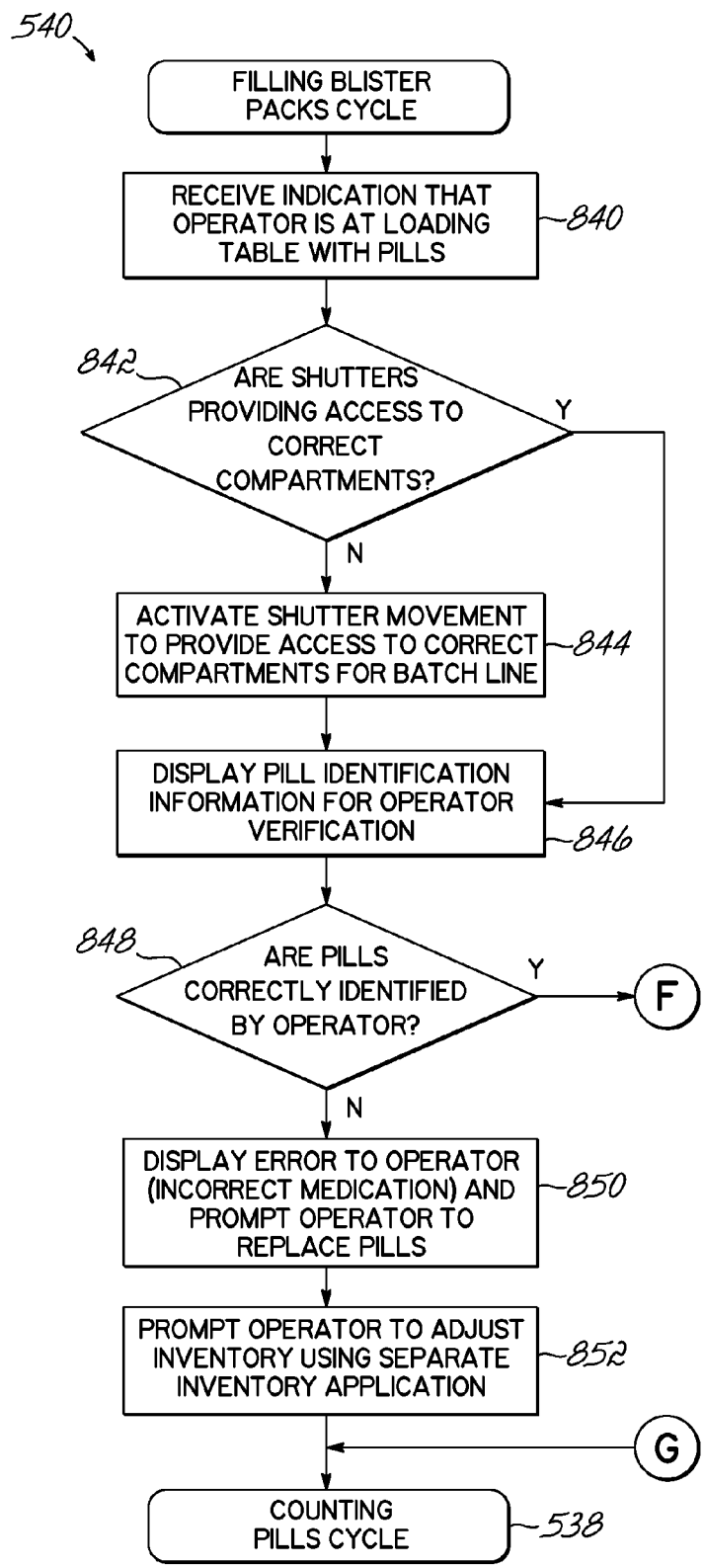
FIG. 29A is a flowchart showing a sequence of operations that may be performed during the filling blister packs cycle of FIG. 21.
Figure 29B:
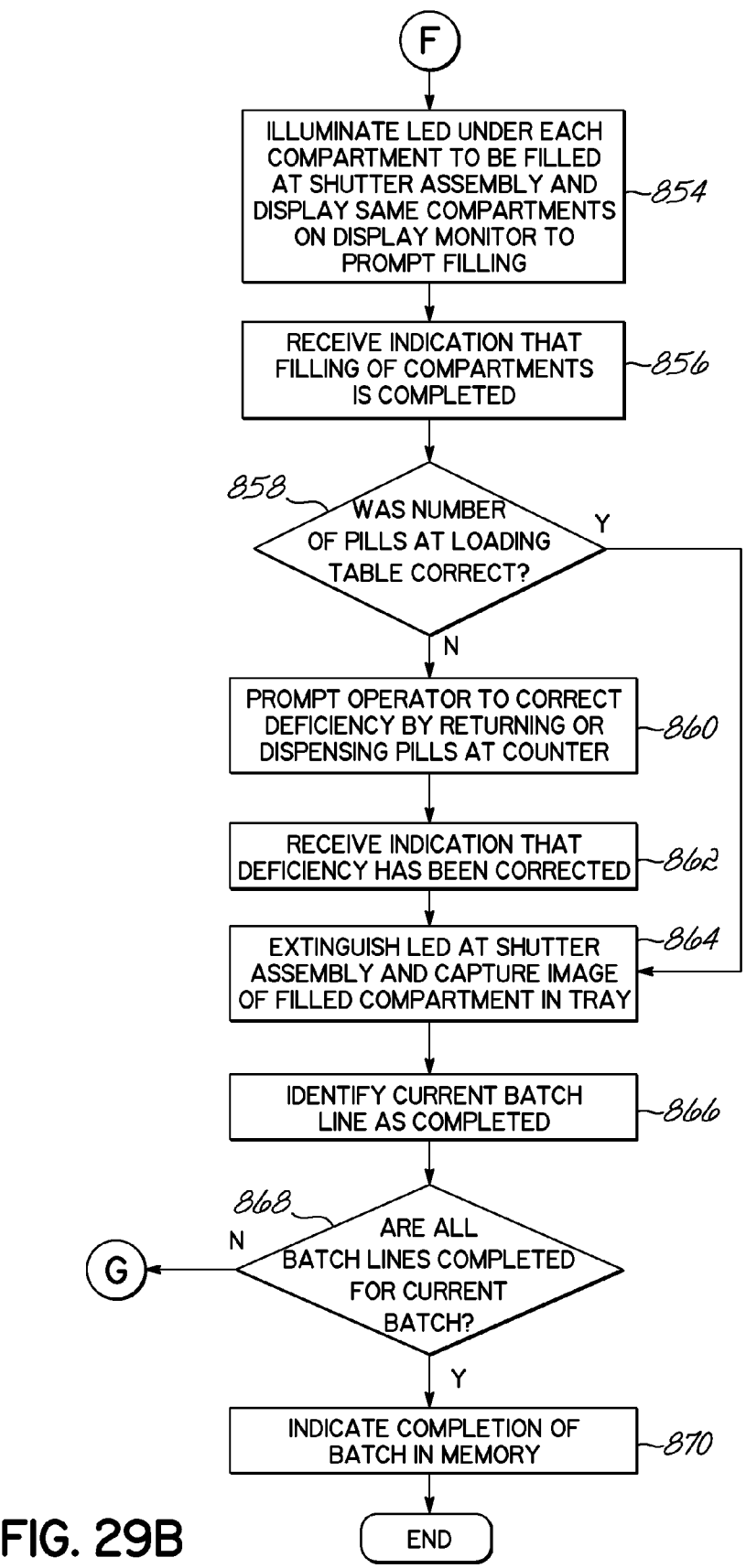
FIG. 29B is a flowchart showing a further sequence of operations that may be performed during the filling blister packs cycle of FIG. 29A.
Figure 30:
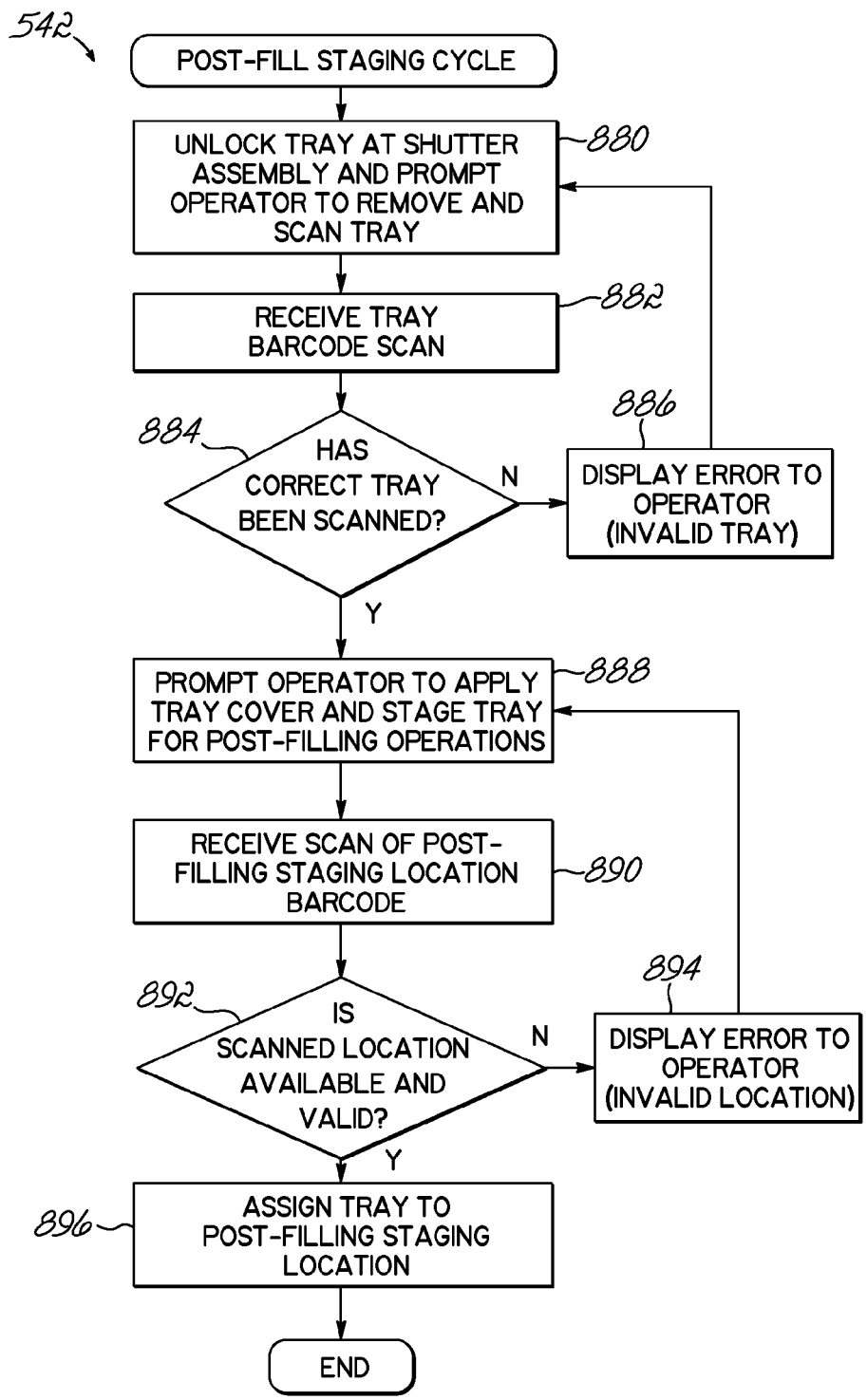
FIG. 30 is a flowchart showing a sequence of operations that may be performed during the post-fill staging cycle of FIG. 21.

With reference to FIGS. 29A and 29B, the series of operations defining the filling blister packs cycle 540 is illustrated in further detail. At this point in the overall filling process, the operator 22 has put a canister 26 on a pill counter 34, which has dispensed the proper quantity of a pill for what is required by the blister packs 90 currently on the tray 40 at the loading table 30. The operator 22 is now ready to place those pills into the blister packs 90. The controller 18 will receive an indication that the operator 22 is at the loading table 30 with the pills (block 840). The controller 18 will then determine if the shutters 174 are providing access to the correct compartments 94 for those pills at the loading table 30 (block 842). If not, then the controller 18 actuates movement of the shutter gears 174 to provide access to the correct compartment 94 for the current batch line (block 844). The shutter 174 will then move to the correct position, and report back to the software when completed (such as via the stepper motor 196 or the detection of the placement gear 198). If the shutter 174 cannot move to that position because of an error, an error message will be reported to the software and displayed on the display monitor 36. The operator 22 should correct any issue that is keeping the shutter 174 from moving (such as the shutter 174 is not turned on) and click the Retry button on the display monitor 36. The system will then try again to move the shutter 174 to the correct position.

Once the shutter 174 has moved to the correct position, the display monitor 36 will show the appearance attributes of the drug that is being filled, such as by a picture or a written description (block 846). The controller 18 will query the operator 22 if the displayed drug information matches the drug that has been dispensed by the canister 26 (block 848). If the operator 22 answers "Yes," then the display monitor 36 and the shutter assembly 38 can instruct the operator 22 where to put the pills, as described in the next paragraph. If the operator 22 answers "No," the controller 18 will display an error message to the operator 22 regarding the incorrect medication and will instruct the operator 22 to correct the pills dispensed (block 850). The controller 18 will also prompt the operator 22 to adjust the inventory of the pills in the canisters 26 affected by using a separate inventory application not described in detail herein (block 852). In this case, the controller 18 will return to the counting pills cycle 538 to assist with replacing the canister 26 with the correct medication canister 26 and to re-dispense the correct medication for filling the blister packs 90.

Once the operator 22 confirms that he has the correct medication at step 848, the controller 18 will indicate where in the blister packs 90 the medications should be filled. The display monitor 36 will show which of the blister packs 90 are to receive the drug by highlighting the relevant compartments 94 with the same color as LEDs 218 that illuminate under the specific desired compartments 94 (block 854). To this end, the software will tell the operator 22 if a particular compartment 94 gets 1 pill, ½ of a pill, or no pills. It will be appreciated that for each filling pass, the pills will all be going into the same compartment 94 of each required blister pack 90, so the shutter 174 will be opened on all blister packs 90 to the same compartment 94. The shutter assembly 38 will include at least one LED 218 under each compartment 94 of each blister pack 90 as previously described. In one exemplary operation, when activated, the color of the LED 218 indicates the quantity for the compartment 94. If the LED and display monitor 36 are green, it means the compartment 94 requires a full pill. If the LED and display monitor 36 are red, it means the compartment 94 needs a partial pill, and the display monitor 36 will show the precise fraction of a pill that is required. Alternatively, in another exemplary operation, the color of the LED is emitted at a frequency that will provide maximum contrast to the pill color and the color of the blister pack 90, when appropriate. This frequency could change from batch line to batch line because different frequencies of light energy will better contrast against pills of different colors. The specific color of the LEDs 218 and the compartments 94 on the display monitor 36 may be modified without departing from the scope of the embodiments of the invention.

The operator 22 should then place the pills into the specified compartments 94. When all pills have been placed, the operator 22 can confirm whether the fill completed correctly or if there was a discrepancy in the number of pills. The controller 18 receives the indication that the filling of compartments 94 if completed (block 856), and then determines whether the number of pills at the loading table 30 was correct (block 858). If there was a discrepancy from the number of pills needed, the controller 18 prompts the operator 22 to specify whether the actual number of pills was more than or less than the required number and then prompts the operator 22 to correct the deficiency (block 860). If the pill count was more than what was required, i.e. there are extra pills left over, the operator 22 must put those pills back into the canister 26. This process is the same as described previously in the pill counting cycle. If the pill count was less than what was required, then again the process is the same as described earlier for the original pill counting cycle to obtain more pills to finish the filling of the batch line. Once the operator 22 has addressed the issue, the controller 18 receives an indication of such correction (block 862). If the pill count was correct (or the necessary corrections have been made), the controller 18 will extinguish the LEDs 218 at the shutter assembly 38 and will capture a photographic image of the filled compartments 94 in the tray 40 for later verification purposes (block 864). Then the controller 18 will identify the current batch line as complete in memory (block 866). The controller 18 then checks to see whether all batch lines of the current batch have been completed (block 868). If so, then the completion of the batch is marked in memory (block 870) and the filling blister packs cycle 540 ends. If more batch lines remain, then the controller 18 directs the process back to the counting pills cycle 538 described above to lead the operator 22 back to obtain another medication from another canister 26.

It may be possible for a batch to require more canisters 26 than what can fit on the staging bar 32. For example, if a batch required eight different medications, and several of the canisters 26 did not have enough inventory, then a staging bar 32 with eight locations could not retain all the required canisters 26. In these circumstances, the controller 18 will proceed to start a new batch line but for which the necessary canister 26 is not located at the staging bar 32. The controller 18 will then go back to exchanging canisters between the staging bar 32 and the carousels 24 as described above. The controller 18 will direct the operator 22 to put back enough of the canisters 26 containing medications that are no longer needed in the tray 40 to make room for those canisters 26 that need to be added to finish the tray 40. Again, this process may be optimized to reduce the number of canister 26 exchanges that will be needed for the next batch, and so on.

A typical batch will be all fills for an entire pass time of an order, and will be made up of thirty blister packs 90. Therefore a typical batch will require two trays 40. After a tray 40 has been filled and the operator 22 has moved the tray 40 to the post-fill staging area as described in detail below, the controller 18 will check if all fills for the current batch are done, i.e. whether there are more trays 40 needed for the current batch. If the batch is not finished, the controller 18 will prompt the operator 22 to put a new tray 40 into the shutter assembly 38. The system will validate that the tray 40 inserted is registered and is not already in use, giving an error message on the display monitor 36 and telling the operator 22 to try a different tray 40 if the inserted tray 40 is not valid. In this regard, the counting and filling steps cycle over and over until the batch is finished.

With reference to FIG. 30, when a tray 40 has all blister packs 90 filled, the operator 22 will be instructed to put the tray 40 into a storage location so it will be made available to a verification station by following the series of operations shown defining the post-fill staging cycle 542. This cycle 542 begins with the controller 18 actuating the unlocking of the tray 40 at the shutter assembly 38 and prompting the operator 22 to remove and scan the tray 40 (block 880). The controller 18 then receives the tray barcode scan (block 882) and verifies whether the correct tray 40 has been scanned (block 884). If the tray 40 scanned is incorrect, then the controller 18 displays an error to the operator 22 regarding the improper tray 40 (block 886) and awaits another corrected scan. Once the correct tray 40 is scanned, the controller 18 prompts the operator 22 to apply the tray cover to the tray 40 (to prevent blister packs 90 from falling out) and to stage the tray 40 for post-filling operations (block 888). Next, the operator 22 should take the tray 40 to the post-fill staging area along with the hand scanner. The operator 22 should scan an open location in the post-fill staging area (not shown). The controller 18 receives the scan of the post-filling staging location barcode (block 890) and then verifies whether the scanned location is available and valid for receiving the tray 40 (block 892). If the validation fails, then the controller 18 will display an error to the operator 22 regarding the invalid or filled location (block 894) and returns to step 888 to request another scan. If the validation checks pass, the tray 40 will be assigned to the selected post-fill staging location (block 896). The post-fill staging cycle 542 then ends and the filling process continues for another tray or another order as previously described.

Figure 31:
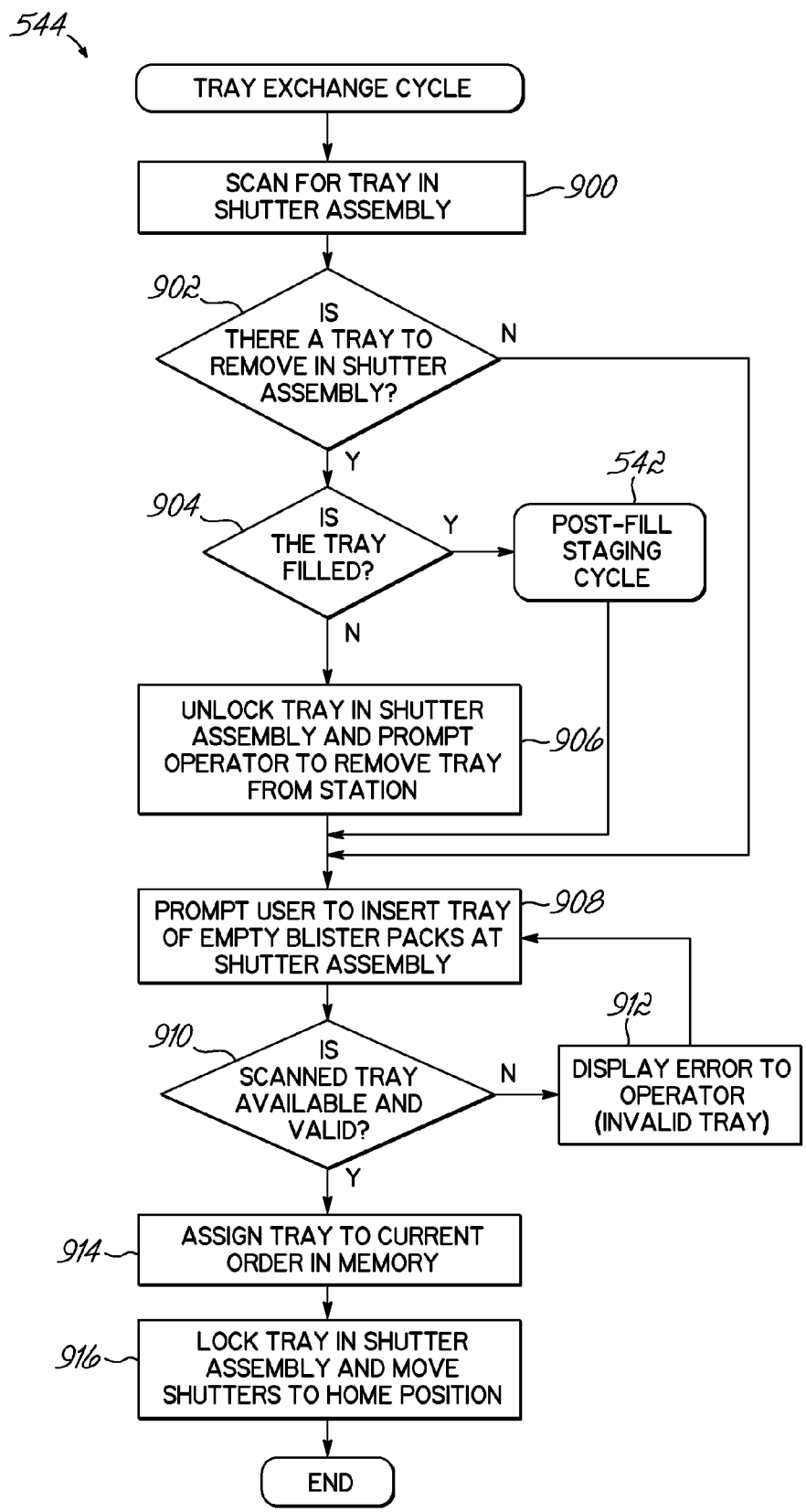
FIG. 31 is a flowchart showing a sequence of operations that may be performed during the tray exchange cycle of FIG. 21.

With reference to FIG. 31, the series of operations forming the tray exchange cycle 544 is illustrated in further detail. The controller 18 prompts a scan for a tray 40 in the shutter assembly 38 to begin this cycle (block 900). The controller 18 determines from this scan whether there are any trays 40 to remove in the shutter assembly 38 (block 902). If there is a tray 40 in the shutter assembly 38, then the controller 18 determines if the tray 40 is filled (block 904). If the tray 40 is not filled, then the controller 18 unlocks the tray 40 in the shutter assembly 38 and prompts the operator to remove the tray 40 from the manual packaging station 14 (block 906). If the tray 40 is filled, then the controller 18 operates the post-fill staging cycle 542 as described above with reference to FIG. 30. Once the tray 40 has been removed by one of these steps, or if no tray 40 was in the shutter assembly 38, the controller 18 prompts the operator 22 to insert a tray 40 of empty blister packs 90 at the shutter assembly 38 (block 908). The controller 18 then actuates a scan of the tray 40 and determines if the scanned tray 40 in the shutter assembly 38 is available and valid for the current order (block 910). If the tray 40 cannot be used for the current order, then the controller 18 displays an error to the operator 22 regarding this deficiency (block 912) and prompts for another tray 40. If the tray 40 is verified for the current order, then the controller 18 assigns the tray 40 to the current order in memory (block 914). The shutter assembly 38 then locks the tray 40 in position and moves the shutters 174 to the home position providing access to the first compartment 94 of the blister packs 90 (block 916) and the tray exchange cycle 544 ends. The controller 18 can then return to the manual filling master cycle as described above.

Figure 32A:
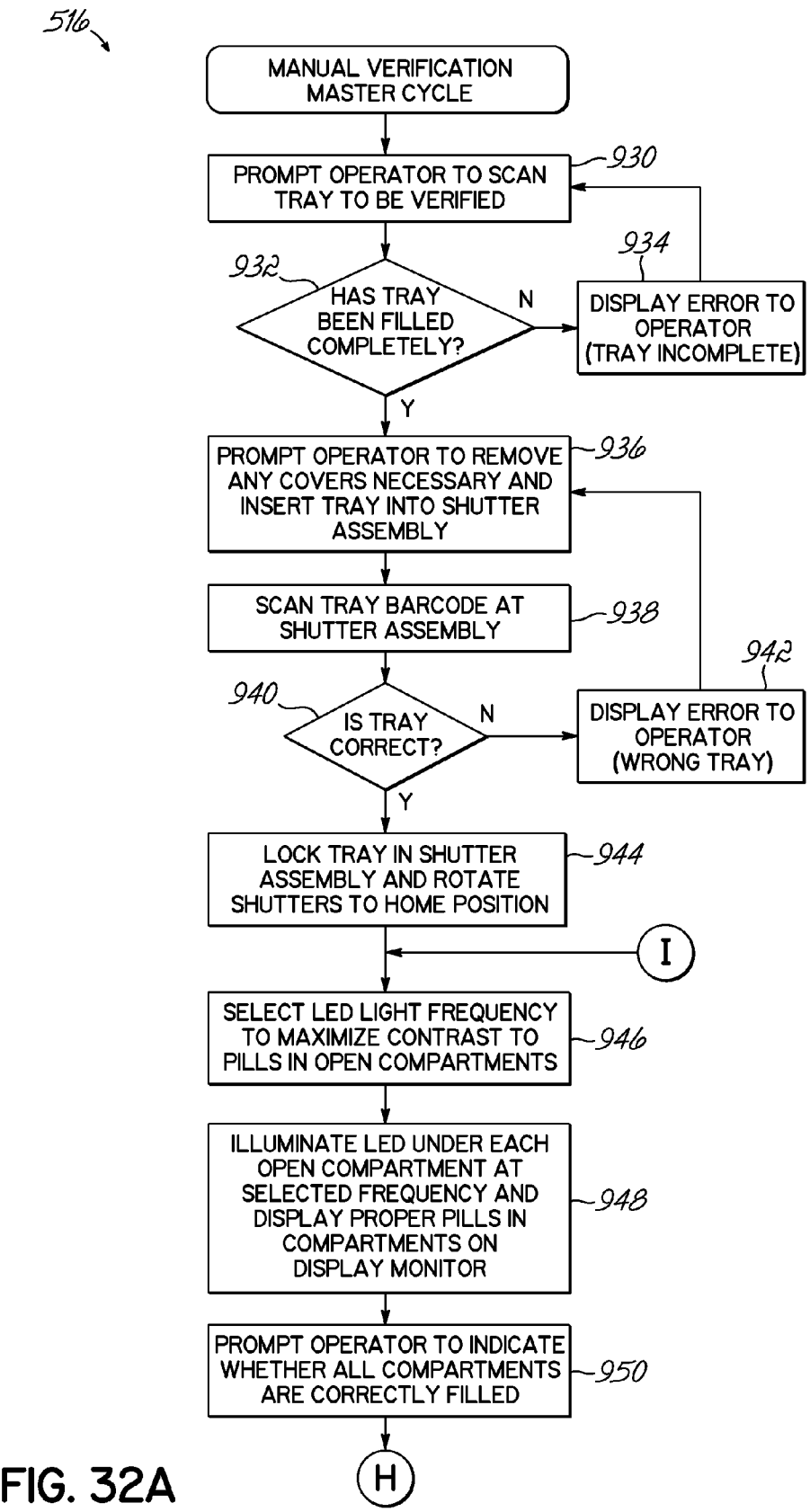
FIG. 32A is a flowchart showing a sequence of operations that may be performed during the manual verification master cycle of FIG. 20.
Figure 32B:
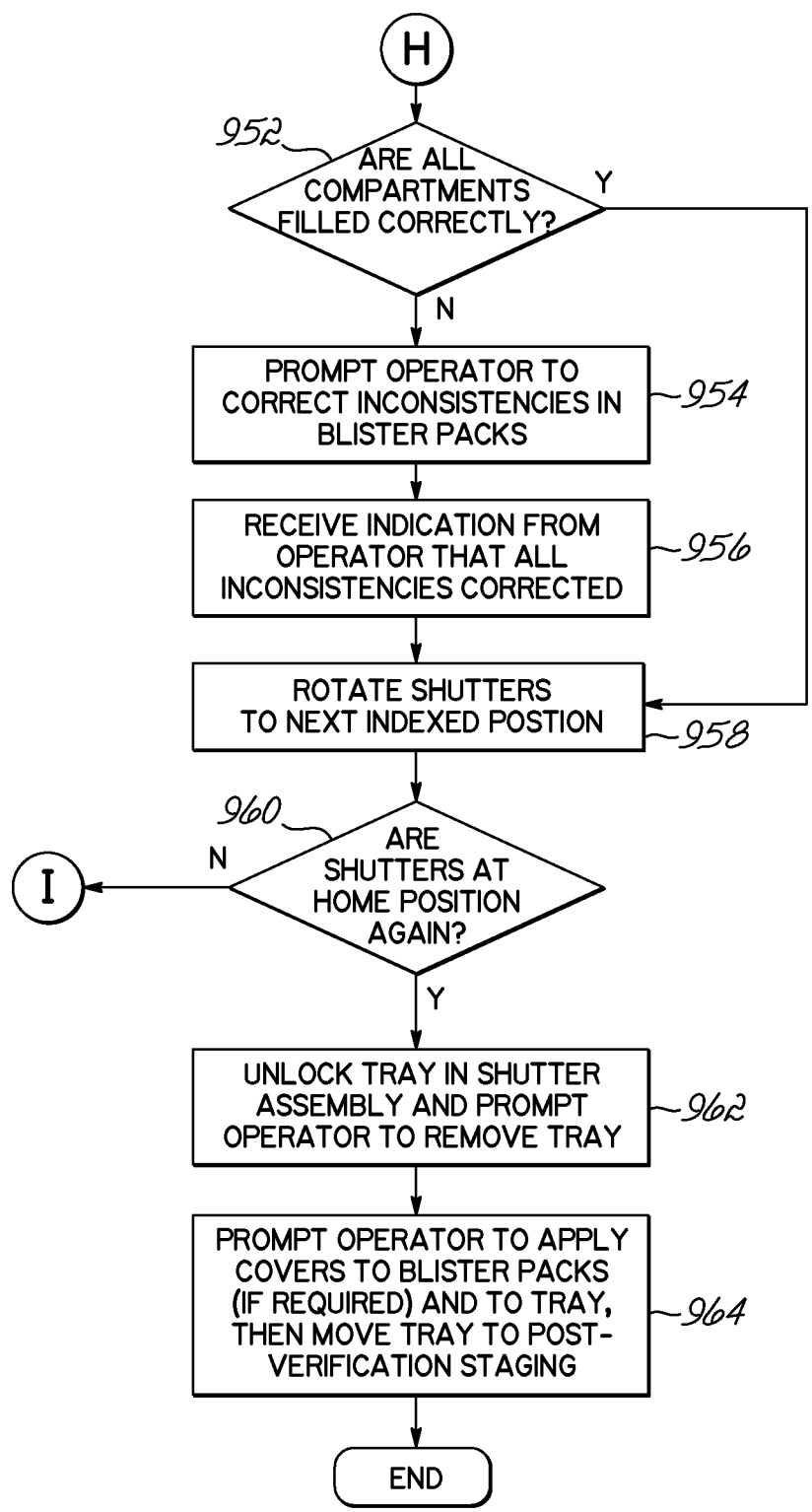
FIG. 32B is a flowchart showing a further sequence of operations that may be performed during the manual verification master cycle of FIG. 32A

When the manual packaging station 14 is being used as a verification station as described briefly above, then the controller 18 operates the series of operations defining the manual verification master cycle 516 as shown in FIGS. 32A and 32B. To this end, the controller 18 prompts the operator 22 to scan a filled tray 40 to be verified at one of the post-fill staging locations (block 930). The controller 18 then determines if the tray 40 has been filled completely (block 932). An example circumstance where a tray 40 might not be completely filled is when the tray 40 is filled partially at an automated packaging station 16 and partially at a manual packaging station 14. If the tray 40 is not confirmed to be filled completely, then an error is displayed to the operator 22 regarding the incomplete filling (block 934) and the controller 18 prompts for another tray 40 to be scanned. If the tray 40 has been filled completely, then the controller 18 prompts the operator 22 to remove any covers from the tray 40 and/or from the blister packs 90 and then to insert the tray 40 into the shutter assembly 38 (block 936). The controller 18 then actuates a scan of the tray barcode (block 938) and verifies whether the inserted tray 40 is correct (block 940). If the tray 40 inserted is not correct, then an error is displayed to the operator 22 regarding the incorrect tray insertion (block 942). Once the tray 40 has been verified within the shutter assembly 38, the shutter assembly 38 locks the tray 40 in position and the shutters 176 are rotated to the home position at the first compartments 94 (block 944). The verification process may then begin at the shutter assembly 38.

To this end, the controller 18 selects an LED light frequency that will maximize contrast to the pills in the open compartments 94 (block 946). The LEDs 218 under each open compartment 94 are then activated or illuminated at the selected frequency and the controller 18 displays the pills that should be in those compartments 94 on the display monitor 36 (block 948). The controller 18 then prompts the operator 22 to indicate whether all of the compartments 94 currently visible are correctly filled (block 950). This process may also use the photographic image taken immediately after filling the blister packs 90 to help verify correct filling. The controller 18 determines if all the compartments 94 were correctly filled from the operator's input (block 952). If one or more of the compartments 94 are not filled correctly, then the controller 18 prompts the operator 22 to correct the inconsistencies in the blister packs 90 (block 954). Once this is completed by the operator 22, the controller 18 receives an indication from the operator 22 such as by input to the visual display monitor 36 that the inconsistencies have been corrected (block 956). Once this is completed or if the compartments 94 were all filled correctly, the shutters 174 are rotated to the next indexed position to reveal another set of compartments 94 (block 958).

The controller 18 then detects whether the shutters 174 are back at the home position (block 960). If not, then the verification process continues by the controller 18 returning to step 946 to select a light frequency for the LEDs 218 of the next set of revealed compartments 94. If the shutters 174 are back to the home position, indicating that verification is complete for the tray 40, then the shutter assembly 38 unlocks the tray 40 and the controller 18 prompts the operator 22 to remove the tray 40 (block 962). The controller 18 then prompts the operator 22 to apply covers to the blister packs 90, if required (e.g., if these covers were removed before verification), and to the tray 40, then to move the tray 40 to post-verification staging (block 964). From this staging area, the orders of blister packs 90 in the trays 40 for monthly prescriptions or PRN prescriptions can be collated together and packaged for shipping to the appropriate facilities and patients. The controller 18 then ends the manual verification master cycle 516 or repeats the cycle 516 for another tray 40 if desired. Consequently, the manual packaging station 14 may also be used for required human verifications of the filling conducted at other stations 14, 16.

It will be understood that the various steps of the prescription organization and filling/verification processes described above may be reordered or reconfigured as required in other embodiments of a filling process and apparatus. The particular layout of the manual packaging station 14 may further be modified as the operator 22 desires, such as for more efficient movement of canisters 26. The processes described herein are also not limited to the flowchart representations, but those flowcharts are an exemplary embodiment.

References herein to directional terms such as "vertical", "horizontal", "upper", "lower", "raise", "lower", etc. are made by way of example, and not by way of limitation, to establish a frame of reference. It is understood by persons of ordinary skill in the art that various other frames of reference may be equivalently employed for purposes of describing the embodiments of the invention.

It will be understood that when an element is described as being "attached", "connected", or "coupled" to or with another element, the element can be directly connected or coupled to the other element or, instead, one or more intervening elements may be present. In contrast, when an element is described as being "directly attached", "directly connected", or "directly coupled" to another element, there are no intervening elements present. When an element is described as being "indirectly attached", "indirectly connected", or "indirectly coupled" to another element, there is at least one intervening element present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising."

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A method for filling packagings with at least one medication, each packaging including a body with a plurality of separated compartments for separately holding different medications for a single pass time, the method comprising:
    producing filling instructions for an order, including an allocation of medications to separated compartments in a plurality of the packagings, each packaging adapted to receive only the medication to be taken by a patient at a specified medicine pass time, wherein producing filling instructions for the order further comprises:
        receiving a plurality of prescriptions for a patient, each prescription identifying a unique medication and a dosage schedule for that medication;
        allocating each medication from the plurality of prescriptions to the plurality of packagings based on the dosage schedule for each medication;
        identifying any undesirable drug contra-indications between two medications in the same packaging;
        if an undesirable drug contra-indication between two medications is present in any of the packagings, modifying the allocation of one of the conflicting medications to different packagings to avoid the undesirable drug contra-indication;

identifying administration time preferences for the patient; and modifying the allocation of medications to the plurality of packagings based on the administration time preference;

operating a packaging station to fill the plurality of the packagings with the at least one medication according to the filling instructions, by placing different medications into different separated compartments of the packagings for specified medicine pass times requiring multiple medications; and verifying that each of the plurality of the packagings have been accurately filled according to the filling instructions at a verification station.

2. The method of claim 1, wherein producing filling instructions for an order further comprises:

receiving a plurality of prescriptions, each prescription including prescription data;

analyzing the prescription data of each loaded prescription; and generating the filling instructions based at least in part on the analyzed prescription data of each prescription.

3. The method of claim 2, wherein the prescription data of each received prescription indicates a medication type associated with the received prescription, and analyzing the prescription data of each received prescription comprises:

determining the medication type of each received prescription, wherein the generated filling instructions are based at least in part on the determined medication type of at least one of the received prescriptions.

4. The method of claim 2, wherein the prescription data of each received prescription identifies a patient associated with the received prescription, and analyzing the prescription data of each received prescription comprises:

determining the identified patient of each received prescription, wherein the generated filling instructions are based at least in part on the determined identified patient of at least one of the received prescriptions.

5. The method of claim 4, wherein the prescription data of each received prescription indicates patient dosing preferences for the identified patient, and the generated filling instructions are based at least in part on the identified patient dosing preferences.

6. The method of claim 2, wherein the prescription data of each received prescription indicates dosage instructions associated with the received prescription, and analyzing the prescription data of each received prescription comprises:

determining the dosage instructions of each received prescription, wherein the generated filling instructions are based at least in part on the determined dosage instructions of at least one of the received prescriptions.

7. The method of claim 1, wherein producing filling instructions for the order further comprises:

receiving a plurality of prescriptions for a patient, each prescription identifying a unique medication and a dosage schedule for that medication;

allocating each medication from the plurality of prescriptions to the plurality of packagings based on the dosage schedule for each medication; and optimizing the allocation of medications to the plurality of packagings by modifying the allocations of medications to minimize the number of packagings required to fill the entire order.

8. A method for filling packagings with at least one medication, each packaging including a body with a plurality of separated compartments for separately holding different medications, the method comprising:

producing filling instructions for an order, including an allocation of medications to separated compartments in a plurality of the packagings, each packaging adapted to receive only the medication to be taken by a patient at a specified medicine pass time or as needed;

operating a packaging station to fill the plurality of the packagings with the at least one medication according to the filling instructions, by placing different medications into different separated compartments of the packagings for specified medicine pass times requiring multiple medications;

verifying that each of the plurality of the packagings have been accurately filled according to the filling instructions at a verification station, wherein the packagings are filled in a drug packaging system that includes a plurality of packaging stations, and the method further comprises:

assigning an order to be filled at one of the packaging stations only when the packaging station includes sufficient inventory of medications to fill the plurality of packagings to be filled for the order; and managing the inventory of the plurality of packaging stations to enable optimization of filling of orders by the drug packaging system.

9. The method of claim 8, wherein the packagings of an order require filling at multiple packaging stations, and further comprising:

producing the filling instructions independently for the multiple packaging stations needed to fill the order;

operating the multiple packaging stations to fill the plurality of the packagings with the at least one medication according to the filling instructions; and managing the filling and verification of the plurality of the packagings such that the entire order is prepared for collation together and shipment with minimized delays.

10. A method for filling packagings with at least one medication, each packaging including a body with a plurality of separated compartments for separately holding different medications, the method comprising:

producing filling instructions for an order, including an allocation of medications to separated compartments in a plurality of the packagings, each packaging adapted to receive only the medication to be taken by a patient at a specified medicine pass time or as needed;

operating a packaging station to fill the plurality of the packagings with the at least one medication according to the filling instructions, by placing different medications into different separated compartments of the packagings for specified medicine pass times requiring multiple medications;

verifying that each of the plurality of the packagings have been accurately filled according to the filling instructions at a verification station, wherein the packaging station is a manual packaging station including at least one storage carousel containing canisters of medications, a staging bar configured to temporarily retain the canisters, a counting mechanism for dispensing a desired quantity of the medication from the canisters, and a loading table for holding a tray with a plurality of the packagings, and operating the packaging station further comprises:

delivering the filling instructions to an operator at the manual packaging station, the filling instructions including directions on how the operator should manually move canisters between the at least one storage carousel, the staging bar, and the counting mechanism and how the operator should manually fill the separated compartments of each packaging in the tray at the loading table, with only one medication at a time being handled by the operator; and prompting the operator for barcode scans and manual input to verify proper movements of canisters and medications from the storage carousels to the loading table and into the separated compartments of the plurality of packagings.

11. The method of claim 10, wherein operating the packaging station further comprises:

retrieving a sorted list of pending orders for a plurality of patients, the pending orders being sorted by priority of which pending orders should be filled first;

assigning a pending order from the sorted list of pending orders to the manual packaging station only when the manual packaging station contains sufficient inventory in the canisters to fill the plurality of packagings for that pending order; and prioritizing the pending orders assigned to the manual packaging station to minimize the number of canister exchanges required by the operator when a new tray of the packagings is to be filled at the loading table.

12. The method of claim 10, wherein delivering the filling instructions to the operator further comprises:

determining a current batch of canisters of medications needed to fill the plurality of packagings on the tray;

prompting the operator to return any canisters not needed for the current batch from the staging bar to the carousels;

prompting the operator to move the canisters needed for the current batch from the carousels to the staging bar;

prompting the operator to dispense the desired quantity of a first medication from a first canister on the staging bar at the counting mechanism;

prompting the operator to fill the first medication into at least a portion of the packagings at the loading table; and repeating the dispensing and filling prompts for other medications and canisters located on the staging bar until the current batch is complete.

13. The method of claim 12, wherein delivering the filling instructions to the operator further comprises:

generating a new batch of canisters of medications needed to fill a plurality of packagings on another tray for the order;

repeating the return canisters, move canisters, dispense medications, and fill packagings prompts for the new batch; and continuing the generation of new batches of canisters and the filling prompts until the plurality of packagings for the entire order have been filled.

14. The method of claim 12, wherein the loading table includes a shutter assembly for holding the tray, the shutter assembly includes a shutter located above each of the packagings with an opening adapted to provide access to only one of the compartments of each packaging, and delivering the filling instructions further comprises:

actuating the shutters so that only a first compartment of each packaging is open for filling;

activating a light emitting diode located below each first compartment that is to receive a medication from the operator;

waiting for confirmation from the operator that all of the first compartments have been filled as desired;

imaging each of the first compartments upon confirmation from the operator of filling for later verification of the filling; and repeating the actuation of shutters and light emitting diodes for each other compartment of the packagings to be filled with medications.

15. The method of claim 14, wherein the shutters on the shutter assembly are rotatable, and actuating the shutters further comprises:

rotating each of the shutters simultaneously in an indexed manner such that the same compartment of each packaging in the tray is accessible to the operator.

16. The method of claim 14, wherein activating the light emitting diode below each first compartment further comprises:

identifying the physical characteristics of the packagings and of the medication to be placed in the packagings; and selecting a frequency of light emitted by the light emitting diodes to maximize visible contrast of the medication when placed in the compartments of the packagings during filling.

17. The method of claim 12, wherein whenever the operator is prompted to move a canister of medication from a first location to a second location, the prompting further comprises:

illuminating at least one of a light emitting diode and a display at the first location to identify which canister requires movement;

requesting a scan of the canister at the first location to verify the correct canister is picked up by the operator;

following verification, illuminating at least one of a light emitting diode and a display at the second location to prompt movement of the operator to the second location;

requesting a scan of both the second location and the canister to verify that the correct canister is still being put into the second location; and extinguishing the light emitting diode and the display at the second location only upon a verified scan of the second location and the canister.

18. A method for filling packagings with at least one medication, each packaging including a body with a plurality of separated compartments for separately holding different medications, the method comprising:

producing filling instructions for an order, including an allocation of medications to separated compartments in a plurality of the packagings, each packaging adapted to receive only the medication to be taken by a patient at a specified medicine pass time or as needed;

operating a packaging station to fill the plurality of the packagings with the at least one medication according to the filling instructions, by placing different medications into different separated compartments of the packagings for specified medicine pass times requiring multiple medications;

verifying that each of the plurality of the packagings have been accurately filled according to the filling instructions at a verification station, wherein the verification station is a manual verification station including a loading table having a shutter assembly for holding a tray of the packagings, the shutter assembly includes a shutter located above each of the packagings with an opening adapted to provide access to only one of the compartments of each packaging, and verifying that each of the plurality of the packagings has been accurately filled further comprises:

scanning a tray inserted into the shutter assembly;

retrieving information about the medications that should be filling the compartments of the packagings on the tray;

actuating the shutters so that only a first compartment of each packaging is open for inspection;

activating a light emitting diode located below each first compartment that is to be inspected;

displaying the information about the medications that should be filling the compartments to the operator;

prompting the operator to correct any discrepancies between the displayed information and the actual packagings;

waiting for confirmation from the operator that all of the first compartments have been filled as displayed in the information; and repeating the actuation of shutters and light emitting diodes, the display of information, the prompt to correct discrepancies, and the confirmation for each other compartment of the packagings that was filled with medications.

19. The method of claim 18, wherein verifying that each of the plurality of the packagings has been accurately filled further comprises:

prompting the operator to remove any covers from the tray and packagings in the tray before insertion into the shutter assembly;

printing replacement covers for the packagings in the tray following verification of the filled medications in the packagings; and prompting the operator to reapply the covers or the replacement covers to the tray and packagings following verification of the filled medications in the packagings.

20. The method of claim 18, wherein the shutters on the shutter assembly are rotatable, and actuating the shutters further comprises:

rotating each of the shutters simultaneously in an indexed manner such that the same compartment of each packaging in the tray is accessible to the operator.

21. The method of claim 18, wherein activating a light emitting diode below each first compartment further comprises:

identifying the physical characteristics of the packagings and of the medication to be inspected in the packagings; and selecting a frequency of light emitted by the light emitting diodes to maximize visible contrast of the medication when placed in the compartments of the packagings during inspection.

\* \* \* \* \*

UNITED STATES PATENT AND TRADEMARK OFFICE
CERTIFICATE OF CORRECTION

Page 1 of 1

PATENT NO. : 8,914,146 B2
APPLICATION NO. : 13/546035
DATED : December 16, 2014
INVENTOR(S) : Carson et al.

It is certified that error appears in the above-identified patent and that said Letters Patent is hereby corrected as shown below:

In the second column of the title page under (56) References Cited, Other Publications, line two, change "Opiinion" to --Opinion--

In the Specification:

At column 10, line number 42, change "pack" to --packs--

At column 12, line number 64, change "have" to --has--

At column 13, line number 22, change "are" to --is-- and at line 32, change "remains" to --remain--

At column 28, line number 31, change "To" to --to--

At column 37, line number 4, change "if" to --is--

In the Claims:

At column 41, claim number 1, line number 16, change "have" to --has--

At column 42, claim number 8, line number 20, change "have" to --has--

Signed and Sealed this
Second Day of June, 2015

Michelle K. Lee
*Director of the United States Patent and Trademark Office*